US010973507B2

(12) United States Patent
Stone et al.

(10) Patent No.: US 10,973,507 B2
(45) Date of Patent: *Apr. 13, 2021

(54) METHOD AND APPARATUS FOR COUPLING SOFT TISSUE TO A BONE

(71) Applicant: Biomet Sports Medicine, LLC, Warsaw, IN (US)

(72) Inventors: Kevin T. Stone, Winona Lake, IN (US); Gregory J. Denham, Warsaw, IN (US); Ryan Harper, Warsaw, IN (US); Ryan A. Kaiser, Leesburg, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 284 days.

This patent is subject to a terminal disclaimer.

(21) Appl. No.: 15/941,481

(22) Filed: Mar. 30, 2018

(65) Prior Publication Data
US 2018/0256153 A1 Sep. 13, 2018

Related U.S. Application Data

(60) Continuation of application No. 14/983,747, filed on Dec. 30, 2015, now Pat. No. 10,154,837, which is a
(Continued)

(51) Int. Cl.
A61B 17/04 (2006.01)
A61F 2/08 (2006.01)
(Continued)

(52) U.S. Cl.
CPC ........ *A61B 17/0401* (2013.01); *A61F 2/0811* (2013.01); *A61B 17/0487* (2013.01);
(Continued)

(58) Field of Classification Search
CPC ............ A61B 17/0057; A61B 17/0401; A61B 17/0487; A61B 2017/0458;
(Continued)

(56) References Cited

U.S. PATENT DOCUMENTS 26,501 A 12/1859 Kendrick et al.
64,499 A 5/1867 Daubert
(Continued)

FOREIGN PATENT DOCUMENTS

AU 4957264 A 3/1966
AU 440266 A1 10/1967
(Continued)

OTHER PUBLICATIONS

US 6,238,418 B1, 05/2001, Schwartz (withdrawn)
(Continued)

*Primary Examiner* — Dianne Dornbusch
(74) *Attorney, Agent, or Firm* — Schwegman Lundberg & Woessner, P.A.

(57) ABSTRACT

A method and apparatus for surgically repairing a tear in soft tissue is disclosed. A plurality of collapsible tubes are positioned about the suture. The collapsible tubes are pushed through soft tissue and orthopedic mesh on opposite sides of a tear in soft tissue. When tension is applied to the suture, the tubes are compressed to fix the suture to the soft tissue and draw the soft tissue portions together.

20 Claims, 31 Drawing Sheets

Related U.S. Application Data continuation of application No. 13/751,846, filed on Jan. 28, 2013, now Pat. No. 9,492,158, which is a division of application No. 12/489,168, filed on Jun. 22, 2009, now Pat. No. 8,361,113, which is a continuation-in-part of application No. 12/474,802, filed on May 29, 2009, now Pat. No. 8,088,130, and a continuation-in-part of application No. 11/541,506, filed on Sep. 29, 2006, now Pat. No. 7,601,165, and a continuation-in-part of application No. 11/541,505, filed on Sep. 29, 2006, now Pat. No. 7,658,751, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/347,661, filed on Feb. 3, 2006, now Pat. No. 7,749,250, and a continuation-in-part of application No. 11/347,662, filed on Feb. 3, 2006, now abandoned, and a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836.

(51) Int. Cl.
*A61B 17/00* (2006.01)
*A61B 17/06* (2006.01)
*A61F 2/00* (2006.01)

(52) U.S. Cl.
CPC ............ *A61B 17/06166* (2013.01); *A61B 2017/00336* (2013.01); *A61B 2017/00858* (2013.01); *A61B 2017/044* (2013.01); *A61B 2017/0404* (2013.01); *A61B 2017/0406* (2013.01); *A61B 2017/0417* (2013.01); *A61B 2017/0445* (2013.01); *A61B 2017/0458* (2013.01); *A61B 2017/0477* (2013.01); *A61B 2017/06185* (2013.01); *A61F 2/0063* (2013.01); *A61F 2/08* (2013.01); *A61F 2/0805* (2013.01); *A61F 2002/0829* (2013.01); *A61F 2002/0852* (2013.01); *A61F 2002/0882* (2013.01)

(58) Field of Classification Search
CPC .. A61B 2017/0589; A61B 2017/06185; A61B 2017/0414; A61B 2017/0445; A61B 2017/0404; A61B 2017/0406; A61F 2/0811
See application file for complete search history.

(56) References Cited

U.S. PATENT DOCUMENTS

| | | |
|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 394,739 A | 12/1888 | Toulmin |
| 401,677 A | 4/1889 | Autenrieth |
| 417,805 A | 12/1889 | Beaman |
| 445,875 A | 2/1891 | Brickell |
| 487,304 A | 12/1892 | Todd |
| 687,221 A | 11/1901 | Gaff et al. |
| 762,710 A | 6/1904 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,505,470 A | 8/1924 | Kelm |
| 1,635,066 A | 7/1927 | Wells |
| 1,950,799 A | 3/1934 | Jones |
| 2,042,403 A | 5/1936 | Andrew |
| 2,065,659 A | 12/1936 | Cullen |
| 2,108,206 A | 2/1938 | Meeker |
| 2,121,193 A | 6/1938 | Erich |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,379,629 A | 7/1945 | Eweson |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,549,382 A | 4/1951 | Mitterway |
| 2,562,419 A | 7/1951 | Ferris |
| 2,581,564 A | 1/1952 | Jaime |
| 2,600,395 A * | 6/1952 | Domoj ............... D07B 1/185 87/13 |
| 2,610,631 A | 9/1952 | Calicchio |
| 2,665,597 A | 1/1954 | Hill |
| 2,669,774 A | 2/1954 | Mitchell |
| 2,698,986 A * | 1/1955 | Brown ............... A01K 97/16 289/1.2 |
| 2,760,488 A | 8/1956 | Pierce |
| 2,833,284 A | 5/1958 | Springer |
| 2,846,712 A | 8/1958 | Moe |
| 2,860,393 A | 11/1958 | Brock |
| 2,880,728 A | 4/1959 | Rights |
| 2,881,762 A | 4/1959 | Lowrie |
| 2,883,096 A | 4/1959 | Horace |
| 2,913,042 A | 11/1959 | John |
| 2,947,504 A | 8/1960 | Ruhlman |
| 3,000,009 A | 9/1961 | Selstad |
| 3,003,155 A | 10/1961 | Mielzynski |
| 3,013,559 A | 12/1961 | Thomas |
| 3,037,619 A | 6/1962 | Ernest |
| 3,039,460 A | 6/1962 | Chandler |
| 3,081,781 A | 3/1963 | Stermer |
| 3,090,386 A | 5/1963 | Babcock |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,223,083 A | 12/1965 | Cobey |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Grant |
| RE26,501 E | 12/1968 | Himmelstein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | Mcknight |
| 3,522,803 A | 8/1970 | Majzlin |
| 3,527,223 A | 9/1970 | Shein |
| 3,533,406 A | 10/1970 | Tatum |
| 3,541,591 A | 11/1970 | Hoegerman |
| 3,545,008 A | 12/1970 | Bader, Jr. |
| 3,547,389 A | 12/1970 | Mitchell |
| 3,579,831 A | 5/1971 | Stevens et al. |
| 3,590,616 A | 7/1971 | Schussler |

(56) References Cited

U.S. PATENT DOCUMENTS

| | | |
|---|---|---|
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,650,274 A | 3/1972 | Edwards et al. |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,786,801 A | 1/1974 | Sartorius |
| 3,802,438 A | 4/1974 | Wolvek |
| 3,807,407 A | 4/1974 | Schweizer |
| 3,810,456 A | 5/1974 | Karman |
| 3,825,010 A | 7/1974 | Mc Donald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,896,810 A | 7/1975 | Akiyama |
| 3,907,442 A | 9/1975 | Reid |
| 3,910,281 A | 10/1975 | Kletschka |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-roel et al. |
| 3,961,632 A | 6/1976 | Moossun |
| 3,973,560 A | 8/1976 | Emmett |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | Mcgrew |
| 4,103,690 A | 8/1978 | Harris |
| RE29,811 E | 10/1978 | Bone |
| 4,121,487 A | 10/1978 | Bone |
| 4,143,656 A | 3/1979 | Holmes |
| 4,144,876 A | 3/1979 | Deleo |
| 4,146,022 A | 3/1979 | Johnson et al. |
| 4,149,277 A | 4/1979 | Bokros |
| 4,157,714 A | 6/1979 | Foltz et al. |
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert |
| 4,185,636 A | 1/1980 | Gabbay et al. |
| 4,196,883 A | 4/1980 | Einhorn et al. |
| 4,207,627 A | 6/1980 | Cloutier |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,302,397 A | 11/1981 | Frainier et al. |
| 4,307,723 A | 12/1981 | Finney |
| 4,312,337 A | 1/1982 | Donohue |
| 4,316,469 A | 2/1982 | Kapitanov |
| 4,319,428 A | 3/1982 | Fox |
| 4,326,531 A | 4/1982 | Shimonaka |
| 4,344,193 A | 8/1982 | Kenny |
| 4,345,601 A | 8/1982 | Fukuda |
| 4,349,027 A | 9/1982 | Difrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland et al. |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,597,766 A | 7/1986 | Hilal et al. |
| 4,602,635 A | 7/1986 | Mulhollan et al. |
| 4,602,636 A | 7/1986 | Noiles |
| 4,604,997 A | 8/1986 | De Bastiani et al. |

(56) References Cited

U.S. PATENT DOCUMENTS

| | | |
|---|---|---|
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | Mcgarry et al. |
| 4,632,100 A | 12/1986 | Somers et al. |
| 4,635,637 A | 1/1987 | Schreiber |
| 4,636,121 A | 1/1987 | Miller |
| 4,640,271 A | 2/1987 | Lower |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,771 A | 4/1987 | Wallsten |
| 4,655,777 A | 4/1987 | Dunn |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,711,639 A | 12/1987 | Grundei |
| 4,714,474 A | 12/1987 | Brooks, Jr. et al. |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,329 A | 3/1988 | Mansat |
| 4,728,332 A | 3/1988 | Albrektsson |
| 4,730,615 A | 3/1988 | Sutherland et al. |
| 4,736,746 A | 4/1988 | Anderson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | Mcfarland |
| 4,744,793 A | 5/1988 | Parr et al. |
| 4,750,492 A | 6/1988 | Jacobs |
| 4,751,922 A | 6/1988 | Dipietropolo |
| 4,754,685 A | 7/1988 | Kite et al. |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,779,372 A | 10/1988 | Pozo Obeso |
| 4,781,190 A | 11/1988 | Lee |
| 4,784,126 A | 11/1988 | Hourahane |
| 4,787,882 A | 11/1988 | Claren |
| 4,790,297 A | 12/1988 | Luque |
| 4,790,850 A | 12/1988 | Dunn et al. |
| 4,793,363 A | 12/1988 | Ausherman et al. |
| 4,795,468 A | 1/1989 | Hodorek et al. |
| 4,809,695 A | 3/1989 | Gwathmey et al. |
| 4,813,406 A | 3/1989 | Ogle, II |
| 4,813,416 A | 3/1989 | Pollak et al. |
| 4,823,780 A | 4/1989 | Odensten et al. |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,836,080 A | 6/1989 | Kite, III et al. |
| 4,838,282 A | 6/1989 | Strasser et al. |
| 4,841,960 A | 6/1989 | Garner |
| 4,846,835 A | 7/1989 | Grande |
| 4,851,005 A | 7/1989 | Hunt et al. |
| 4,858,601 A | 8/1989 | Glisson |
| 4,858,603 A | 8/1989 | Clemow et al. |
| 4,858,608 A | 8/1989 | Mcquilkin |
| 4,860,513 A | 8/1989 | Whitman |
| 4,863,383 A | 9/1989 | Grafelmann |
| 4,870,957 A | 10/1989 | Goble et al. |
| 4,872,450 A | 10/1989 | Austad |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,917,700 A | 4/1990 | Atkins |
| 4,919,667 A | 4/1990 | Richmond |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,467 A | 8/1990 | Ohi et al. |
| 4,946,468 A | 8/1990 | Li |
| 4,950,270 A | 8/1990 | Bowman et al. |
| 4,950,285 A | 8/1990 | Wilk |
| 4,959,069 A | 9/1990 | Brennan et al. |
| 4,960,381 A | 10/1990 | Niznick |
| 4,961,741 A | 10/1990 | Hayhurst |
| 4,962,929 A | 10/1990 | Melton, Jr. |
| 4,968,315 A | 11/1990 | Gatturna |
| 4,968,317 A | 11/1990 | Tormala et al. |
| 4,969,886 A | 11/1990 | Cziffer et al. |
| 4,974,488 A * | 12/1990 | Spralja ............ D04C 1/12 57/202 |
| 4,974,656 A | 12/1990 | Judkins |
| 4,976,736 A | 12/1990 | White et al. |
| 4,978,350 A | 12/1990 | Wagenknecht |
| 4,979,956 A | 12/1990 | Silvestrini |
| 4,983,176 A | 1/1991 | Cushman et al. |
| 4,983,184 A | 1/1991 | Steinemann |
| 4,983,240 A | 1/1991 | Orkin et al. |
| 4,988,351 A | 1/1991 | Paulos et al. |
| 4,994,074 A | 2/1991 | Bezwada et al. |
| 4,997,433 A | 3/1991 | Goble et al. |
| 5,002,545 A | 3/1991 | Whiteside et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,019,093 A | 5/1991 | Kaplan et al. |
| 5,020,713 A | 6/1991 | Kunreuther |
| 5,026,398 A | 6/1991 | May et al. |
| 5,028,569 A | 7/1991 | Cihon |
| 5,030,224 A | 7/1991 | Wright |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A * | 11/1991 | Gilbertson ............ A61F 2/2445 623/2.37 |
| 5,067,962 A | 11/1991 | Campbell et al. |
| 5,071,420 A | 12/1991 | Paulos et al. |
| 5,074,874 A | 12/1991 | Yoon et al. |

(56) References Cited

U.S. PATENT DOCUMENTS

| | | |
|---|---|---|
| 5,078,731 A | 1/1992 | Hayhurst |
| 5,078,843 A | 1/1992 | Pratt |
| 5,080,050 A | 1/1992 | Dale |
| 5,080,675 A | 1/1992 | Lawes et al. |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,727 A | 3/1992 | Moghe |
| 5,092,866 A | 3/1992 | Breard et al. |
| 5,098,433 A | 3/1992 | Freedland |
| 5,098,435 A | 3/1992 | Stednitz et al. |
| 5,100,415 A | 3/1992 | Hayhurst |
| 5,100,417 A | 3/1992 | Cerier |
| 5,108,433 A | 4/1992 | May et al. |
| 5,112,335 A | 5/1992 | Laboureau et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,783 A | 7/1992 | Moghe et al. |
| 5,127,785 A | 7/1992 | Faucher |
| 5,129,901 A | 7/1992 | Decoste X |
| 5,129,902 A | 7/1992 | Goble et al. |
| 5,129,904 A | 7/1992 | Illi |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,217,495 A | 6/1993 | Kaplan et al. |
| 5,219,359 A | 6/1993 | McQuilkin et al. |
| 5,222,976 A | 6/1993 | Yoon |
| 5,224,940 A | 7/1993 | Dann et al. |
| 5,224,946 A | 7/1993 | Hayhurst et al. |
| 5,226,914 A | 7/1993 | Caplan et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | Dipoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,282,868 A | 2/1994 | Bahler |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,330,534 A | 7/1994 | Herrington et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,344,460 A | 9/1994 | Turanyi et al. |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,354,299 A | 10/1994 | Coleman |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,358,530 A | 10/1994 | Hodorek |
| 5,358,531 A | 10/1994 | Goodfellow et al. |
| 5,360,431 A | 11/1994 | Puno et al. |
| 5,362,294 A | 11/1994 | Seitzinger |
| 5,362,911 A | 11/1994 | Cevasco et al. |
| 5,364,400 A | 11/1994 | Rego, Jr. et al. |
| 5,366,461 A | 11/1994 | Blasnik |
| 5,368,599 A | 11/1994 | Hirsch et al. |
| 5,370,646 A | 12/1994 | Reese et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,376,118 A | 12/1994 | Kaplan |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | De La Torre |
| 5,391,182 A | 2/1995 | Chin |
| 5,393,302 A | 2/1995 | Clark et al. |
| RE34,871 E | 3/1995 | Mcguire et al. |
| 5,395,374 A | 3/1995 | Miller et al. |
| 5,395,401 A | 3/1995 | Bahler |
| 5,397,356 A | 3/1995 | Goble et al. |

(56) References Cited

U.S. PATENT DOCUMENTS

| | | |
|---|---|---|
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,824 A | 6/1995 | Akerfeldt et al. |
| 5,423,860 A | 6/1995 | Lizardi et al. |
| 5,425,733 A | 6/1995 | Schmieding |
| 5,425,766 A | 6/1995 | Bowald |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,721 A | 10/1995 | Legrand |
| 5,456,722 A | 10/1995 | Mcleod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,470,354 A | 11/1995 | Hershberger et al. |
| 5,472,452 A | 12/1995 | Trott |
| 5,474,565 A | 12/1995 | Trott |
| 5,474,568 A | 12/1995 | Scott et al. |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,480,446 A | 1/1996 | Goodfellow et al. |
| 5,484,442 A | 1/1996 | Melker et al. |
| 5,486,197 A | 1/1996 | Le et al. |
| 5,486,359 A | 1/1996 | Caplan et al. |
| 5,489,210 A | 2/1996 | Hanosh |
| 5,490,750 A | 2/1996 | Gundy |
| 5,495,974 A | 3/1996 | Deschenes et al. |
| 5,496,290 A | 3/1996 | Ackerman |
| 5,496,331 A | 3/1996 | Xu et al. |
| 5,496,348 A | 3/1996 | Bonutti |
| 5,498,302 A | 3/1996 | Davidson |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,011 A | 7/1996 | Greene, Jr. et al. |
| 5,534,012 A | 7/1996 | Bonutti |
| 5,534,033 A | 7/1996 | Simpson |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A * | 8/1996 | Kensey ............... A61B 17/0057 604/15 |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,664 A | 10/1996 | Durlacher et al. |
| 5,562,668 A | 10/1996 | Johnson |
| 5,562,669 A | 10/1996 | Mcguire |
| 5,562,683 A | 10/1996 | Chan |
| 5,562,685 A | 10/1996 | Mollenauer et al. |
| 5,562,686 A | 10/1996 | Sauer et al. |
| 5,569,252 A | 10/1996 | Justin et al. |
| 5,569,269 A | 10/1996 | Hart et al. |
| 5,569,305 A | 10/1996 | Bonutti |
| 5,569,306 A | 10/1996 | Thal |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,745 A | 5/1997 | Schwartz |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle |

(56) References Cited

U.S. PATENT DOCUMENTS

| | | |
|---|---|---|
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | Mcdevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | Mcdevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,677 A | 9/1997 | Wimmer |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,673,546 A | 10/1997 | Abraham et al. |
| 5,674,224 A | 10/1997 | Howell et al. |
| 5,679,723 A | 10/1997 | Cooper |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada |
| 5,690,655 A | 11/1997 | Hart et al. |
| 5,690,676 A | 11/1997 | Dipoto et al. |
| 5,690,678 A | 11/1997 | Johnson |
| 5,693,046 A | 12/1997 | Songer et al. |
| 5,695,497 A | 12/1997 | Stahelin |
| 5,697,929 A | 12/1997 | Mellinger |
| 5,697,969 A | 12/1997 | Schmitt et al. |
| 5,699,657 A * | 12/1997 | Paulson ................ B65H 69/06 28/142 |
| 5,702,397 A | 12/1997 | Goble et al. |
| 5,702,422 A | 12/1997 | Stone |
| 5,702,462 A | 12/1997 | Oberlander |
| 5,702,464 A | 12/1997 | Lackey et al. |
| 5,707,373 A | 1/1998 | Sevrain et al. |
| 5,709,708 A | 1/1998 | Thal et al. |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,716,616 A | 2/1998 | Prockop et al. |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,723,331 A | 3/1998 | Tubo et al. |
| 5,725,529 A | 3/1998 | Nicholson et al. |
| 5,725,549 A | 3/1998 | Lam |
| 5,725,556 A | 3/1998 | Moser et al. |
| 5,725,557 A | 3/1998 | Gatturna et al. |
| 5,725,581 A | 3/1998 | Branemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | De La Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,776,200 A | 7/1998 | Johnson et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,782,925 A | 7/1998 | Collazo et al. |
| 5,785,714 A | 7/1998 | Morgan et al. |
| 5,786,217 A | 7/1998 | Tubo et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor |
| 5,800,447 A | 9/1998 | Wenstrom, Jr. |
| 5,800,543 A | 9/1998 | Mcleod et al. |
| 5,810,824 A | 9/1998 | Chan |
| 5,810,848 A | 9/1998 | Hayhurst |
| 5,811,094 A | 9/1998 | Caplan et al. |
| 5,814,056 A | 9/1998 | Prosst et al. |
| 5,814,069 A | 9/1998 | Schulze et al. |
| 5,814,070 A | 9/1998 | Borzone et al. |
| 5,814,071 A | 9/1998 | Mcdevitt et al. |
| 5,814,072 A | 9/1998 | Bonutti |
| 5,814,073 A | 9/1998 | Bonutti |
| 5,817,095 A | 10/1998 | Smith |
| 5,823,980 A | 10/1998 | Kopfer |
| 5,824,011 A | 10/1998 | Stone et al. |
| 5,824,066 A * | 10/1998 | Gross ................... A61F 2/2448 623/2.36 |
| 5,827,285 A | 10/1998 | Bramlet |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,947 A | 1/1999 | Stamler |
| 5,860,973 A | 1/1999 | Michelson |
| 5,860,978 A | 1/1999 | Mcdevitt et al. |
| 5,868,740 A | 2/1999 | LaVeen et al. |
| 5,868,748 A | 2/1999 | Burke |
| 5,868,789 A | 2/1999 | Huebner |
| 5,871,456 A | 2/1999 | Armstrong et al. |
| 5,871,484 A | 2/1999 | Spievack et al. |
| 5,871,486 A | 2/1999 | Huebner |
| 5,871,490 A | 2/1999 | Schulze et al. |
| 5,871,542 A | 2/1999 | Goodfellow et al. |
| 5,871,543 A | 2/1999 | Hofmann |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,920 A | 5/1999 | Desatnick et al. |

(56) References Cited

U.S. PATENT DOCUMENTS

| | | |
|---|---|---|
| 5,899,938 A | 5/1999 | Sklar et al. |
| 5,906,934 A | 5/1999 | Grande et al. |
| 5,908,421 A | 6/1999 | Beger |
| 5,908,436 A | 6/1999 | Cuschieri et al. |
| 5,910,148 A | 6/1999 | Reimels et al. |
| 5,911,721 A | 6/1999 | Nicholson et al. |
| 5,916,557 A | 6/1999 | Berlowitz-tarrant et al. |
| 5,918,604 A | 7/1999 | Whelan |
| 5,919,232 A | 7/1999 | Chaffringeon et al. |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| 5,928,286 A | 7/1999 | Ashby et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,129 A | 8/1999 | Mcdevitt et al. |
| 5,935,133 A | 8/1999 | Wagner et al. |
| 5,935,134 A | 8/1999 | Pedlick et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | Dipoto et al. |
| 5,961,520 A | 10/1999 | Beck, Jr. et al. |
| 5,961,521 A | 10/1999 | Roger |
| 5,961,524 A | 10/1999 | Crombie |
| 5,963,869 A | 10/1999 | Fehnel |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,964,808 A | 10/1999 | Blaha et al. |
| 5,968,045 A | 10/1999 | Frazier |
| 5,968,047 A | 10/1999 | Reed |
| 5,968,077 A | 10/1999 | Wojciechowicz et al. |
| 5,968,078 A | 10/1999 | Grotz |
| 5,968,099 A | 10/1999 | Badorf et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A * | 11/1999 | Fumex .............. A61B 17/0401 606/232 |
| 5,989,256 A | 11/1999 | Kuslich et al. |
| 5,989,282 A | 11/1999 | Bonutti |
| 5,989,294 A | 11/1999 | Marlow |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,004,351 A | 12/1999 | Tomita et al. |
| 6,004,352 A | 12/1999 | Buni |
| 6,007,538 A | 12/1999 | Levin |
| 6,007,567 A | 12/1999 | Bonutti |
| 6,010,525 A | 1/2000 | Bonutti et al. |
| 6,013,103 A | 1/2000 | Kaufman et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,023,661 A | 2/2000 | Sottery |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,036,695 A | 3/2000 | Smith |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A * | 4/2000 | Hill .................. A61B 17/06166 606/228 |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,146 A | 5/2000 | Carroll et al. |
| 6,066,173 A | 5/2000 | Mckernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,083,257 A | 7/2000 | Taylor et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan et al. |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,127,596 A | 10/2000 | Brown et al. |
| 6,132,433 A | 10/2000 | Whelan |
| 6,132,437 A | 10/2000 | Omurtag |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,150,163 A | 11/2000 | McPherson et al. |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |

(56) References Cited

U.S. PATENT DOCUMENTS

| | | |
|---|---|---|
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,174,324 B1 | 1/2001 | Egan et al. |
| 6,179,840 B1 | 1/2001 | Bowman |
| 6,183,461 B1 | 2/2001 | Matsuura et al. |
| 6,183,737 B1 | 2/2001 | Zaleske et al. |
| 6,187,025 B1 | 2/2001 | Machek |
| 6,190,348 B1 | 2/2001 | Tiemann |
| 6,190,401 B1 | 2/2001 | Green et al. |
| 6,190,411 B1 | 2/2001 | Lo |
| 6,190,415 B1 | 2/2001 | Cooke et al. |
| 6,193,754 B1 | 2/2001 | Seedhom |
| 6,200,318 B1 | 3/2001 | Har-shai et al. |
| 6,200,329 B1 | 3/2001 | Fung et al. |
| 6,200,330 B1 | 3/2001 | Benderev et al. |
| 6,200,606 B1 | 3/2001 | Peterson et al. |
| 6,200,685 B1 | 3/2001 | Davidson |
| 6,203,556 B1 | 3/2001 | Evans et al. |
| 6,203,563 B1 | 3/2001 | Fernandez |
| 6,203,565 B1 | 3/2001 | Bonutti et al. |
| 6,203,572 B1 | 3/2001 | Johnson et al. |
| 6,203,576 B1 | 3/2001 | Afriat et al. |
| 6,206,883 B1 | 3/2001 | Tunc |
| 6,210,376 B1 | 4/2001 | Grayson |
| 6,210,381 B1 | 4/2001 | Morse |
| 6,210,445 B1 | 4/2001 | Zawadzki |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner |
| 6,228,096 B1 | 5/2001 | Marchand |
| 6,231,592 B1 | 5/2001 | Bonutti et al. |
| 6,234,980 B1 | 5/2001 | Bell |
| 6,235,057 B1 | 5/2001 | Roger et al. |
| 6,235,058 B1 | 5/2001 | Huene |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,024 B1 | 6/2001 | Montagnino et al. |
| 6,245,081 B1 | 6/2001 | Bowman |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,929 B1 | 9/2001 | Smith et al. |
| 6,293,961 B2 | 9/2001 | Schwartz et al. |
| 6,296,659 B1 * | 10/2001 | Foerster ............ A61B 17/0469 606/224 |
| 6,299,615 B1 | 10/2001 | Huebner |
| 6,302,888 B1 | 10/2001 | Mellinger et al. |
| 6,302,899 B1 | 10/2001 | Johnson et al. |
| 6,302,915 B1 | 10/2001 | Cooney, III et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,124 B1 | 10/2001 | Gueret |
| 6,309,405 B1 | 10/2001 | Bonutti |
| 6,312,448 B1 | 11/2001 | Bonutti |
| 6,315,788 B1 | 11/2001 | Roby |
| 6,319,224 B1 | 11/2001 | Stout et al. |
| 6,319,271 B1 | 11/2001 | Schwartz et al. |
| 6,328,758 B1 | 12/2001 | Tornier et al. |
| 6,334,064 B1 | 12/2001 | Fiddian-green |
| 6,342,060 B1 | 1/2002 | Adams |
| 6,343,531 B2 | 2/2002 | Amis |
| 6,355,066 B1 | 3/2002 | Kim et al. |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,111 B1 | 5/2002 | Barber |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,456 B1 | 6/2002 | Slate et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 | 7/2002 | Rousseau |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,458,161 B1 | 10/2002 | Gibbs et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| 6,500,208 B1 | 12/2002 | Metzger et al. |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 * | 1/2003 | Fumex ............... A61B 17/0401 606/232 |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 * | 2/2003 | Hein .................... A61F 2/0811 606/232 |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | Mcdevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'addario |

(56) References Cited

U.S. PATENT DOCUMENTS

| | | |
|---|---|---|
| 6,544,281 B2 | 4/2003 | Elattrache et al. |
| 6,547,564 B1 | 4/2003 | Hansson |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,551,353 B1 | 4/2003 | Baker et al. |
| 6,553,802 B1 | 4/2003 | Jacob |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Järvinen |
| 6,565,572 B2 | 5/2003 | Chappius |
| 6,565,573 B1 | 5/2003 | Ferrante |
| 6,569,167 B1 | 5/2003 | Bobechko et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,572,655 B1 | 6/2003 | Johnson |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,592,622 B1 | 7/2003 | Ferguson |
| 6,595,911 B2 | 7/2003 | Lovuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,064 B1 | 8/2003 | Goble et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,626,930 B1 | 9/2003 | Allen et al. |
| 6,629,977 B1 | 10/2003 | Wolf |
| 6,629,997 B2 | 10/2003 | Mansmann |
| 6,632,245 B2 | 10/2003 | Kim |
| 6,635,073 B2 | 10/2003 | Bonutti |
| 6,638,279 B2 | 10/2003 | Bonutti |
| 6,638,286 B1 | 10/2003 | Burbank et al. |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,169 B1 | 11/2003 | Slate et al. |
| 6,645,211 B2 | 11/2003 | Magana |
| 6,645,227 B2 | 11/2003 | Fallin et al. |
| 6,648,903 B1 | 11/2003 | Pierson, III |
| 6,648,921 B2 * | 11/2003 | Anderson ............ A61F 2/0045 600/37 |
| 6,652,450 B2 | 11/2003 | Neisz et al. |
| 6,652,533 B2 | 11/2003 | O'neil |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,669,707 B1 | 12/2003 | Swanstrom et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,712,859 B2 | 3/2004 | Rousseau |
| 6,716,190 B1 | 4/2004 | Glines et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,780 B2 | 6/2004 | Stout et al. |
| 6,752,810 B1 | 6/2004 | Gao et al. |
| 6,752,831 B2 | 6/2004 | Sybert et al. |
| 6,755,836 B1 | 6/2004 | Lewis |
| 6,755,868 B2 | 6/2004 | Rousseau |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,790,210 B1 | 9/2004 | Cragg et al. |
| 6,793,595 B1 | 9/2004 | Monnet |
| 6,802,862 B1 | 10/2004 | Roger et al. |
| 6,808,502 B2 | 10/2004 | Nguyen |
| 6,808,526 B1 | 10/2004 | Magerl et al. |
| 6,814,741 B2 | 11/2004 | Bowman et al. |
| 6,830,572 B2 | 12/2004 | Mcdevitt et al. |
| 6,833,005 B1 | 12/2004 | Mantas |
| 6,835,377 B2 | 12/2004 | Goldberg et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,243 B2 | 5/2005 | Culbert |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,911,202 B2 | 6/2005 | Amir et al. |
| 6,916,292 B2 | 7/2005 | Morawski et al. |
| 6,916,321 B2 | 7/2005 | Tenhuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,923,832 B1 | 8/2005 | Sharkey et al. |
| 6,939,379 B2 | 9/2005 | Sklar |
| 6,946,001 B2 | 9/2005 | Sanford et al. |
| 6,949,102 B2 | 9/2005 | Andrews |
| 6,951,565 B2 | 10/2005 | Keane et al. |
| 6,960,214 B2 | 11/2005 | Burkinshaw |
| 6,966,887 B1 | 11/2005 | Chin |
| 6,966,916 B2 | 11/2005 | Kumar |

(56) References Cited

U.S. PATENT DOCUMENTS

| | | |
|---|---|---|
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,011,682 B2 | 3/2006 | Lashinski et al. |
| 7,033,397 B2 | 4/2006 | Webster et al. |
| 7,048,754 B2 | 5/2006 | Martin et al. |
| 7,052,499 B2 | 5/2006 | Steger et al. |
| 7,060,101 B2 | 6/2006 | O'Connor et al. |
| 7,066,942 B2 | 6/2006 | Treace |
| 7,066,944 B2 | 6/2006 | Laufer et al. |
| 7,081,126 B2 | 7/2006 | Mcdevitt et al. |
| 7,083,638 B2 | 8/2006 | Foerster |
| 7,087,064 B1 | 8/2006 | Hyde |
| 7,087,073 B2 | 8/2006 | Bonutti |
| 7,090,690 B2 | 8/2006 | Foerster et al. |
| 7,097,654 B1 | 8/2006 | Freedland |
| 7,101,395 B2 | 9/2006 | Tremulis et al. |
| 7,105,010 B2 | 9/2006 | Hart et al. |
| 7,105,026 B2 | 9/2006 | Johnson et al. |
| 7,112,221 B2 | 9/2006 | Harris |
| 7,118,578 B2 | 10/2006 | West, Jr. et al. |
| 7,118,583 B2 | 10/2006 | O'quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,148,209 B2 | 12/2006 | Hoemann et al. |
| 7,153,127 B2 | 12/2006 | Struble et al. |
| 7,153,307 B2 | 12/2006 | Scribner |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,179,259 B1 | 2/2007 | Gibbs |
| 7,201,722 B2 | 4/2007 | Krueger |
| 7,207,993 B1 | 4/2007 | Baldwin et al. |
| 7,229,441 B2 | 6/2007 | Trieu et al. |
| 7,235,091 B2 | 6/2007 | Thornes |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,291,177 B2 | 11/2007 | Gibbs |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,354,354 B2 | 4/2008 | Palumbo et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,462,198 B2 | 12/2008 | Webster et al. |
| 7,463,198 B2 | 12/2008 | Deaett et al. |
| 7,465,308 B2 | 12/2008 | Sikora et al. |
| 7,468,074 B2 | 12/2008 | Caborn |
| 7,481,814 B1 | 1/2009 | Metzger |
| 7,484,539 B1 | 2/2009 | Huang |
| 7,485,149 B1 | 2/2009 | White |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,517,357 B2 | 4/2009 | Abrams et al. |
| 7,572,275 B2 | 8/2009 | Fallin et al. |
| 7,572,298 B2 | 8/2009 | Roller et al. |
| 7,578,825 B2 | 8/2009 | Huebner |
| 7,585,311 B2 | 9/2009 | Green et al. |
| 7,588,587 B2 | 9/2009 | Barbieri et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhasen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,691,112 B2 | 4/2010 | Chanduszko et al. |
| 7,695,493 B2 | 4/2010 | Saadat et al. |
| 7,695,503 B1 | 4/2010 | Kaiser |
| 7,703,372 B1 * | 4/2010 | Shakespeare ........ A63B 29/028 87/6 |
| 7,713,188 B2 | 5/2010 | Bouffier |
| 7,713,285 B1 | 5/2010 | Stone et al. |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,762,942 B2 * | 7/2010 | Neisz ................. A61B 17/0482 600/30 |
| 7,771,482 B1 | 8/2010 | Karmon |
| 7,776,041 B1 | 8/2010 | Walters |
| 7,780,701 B1 | 8/2010 | Meridew et al. |
| 7,790,945 B1 | 9/2010 | Watson, Jr. |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,252 B2 | 1/2011 | Criscuolo et al. |
| 7,867,264 B2 | 1/2011 | Mcdevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,896,907 B2 | 3/2011 | Mcdevitt et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,938,847 B2 | 5/2011 | Fanton et al. |
| 7,951,198 B2 | 5/2011 | Sucec et al. |
| 7,955,388 B2 | 6/2011 | Jensen et al. |
| 7,959,650 B2 | 6/2011 | Kaiser et al. |
| 7,976,565 B1 | 7/2011 | Meridew |
| 7,981,140 B2 | 7/2011 | Burkhart |
| 7,998,203 B2 | 8/2011 | Blum |
| 8,034,090 B2 | 10/2011 | Stone et al. |
| 8,062,334 B2 | 11/2011 | Green et al. |
| 8,066,776 B2 | 11/2011 | O'Connor et al. |
| 8,075,574 B2 | 12/2011 | May et al. |
| 8,075,626 B2 | 12/2011 | Dun |
| 8,088,108 B2 | 1/2012 | Kraft |
| 8,088,130 B2 | 1/2012 | Kaiser et al. |
| 8,109,867 B2 | 2/2012 | Rosenblatt |
| 8,114,127 B2 | 2/2012 | West, Jr. |
| 8,114,128 B2 | 2/2012 | Cauldwell et al. |
| 8,118,835 B2 | 2/2012 | Weisel et al. |

(56) References Cited

U.S. PATENT DOCUMENTS

| | | |
|---|---|---|
| 8,118,836 B2 | 2/2012 | Denham et al. |
| 8,118,868 B2 | 2/2012 | May et al. |
| 8,128,658 B2 | 3/2012 | Kaiser et al. |
| 8,137,354 B2 | 3/2012 | Stone |
| 8,137,382 B2 | 3/2012 | Denham et al. |
| 8,137,407 B2 | 3/2012 | Todd et al. |
| 8,142,510 B2 | 3/2012 | Lee et al. |
| 8,147,557 B2 | 4/2012 | Lee et al. |
| 8,147,558 B2 | 4/2012 | Lee et al. |
| 8,162,997 B2 | 4/2012 | Struhl |
| 8,167,906 B2 | 5/2012 | Cauldwell et al. |
| 8,177,810 B2 | 5/2012 | Ferree |
| 8,202,295 B2 | 6/2012 | Kaplan |
| 8,202,318 B2 | 6/2012 | Willobee |
| 8,221,454 B2 | 7/2012 | Schaffhasen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,589 B2 | 11/2012 | Tyber et al. |
| 8,303,604 B2 | 11/2012 | Stone et al. |
| 8,317,825 B2 | 11/2012 | Stone |
| 8,328,806 B2 | 12/2012 | Tyber et al. |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,054 B2 | 1/2013 | Ducharme et al. |
| 8,361,113 B2 | 1/2013 | Stone et al. |
| 8,409,253 B2 | 4/2013 | Stone et al. |
| 8,454,635 B2 | 6/2013 | Paolitto et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,545,535 B2 | 10/2013 | Hirotsuka et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,579,901 B1 | 11/2013 | Foerster |
| 8,579,944 B2 | 11/2013 | Holloway et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,904 B1 | 3/2014 | Schultz |
| 8,672,968 B2 | 3/2014 | Stone et al. |
| 8,672,969 B2 | 3/2014 | Stone et al. |
| 8,702,718 B2 | 4/2014 | Bhatnagar et al. |
| 8,715,297 B1 | 5/2014 | Foerster et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,808,374 B2 | 8/2014 | Eggli |
| 8,828,067 B2 | 9/2014 | Tipirneni et al. |
| 8,840,645 B2 | 9/2014 | Denham et al. |
| 8,858,642 B2 | 10/2014 | Metzger et al. |
| 8,894,715 B2 | 11/2014 | Metzger et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,961,548 B2 | 2/2015 | Buser |
| 8,968,364 B2 | 3/2015 | Berelsman |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,028,509 B2 | 5/2015 | Chu et al. |
| 9,078,644 B2 | 7/2015 | Stone |
| 9,149,267 B2 | 10/2015 | Norton et al. |
| 9,173,651 B2 | 11/2015 | Stone et al. |
| 9,179,950 B2 | 11/2015 | Zajac et al. |
| 9,198,673 B2 | 12/2015 | Stone |
| 9,216,078 B2 | 12/2015 | Conner et al. |
| 9,271,713 B2 | 3/2016 | Denham et al. |
| 9,271,826 B2 | 3/2016 | Eggli et al. |
| 9,289,285 B2 | 3/2016 | Eggli |
| 9,314,235 B2 | 4/2016 | Bojarski et al. |
| 9,314,241 B2 | 4/2016 | Stone et al. |
| 9,357,991 B2 | 6/2016 | Denham et al. |
| 9,357,992 B2 | 6/2016 | Stone et al. |
| 9,370,350 B2 | 6/2016 | Norton |
| 9,381,013 B2 | 7/2016 | Norton |
| 9,402,621 B2 | 8/2016 | Stone et al. |
| 9,408,599 B2 | 8/2016 | Kaiser et al. |
| 9,414,833 B2 | 8/2016 | Stone et al. |
| 9,414,925 B2 | 8/2016 | Metzger et al. |
| 9,468,433 B2 | 10/2016 | Denham et al. |
| 9,486,211 B2 | 11/2016 | Stone et al. |
| 9,492,158 B2 | 11/2016 | Stone et al. |
| 9,498,204 B2 | 11/2016 | Denham et al. |
| 9,504,460 B2 | 11/2016 | Stone et al. |
| 9,510,819 B2 | 12/2016 | Stone et al. |
| 9,510,821 B2 | 12/2016 | Denham et al. |
| 9,532,777 B2 | 1/2017 | Kaiser et al. |
| 9,538,998 B2 | 1/2017 | Stone et al. |
| 9,539,003 B2 | 1/2017 | Stone et al. |
| 9,561,025 B2 | 2/2017 | Stone et al. |
| 9,572,655 B2 | 2/2017 | Denham |
| 9,585,651 B2 | 3/2017 | Lam et al. |
| 9,603,591 B2 | 3/2017 | Denham et al. |
| 9,622,736 B2 | 4/2017 | Stone et al. |
| 9,642,661 B2 | 5/2017 | Stone et al. |
| 9,681,940 B2 | 6/2017 | Stone et al. |
| 9,724,090 B2 | 8/2017 | Kaiser et al. |
| 9,757,119 B2 | 9/2017 | Norton et al. |
| 9,763,656 B2 | 9/2017 | Stone et al. |
| 9,782,245 B2 | 10/2017 | Mujwid et al. |
| 9,788,876 B2 | 10/2017 | Stone |
| 9,801,620 B2 | 10/2017 | Kaiser et al. |
| 9,801,708 B2 | 10/2017 | Denham et al. |
| 9,833,230 B2 | 12/2017 | Stone |
| 9,861,351 B2 | 1/2018 | Kaiser et al. |
| 9,918,826 B2 | 3/2018 | Berelsman et al. |
| 9,918,827 B2 | 3/2018 | Berelsman et al. |
| 1,000,448 A1 | 6/2018 | Kaiser et al. |
| 1,000,449 A1 | 6/2018 | Stone et al. |
| 1,000,458 A1 | 6/2018 | Berelsman et al. |
| 9,993,241 B2 | 6/2018 | Denham et al. |
| 10,022,118 B2 | 7/2018 | Norton et al. |
| 10,092,288 B2 | 10/2018 | Denham et al. |
| 10,098,629 B2 | 10/2018 | Kaiser et al. |
| 10,154,837 B2 | 12/2018 | Stone et al. |
| 10,167,582 B1 | 1/2019 | Pilgeram et al. |
| 10,251,637 B2 | 4/2019 | Stone et al. |
| 10,265,064 B2 | 4/2019 | Stone et al. |
| 10,265,159 B2 | 4/2019 | Denham et al. |
| 10,321,906 B2 | 6/2019 | Stone et al. |
| 10,349,931 B2 | 7/2019 | Stone |
| 10,363,028 B2 | 7/2019 | Norton |
| 10,368,856 B2 | 8/2019 | Stone et al. |
| 10,398,428 B2 | 9/2019 | Denham et al. |
| 10,398,430 B2 | 9/2019 | Stone et al. |
| 10,441,264 B2 | 10/2019 | Stone et al. |
| 10,517,587 B2 | 12/2019 | Denham et al. |
| 10,517,714 B2 | 12/2019 | Stone et al. |
| 10,542,967 B2 | 1/2020 | Kaiser et al. |
| 10,595,851 B2 | 3/2020 | Kaiser et al. |
| 10,603,029 B2 | 3/2020 | Kaiser et al. |
| 10,610,217 B2 | 4/2020 | Stone et al. |
| 10,675,073 B2 | 6/2020 | Stone et al. |
| 10,687,803 B2 | 6/2020 | Denham et al. |
| 10,695,045 B2 | 6/2020 | Kaiser et al. |
| 10,695,052 B2 | 6/2020 | Denham et al. |
| 10,702,259 B2 | 7/2020 | Stone et al. |
| 10,716,557 B2 | 7/2020 | Denham et al. |

(56) References Cited

U.S. PATENT DOCUMENTS

| | | |
|---|---|---|
| 10,729,421 B2 | 8/2020 | Stone et al. |
| 10,729,423 B2 | 8/2020 | Kaiser et al. |
| 10,729,430 B2 | 8/2020 | Denham et al. |
| 10,743,925 B2 | 8/2020 | Stone et al. |
| 10,758,221 B2 | 9/2020 | Berelsman et al. |
| 10,835,232 B2 | 11/2020 | Stone |
| 2001/0002439 A1 | 5/2001 | Bonutti et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0027341 A1 | 10/2001 | Gianotti |
| 2001/0029387 A1 | 10/2001 | Wolf et al. |
| 2001/0037131 A1 | 11/2001 | Schmieding et al. |
| 2001/0037153 A1 | 11/2001 | Rockwood, Jr. et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044627 A1 | 11/2001 | Justin |
| 2001/0044639 A1 | 11/2001 | Levinson |
| 2001/0047206 A1 | 11/2001 | Sklar et al. |
| 2001/0051815 A1 | 12/2001 | Esplin |
| 2001/0051816 A1 | 12/2001 | Enzerink et al. |
| 2001/0053934 A1 | 12/2001 | Schmieding |
| 2001/0056299 A1 | 12/2001 | Thompson |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | Elattrache et al. |
| 2002/0019649 A1 | 2/2002 | Sikora et al. |
| 2002/0029048 A1 | 3/2002 | Miller |
| 2002/0029066 A1 | 3/2002 | Foerster |
| 2002/0032465 A1 | 3/2002 | Lemer |
| 2002/0045902 A1 | 4/2002 | Bonutti |
| 2002/0052628 A1 | 5/2002 | Bowman |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077629 A1 | 6/2002 | Hoffman et al. |
| 2002/0077659 A1 | 6/2002 | Johnson et al. |
| 2002/0082220 A1 | 6/2002 | Hoemann et al. |
| 2002/0091391 A1 | 7/2002 | Cole et al. |
| 2002/0099411 A1 | 7/2002 | Bartlett |
| 2002/0111591 A1 | 8/2002 | McKinnon et al. |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0050667 A1 | 3/2003 | Grafton et al. |
| 2003/0065361 A1 | 4/2003 | Dreyfuss |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller, III |
| 2003/0088251 A1 | 5/2003 | Braun et al. |
| 2003/0088272 A1 | 5/2003 | Smith |
| 2003/0093156 A1 | 5/2003 | Metzger et al. |
| 2003/0105477 A1 | 6/2003 | Schwartz et al. |
| 2003/0105489 A1 | 6/2003 | Eichhorn et al. |
| 2003/0114929 A1 | 6/2003 | Knudsen et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | Mcdevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0187510 A1 | 10/2003 | Hyde |
| 2003/0195528 A1 | 10/2003 | Ritchart |
| 2003/0195564 A1 | 10/2003 | Tran et al. |
| 2003/0195565 A1 | 10/2003 | Bonutti |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1 | 12/2003 | Andrews |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0013380 A1 | 1/2004 | Jimenez |
| 2004/0015171 A1 | 1/2004 | Bojarski et al. |
| 2004/0015172 A1 | 1/2004 | Biedermann et al. |
| 2004/0024456 A1 | 2/2004 | Brown, Jr. et al. |
| 2004/0024457 A1 | 2/2004 | Boyce et al. |
| 2004/0039389 A1 | 2/2004 | West, Jr. et al. |
| 2004/0044351 A1 | 3/2004 | Searle |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0098099 A1 | 5/2004 | McCullagh et al. |
| 2004/0111117 A1 | 6/2004 | Colleran et al. |
| 2004/0122431 A1 | 6/2004 | Biedermann et al. |
| 2004/0122454 A1 | 6/2004 | Wang et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0133238 A1 | 7/2004 | Cerier |
| 2004/0133239 A1 | 7/2004 | Singhatat |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |

(56) References Cited

U.S. PATENT DOCUMENTS

| | | |
|---|---|---|
| 2004/0138747 A1 | 7/2004 | Kaladelfos |
| 2004/0138755 A1 | 7/2004 | O'connor et al. |
| 2004/0143344 A1 | 7/2004 | Malaviya et al. |
| 2004/0144535 A1 | 7/2004 | Kalman et al. |
| 2004/0147932 A1 | 7/2004 | Burkinshaw et al. |
| 2004/0147958 A1 | 7/2004 | Lam et al. |
| 2004/0148030 A1 | 7/2004 | Ek |
| 2004/0153103 A1 | 8/2004 | Schwartz et al. |
| 2004/0153153 A1 | 8/2004 | Elson et al. |
| 2004/0162579 A1* | 8/2004 | Foerster ............ A61B 17/06 606/228 |
| 2004/0166169 A1 | 8/2004 | Malaviya et al. |
| 2004/0181234 A1 | 9/2004 | Mcdevitt et al. |
| 2004/0182968 A1 | 9/2004 | Gentry |
| 2004/0187314 A1 | 9/2004 | Johnson |
| 2004/0193185 A1 | 9/2004 | Mcbrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach, III |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0021148 A1 | 1/2005 | Gibbs |
| 2005/0027307 A1 | 2/2005 | Schwartz et al. |
| 2005/0033289 A1 | 2/2005 | Warren et al. |
| 2005/0033362 A1 | 2/2005 | Grafton |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer, Jr. |
| 2005/0064042 A1 | 3/2005 | Vunjak-novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | Mcdevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0107882 A1 | 5/2005 | Stone et al. |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0130301 A1 | 6/2005 | Mckay et al. |
| 2005/0131413 A1 | 6/2005 | O'driscoll et al. |
| 2005/0137600 A1 | 6/2005 | Jacobs et al. |
| 2005/0137624 A1* | 6/2005 | Fallman ............ A61B 17/0487 606/213 |
| 2005/0143734 A1 | 6/2005 | Cachia et al. |
| 2005/0149033 A1 | 7/2005 | Mcguire et al. |
| 2005/0149118 A1* | 7/2005 | Koyfman ......... A61B 17/06166 606/228 |
| 2005/0149119 A1 | 7/2005 | Koyfman et al. |
| 2005/0149122 A1 | 7/2005 | Mcdevitt et al. |
| 2005/0149187 A1 | 7/2005 | Clark et al. |
| 2005/0154471 A1 | 7/2005 | Aram et al. |
| 2005/0159812 A1 | 7/2005 | Dinger, III et al. |
| 2005/0160656 A1 | 7/2005 | Safwat et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0171604 A1 | 8/2005 | Michalow |
| 2005/0177237 A1 | 8/2005 | Shappley et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192581 A1 | 9/2005 | Molz et al. |
| 2005/0192632 A1 | 9/2005 | Geissler et al. |
| 2005/0197711 A1 | 9/2005 | Cachia |
| 2005/0203620 A1 | 9/2005 | Steiner et al. |
| 2005/0209703 A1 | 9/2005 | Fell |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0229433 A1 | 10/2005 | Cachia |
| 2005/0234549 A1 | 10/2005 | Kladakis et al. |
| 2005/0240198 A1 | 10/2005 | Albertson et al. |
| 2005/0251153 A1 | 11/2005 | Sakamoto et al. |
| 2005/0251159 A1* | 11/2005 | Ewers ............ A61B 17/0487 606/153 |
| 2005/0251177 A1 | 11/2005 | Saadat et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0261642 A1 | 11/2005 | Weston |
| 2005/0267479 A1 | 12/2005 | Morgan et al. |
| 2005/0267533 A1 | 12/2005 | Gertner |
| 2005/0277939 A1 | 12/2005 | Miller, III |
| 2005/0277961 A1 | 12/2005 | Stone et al. |
| 2005/0277985 A1 | 12/2005 | Wert et al. |
| 2005/0283040 A1 | 12/2005 | Greenhalgh |
| 2005/0283156 A1 | 12/2005 | Schmieding et al. |
| 2005/0283158 A1 | 12/2005 | West, Jr. |
| 2005/0283192 A1 | 12/2005 | Torrie et al. |
| 2005/0283220 A1 | 12/2005 | Gobran et al. |
| 2005/0288710 A1 | 12/2005 | Fallin et al. |
| 2006/0004364 A1 | 1/2006 | Green et al. |
| 2006/0004410 A1 | 1/2006 | Nobis et al. |
| 2006/0004460 A1 | 1/2006 | Engh et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant et al. |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089525 A1 | 4/2006 | Mamo et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |

(56) References Cited

U.S. PATENT DOCUMENTS

| | | |
|---|---|---|
| 2006/0100637 A1 | 5/2006 | Rathbun et al. |
| 2006/0106423 A1 | 5/2006 | Weisel et al. |
| 2006/0111721 A1 | 5/2006 | Puricelli |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0178701 A1 | 8/2006 | Schmieding |
| 2006/0178743 A1 | 8/2006 | Carter |
| 2006/0189993 A1 | 8/2006 | Stone |
| 2006/0190041 A1 | 8/2006 | Fallin et al. |
| 2006/0190042 A1 | 8/2006 | Stone et al. |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1* | 9/2006 | Karabey .......... A61B 17/12186 606/158 |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0241776 A1 | 10/2006 | Brown et al. |
| 2006/0241781 A1 | 10/2006 | Brown et al. |
| 2006/0247642 A1 | 11/2006 | Stone et al. |
| 2006/0253130 A1 | 11/2006 | Wolniewicz, III |
| 2006/0259048 A1 | 11/2006 | Koseki |
| 2006/0259076 A1 | 11/2006 | Burkhart |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276818 A1 | 12/2006 | Buser et al. |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0280803 A1 | 12/2006 | Kumar et al. |
| 2006/0282082 A1 | 12/2006 | Fanton et al. |
| 2006/0282083 A1 | 12/2006 | Fanton et al. |
| 2006/0282085 A1 | 12/2006 | Stone |
| 2006/0293709 A1 | 12/2006 | Bojarski et al. |
| 2007/0005068 A1 | 1/2007 | Sklar |
| 2007/0005080 A1 | 1/2007 | Wolniewicz, III et al. |
| 2007/0010857 A1* | 1/2007 | Sugimoto .......... A61B 17/0401 606/232 |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1* | 2/2007 | Ortiz .................. A61F 5/0086 606/148 |
| 2007/0032823 A1 | 2/2007 | Tegg |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0078517 A1 | 4/2007 | Engh et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0129809 A1 | 6/2007 | Meridew et al. |
| 2007/0135843 A1 | 6/2007 | Burkhart |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0162120 A1 | 7/2007 | Bouffier |
| 2007/0167926 A1 | 7/2007 | Blott et al. |
| 2007/0167950 A1 | 7/2007 | Tauro et al. |
| 2007/0173948 A1 | 7/2007 | Meridew et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | Elattrache et al. |
| 2007/0191853 A1 | 8/2007 | Stone |
| 2007/0198022 A1 | 8/2007 | Lang et al. |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225763 A1 | 9/2007 | Zwolinski et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0244565 A1 | 10/2007 | Stchur |
| 2007/0250059 A1 | 10/2007 | Weisshaupt et al. |
| 2007/0250163 A1 | 10/2007 | Cassani |
| 2007/0250175 A1 | 10/2007 | Meridew et al. |
| 2007/0255282 A1 | 11/2007 | Simonton et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0009904 A1 | 1/2008 | Bourque et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051834 A1 | 2/2008 | Mazzocca et al. |
| 2008/0051836 A1 | 2/2008 | Foerster et al. |
| 2008/0058787 A1 | 3/2008 | Gertner |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0086138 A1 | 4/2008 | Stone et al. |
| 2008/0097430 A1 | 4/2008 | Bernstein et al. |
| 2008/0103528 A1 | 5/2008 | Zirps et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0137624 A1 | 6/2008 | Silverstrim et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0147127 A1 | 6/2008 | Tipirneni et al. |
| 2008/0147187 A1 | 6/2008 | Bollinger et al. |
| 2008/0154260 A1 | 6/2008 | Hoof |
| 2008/0154314 A1 | 6/2008 | Mcdevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |

(56) References Cited

U.S. PATENT DOCUMENTS

| | | |
|---|---|---|
| 2008/0161864 A1 | 7/2008 | Beck et al. |
| 2008/0166421 A1 | 7/2008 | Buhr et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1 | 8/2008 | Koob et al. |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0217263 A1 | 9/2008 | Higgins et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0228271 A1 | 9/2008 | Stone et al. |
| 2008/0234730 A1 | 9/2008 | Cotton et al. |
| 2008/0243260 A1 | 10/2008 | Lee et al. |
| 2008/0243261 A1 | 10/2008 | Wyss et al. |
| 2008/0243262 A1 | 10/2008 | Lee |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-may |
| 2008/0269674 A1 | 10/2008 | Stone |
| 2008/0275469 A1 | 11/2008 | Fanton et al. |
| 2008/0275477 A1 | 11/2008 | Sterrett et al. |
| 2008/0281428 A1 | 11/2008 | Meyers et al. |
| 2008/0288070 A1 | 11/2008 | Lo |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018654 A1 | 1/2009 | Schmieding et al. |
| 2009/0018655 A1* | 1/2009 | Brunelle .................. A61L 27/24 623/13.19 |
| 2009/0043342 A1 | 2/2009 | Freedland |
| 2009/0054928 A1 | 2/2009 | Denham et al. |
| 2009/0062847 A1* | 3/2009 | Ken .................. A61B 17/0057 606/213 |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0084491 A1 | 4/2009 | Uthgenannt et al. |
| 2009/0099598 A1 | 4/2009 | Mcdevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0182335 A1 | 7/2009 | Struhl |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0216325 A1 | 8/2009 | May et al. |
| 2009/0228015 A1 | 9/2009 | Ellis et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0234451 A1 | 9/2009 | Manderson |
| 2009/0240251 A1 | 9/2009 | Gabele |
| 2009/0240335 A1* | 9/2009 | Arcenio .............. A61B 17/7094 623/17.16 |
| 2009/0241497 A1 | 10/2009 | Imai et al. |
| 2009/0248091 A1 | 10/2009 | Teague et al. |
| 2009/0254089 A1 | 10/2009 | Tipirneni et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2009/0318965 A1 | 12/2009 | Burkhart |
| 2010/0016891 A1 | 1/2010 | Kennedy et al. |
| 2010/0016899 A1 | 1/2010 | Gelfand |
| 2010/0030321 A1 | 2/2010 | Mach |
| 2010/0042114 A1 | 2/2010 | Schaffhausen et al. |
| 2010/0063541 A1 | 3/2010 | Brunelle et al. |
| 2010/0087857 A1 | 4/2010 | Stone et al. |
| 2010/0094341 A1 | 4/2010 | Raju |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0145384 A1 | 6/2010 | Stone et al. |
| 2010/0152752 A1 | 6/2010 | Denove et al. |
| 2010/0191319 A1 | 7/2010 | Lilburn et al. |
| 2010/0191342 A1 | 7/2010 | Byrd et al. |
| 2010/0204700 A1 | 8/2010 | Falahee |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0274282 A1 | 10/2010 | Olson |
| 2010/0292792 A1 | 11/2010 | Stone et al. |
| 2010/0298872 A1 | 11/2010 | Berndt et al. |
| 2010/0298952 A1 | 11/2010 | Busold et al. |
| 2010/0305698 A1 | 12/2010 | Metzger et al. |
| 2010/0305709 A1 | 12/2010 | Metzger et al. |
| 2010/0305710 A1 | 12/2010 | Metzger |
| 2010/0312245 A1 | 12/2010 | Tipirneni et al. |
| 2010/0312341 A1 | 12/2010 | Kaiser et al. |
| 2010/0324676 A1 | 12/2010 | Albertorio |
| 2010/0331881 A1 | 12/2010 | Hart |
| 2011/0009885 A1 | 1/2011 | Graf et al. |
| 2011/0022083 A1 | 1/2011 | Dimatteo et al. |
| 2011/0026141 A1 | 2/2011 | Barrows |
| 2011/0040387 A1 | 2/2011 | Ries et al. |
| 2011/0046733 A1 | 2/2011 | Eggli |
| 2011/0087225 A1 | 4/2011 | Fritzinger |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'oca |
| 2011/0124954 A1 | 5/2011 | Ogdahl et al. |
| 2011/0125153 A1 | 5/2011 | Tyber et al. |
| 2011/0160767 A1 | 6/2011 | Stone et al. |
| 2011/0160768 A1 | 6/2011 | Stone et al. |
| 2011/0166608 A1 | 7/2011 | Duggal et al. |
| 2011/0184227 A1 | 7/2011 | Altman et al. |
| 2011/0208239 A1 | 8/2011 | Stone et al. |
| 2011/0208240 A1 | 8/2011 | Stone et al. |
| 2011/0213367 A1 | 9/2011 | Tyber et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2011/0295284 A1 | 12/2011 | Purdue et al. |
| 2011/0319932 A1 | 12/2011 | Avelar et al. |
| 2012/0004669 A1 | 1/2012 | Overes et al. |
| 2012/0024134 A1 | 2/2012 | Dow et al. |
| 2012/0041485 A1 | 2/2012 | Kaiser et al. |
| 2012/0041486 A1 | 2/2012 | Stone et al. |
| 2012/0041496 A1 | 2/2012 | Walker |
| 2012/0042768 A1 | 2/2012 | Chou et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0089193 A1 | 4/2012 | Stone et al. |
| 2012/0095470 A1 | 4/2012 | Kaiser et al. |

(56) References Cited

U.S. PATENT DOCUMENTS

| | | |
|---|---|---|
| 2012/0109156 A1 | 5/2012 | Overes et al. |
| 2012/0116409 A1 | 5/2012 | Stone |
| 2012/0116450 A1 | 5/2012 | Mcdevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0130423 A1 | 5/2012 | Sengun et al. |
| 2012/0130492 A1 | 5/2012 | Eggli et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165864 A1 | 6/2012 | Hernandez et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0192455 A1 | 8/2012 | Hansen et al. |
| 2012/0197271 A1 | 8/2012 | Astorino et al. |
| 2012/0215257 A1 | 8/2012 | Mcdevitt et al. |
| 2012/0239159 A1 | 9/2012 | Metzger et al. |
| 2012/0245585 A1 | 9/2012 | Kaiser et al. |
| 2012/0265219 A1 | 10/2012 | Rushdy et al. |
| 2012/0265294 A1 | 10/2012 | Nishigishi |
| 2012/0271403 A1 | 10/2012 | Gries |
| 2012/0273085 A1 | 11/2012 | David et al. |
| 2012/0290002 A1 | 11/2012 | Astorino |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | Mcdevitt et al. |
| 2013/0046341 A1 | 2/2013 | Stone et al. |
| 2013/0060323 A1 | 3/2013 | Mchugo |
| 2013/0090720 A1 | 4/2013 | Mahr et al. |
| 2013/0090731 A1 | 4/2013 | Walker |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158599 A1 | 6/2013 | Hester et al. |
| 2013/0158601 A1 | 6/2013 | Stone et al. |
| 2013/0172942 A1 | 7/2013 | Lewis et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0231700 A1 | 9/2013 | Gedet et al. |
| 2013/0237997 A1 | 9/2013 | Arai et al. |
| 2013/0245761 A1 | 9/2013 | Conner et al. |
| 2013/0267956 A1 | 10/2013 | Terrill et al. |
| 2013/0274812 A1 | 10/2013 | Dell'oca |
| 2013/0289564 A1 | 10/2013 | Bernstein et al. |
| 2013/0317621 A1 | 11/2013 | Metzger et al. |
| 2013/0331742 A1 | 12/2013 | Aupperle et al. |
| 2013/0331848 A1 | 12/2013 | Kaiser et al. |
| 2014/0005754 A1 | 1/2014 | Finley et al. |
| 2014/0018804 A1 | 1/2014 | Foerster |
| 2014/0046367 A1 | 2/2014 | Stone et al. |
| 2014/0046368 A1 | 2/2014 | Kaiser et al. |
| 2014/0052179 A1 | 2/2014 | Dreyfuss et al. |
| 2014/0058436 A1 | 2/2014 | Rosenbluth et al. |
| 2014/0067081 A1 | 3/2014 | Stone |
| 2014/0081322 A1 | 3/2014 | Sengun et al. |
| 2014/0088655 A1 | 3/2014 | Stone et al. |
| 2014/0094913 A1 | 4/2014 | Berelsman et al. |
| 2014/0128985 A1 | 5/2014 | Sanders et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0336760 A1 | 11/2014 | Eggli |
| 2014/0350674 A1 | 11/2014 | Stone et al. |
| 2015/0012094 A1 | 1/2015 | Denham et al. |
| 2015/0032216 A1 | 1/2015 | Metzger et al. |
| 2015/0057665 A1 | 2/2015 | Neal et al. |
| 2015/0057757 A1 | 2/2015 | Metzger et al. |
| 2015/0066081 A1 | 3/2015 | Martin |
| 2015/0119890 A1 | 4/2015 | Kaiser et al. |
| 2015/0127051 A1 | 5/2015 | Kaiser et al. |
| 2015/0128792 A1 | 5/2015 | Zachariades et al. |
| 2015/0134000 A1 | 5/2015 | Denham et al. |
| 2015/0143981 A1 | 5/2015 | Dunker |
| 2015/0148888 A1 | 5/2015 | Milner et al. |
| 2015/0173753 A1 | 6/2015 | Spivey et al. |
| 2015/0173887 A1 | 6/2015 | Berelsman et al. |
| 2015/0257750 A1 | 9/2015 | Kaiser et al. |
| 2015/0320026 A1 | 11/2015 | Toddes |
| 2016/0000483 A1 | 1/2016 | Stone |
| 2016/0022261 A1 | 1/2016 | Stone et al. |
| 2016/0038187 A1 | 2/2016 | Mcdonnell |
| 2016/0058436 A1 | 3/2016 | Stone et al. |
| 2016/0058484 A1 | 3/2016 | Mccombs-stearnes et al. |
| 2016/0074049 A1 | 3/2016 | Russell et al. |
| 2016/0081789 A1 | 3/2016 | Denham et al. |
| 2016/0106414 A1 | 4/2016 | Stone et al. |
| 2016/0128684 A1 | 5/2016 | Stone et al. |
| 2016/0183935 A1 | 6/2016 | Stone |
| 2016/0199053 A1 | 7/2016 | Norton et al. |
| 2016/0213369 A1 | 7/2016 | Stone et al. |
| 2016/0242760 A1 | 8/2016 | Kaiser et al. |
| 2017/0014225 A1 | 1/2017 | Denham et al. |
| 2017/0020507 A1 | 1/2017 | Denham et al. |
| 2017/0020569 A1 | 1/2017 | Grant |
| 2017/0035411 A1 | 2/2017 | Kaiser et al. |
| 2017/0049557 A1 | 2/2017 | Denham et al. |
| 2017/0065278 A1 | 3/2017 | Stone |
| 2017/0071593 A1 | 3/2017 | Stone |
| 2017/0071595 A1 | 3/2017 | Stone et al. |
| 2017/0086816 A1 | 3/2017 | Norton |
| 2017/0119382 A1 | 5/2017 | Denham et al. |
| 2017/0128061 A1 | 5/2017 | Stone et al. |
| 2017/0181746 A1 | 6/2017 | Denham et al. |
| 2017/0189011 A1 | 7/2017 | Stone et al. |
| 2017/0189197 A1 | 7/2017 | Werber et al. |
| 2017/0202587 A1 | 7/2017 | Stone et al. |
| 2017/0273686 A1 | 9/2017 | Denham et al. |
| 2017/0311947 A1 | 11/2017 | Kaiser et al. |
| 2017/0319194 A1 | 11/2017 | Mayeski et al. |
| 2017/0319195 A1 | 11/2017 | Denham et al. |
| 2017/0319204 A1 | 11/2017 | Norton et al. |
| 2017/0325808 A1 | 11/2017 | Stone et al. |
| 2017/0333176 A1 | 11/2017 | Stone et al. |
| 2017/0360425 A1 | 12/2017 | Stone et al. |
| 2018/0000477 A1 | 1/2018 | Kaiser et al. |
| 2018/0014864 A1 | 1/2018 | Stone et al. |
| 2018/0020762 A1 | 1/2018 | Jamison |
| 2018/0021036 A1 | 1/2018 | Kaiser et al. |
| 2018/0021125 A1 | 1/2018 | Berelsman et al. |
| 2018/0042609 A1 | 2/2018 | Denham et al. |
| 2018/0098858 A1 | 4/2018 | Valderrabano et al. |
| 2018/0125476 A1 | 5/2018 | Kaiser et al. |
| 2018/0125477 A1 | 5/2018 | Stone |
| 2018/0153538 A1 | 6/2018 | Kaiser et al. |
| 2018/0153558 A1 | 6/2018 | Bake et al. |
| 2018/0161030 A1 | 6/2018 | Stone et al. |
| 2018/0177501 A1 | 6/2018 | Kaiser et al. |

(56) References Cited

U.S. PATENT DOCUMENTS

| | | |
|---|---|---|
| 2018/0193015 A1 | 7/2018 | Denham et al. |
| 2018/0221017 A1 | 8/2018 | Stone et al. |
| 2018/0235747 A1 | 8/2018 | Berelsman et al. |
| 2018/0249997 A1 | 9/2018 | Stone et al. |
| 2019/0083233 A1 | 3/2019 | Denham et al. |
| 2019/0150909 A1 | 5/2019 | Stone et al. |
| 2019/0150923 A1 | 5/2019 | Stone et al. |
| 2019/0231348 A1 | 8/2019 | Stone et al. |
| 2019/0254652 A1 | 8/2019 | Stone et al. |
| 2019/0274681 A1 | 9/2019 | Denham et al. |
| 2019/0282227 A1 | 9/2019 | Norton |
| 2019/0290258 A1 | 9/2019 | Denham et al. |
| 2019/0298345 A1 | 10/2019 | Denham et al. |
| 2019/0328382 A1 | 10/2019 | Stone et al. |
| 2019/0365376 A1 | 12/2019 | Stone et al. |
| 2020/0029955 A1 | 1/2020 | Stone et al. |
| 2020/0085562 A1 | 3/2020 | Stone et al. |
| 2020/0178959 A1 | 6/2020 | Denham et al. |
| 2020/0187932 A1 | 6/2020 | Kaiser et al. |
| 2020/0187933 A1 | 6/2020 | Kaiser et al. |
| 2020/0197002 A1 | 6/2020 | Stone et al. |
| 2020/0297338 A1 | 9/2020 | Stone et al. |

FOREIGN PATENT DOCUMENTS

| | | | |
|---|---|---|---|
| AU | 4381268 | A | 4/1970 |
| AU | 5850469 | A | 1/1971 |
| AU | 5963869 | A | 2/1971 |
| AU | 1505470 | A | 11/1971 |
| AU | 2223767 | A | 5/1973 |
| AU | 3615171 | A | 5/1973 |
| AU | 440266 | B2 | 9/1973 |
| AU | 5028569 | A | 9/1973 |
| AU | 7110887 | A | 10/1987 |
| AU | 639410 | A | 11/1989 |
| AU | 1713188 | A | 11/1989 |
| AU | 651929 | B2 | 8/1994 |
| AU | 3877493 | B2 | 8/1994 |
| BE | 1010569 | A6 | 10/1998 |
| CN | 1720872 | A | 1/2006 |
| CN | 1777450 | A | 5/2006 |
| CN | 101083954 | A | 12/2007 |
| CN | 101584592 | A | 11/2009 |
| CN | 105208970 | A | 12/2015 |
| DE | 2529669 | A1 | 3/1976 |
| DE | 2747312 | A1 | 4/1979 |
| DE | 2818254 | A1 | 10/1979 |
| DE | 2919009 | A1 | 11/1979 |
| DE | 3027138 | A1 | 12/1981 |
| DE | 3225620 | A1 | 2/1983 |
| DE | 3136083 | A1 | 3/1983 |
| DE | 233303 | A1 | 2/1986 |
| DE | 4127550 | A1 | 2/1993 |
| DE | 4302397 | A | 7/1993 |
| DE | 29621340 | U1 | 4/1998 |
| DE | 19841252 | A1 | 3/2000 |
| DE | 29922088 | U1 | 4/2000 |
| DE | 20207781 | U1 | 8/2002 |
| EP | 0019062 | A1 | 11/1980 |
| EP | 0108912 | A2 | 5/1984 |
| EP | 0129422 | A2 | 12/1984 |
| EP | 0129442 | A1 | 12/1984 |
| EP | 0172130 | A2 | 2/1986 |
| EP | 0241240 | A2 | 10/1987 |
| EP | 0241792 | A1 | 10/1987 |
| EP | 0260970 | A2 | 3/1988 |
| EP | 0270704 | A1 | 6/1988 |
| EP | 0282789 | A2 | 9/1988 |
| EP | 0315371 | A2 | 5/1989 |
| EP | 0317406 | A1 | 5/1989 |
| EP | 0340159 | A1 | 11/1989 |
| EP | 0346183 | A1 | 12/1989 |
| EP | 0349173 | A1 | 1/1990 |
| EP | 0374088 | A1 | 6/1990 |
| EP | 0409364 | A2 | 1/1991 |
| EP | 0415915 | A1 | 3/1991 |
| EP | 0440991 | A1 | 8/1991 |
| EP | 0441065 | A2 | 8/1991 |
| EP | 0447065 | A2 | 9/1991 |
| EP | 0451932 | A1 | 10/1991 |
| EP | 0464480 | A1 | 1/1992 |
| EP | 0490417 | A1 | 6/1992 |
| EP | 0497079 | A1 | 8/1992 |
| EP | 0502509 | A1 | 9/1992 |
| EP | 0502698 | A1 | 9/1992 |
| EP | 0520177 | A1 | 12/1992 |
| EP | 520177 | A1 | 12/1992 |
| EP | 0546726 | A1 | 6/1993 |
| EP | 0552950 | A1 | 7/1993 |
| EP | 0574707 | A1 | 12/1993 |
| EP | 0582514 | A1 | 2/1994 |
| EP | 0591991 | A2 | 4/1994 |
| EP | 0598219 | A2 | 5/1994 |
| EP | 0611551 | A1 | 8/1994 |
| EP | 0627203 | A2 | 12/1994 |
| EP | 0651979 | A1 | 5/1995 |
| EP | 0669110 | A2 | 8/1995 |
| EP | 0686373 | A1 | 12/1995 |
| EP | 0702933 | A1 | 3/1996 |
| EP | 0775473 | A1 | 5/1997 |
| EP | 0913123 | A1 | 5/1999 |
| EP | 0913131 | A2 | 5/1999 |
| EP | 0995409 | A1 | 4/2000 |
| EP | 1013229 | A2 | 6/2000 |
| EP | 1093773 | A1 | 4/2001 |
| EP | 1093774 | A1 | 4/2001 |
| EP | 1555945 | A2 | 7/2005 |
| EP | 1741412 | A2 | 1/2007 |
| EP | 1864617 | A2 | 12/2007 |
| EP | 2238944 | A2 | 10/2010 |
| EP | 2544607 | A1 | 1/2013 |
| EP | 2709557 | A1 | 3/2014 |
| EP | 2895112 | A1 | 7/2015 |
| EP | 2934379 | A1 | 10/2015 |
| EP | 2434987 | B1 | 6/2016 |
| EP | 2775935 | B1 | 5/2017 |
| FR | 2622790 | A1 | 5/1989 |
| FR | 2634373 | A1 | 1/1990 |
| FR | 2655840 | A1 | 6/1991 |
| FR | 2663837 | A1 | 1/1992 |
| FR | 2682867 | A1 | 4/1993 |
| FR | 2687911 | A1 | 9/1993 |
| FR | 2688689 | A1 | 9/1993 |
| FR | 2704140 | A3 | 10/1994 |
| FR | 2717070 | A1 | 9/1995 |
| FR | 2723528 | A1 | 2/1996 |
| FR | 2734709 | A1 | 12/1996 |
| FR | 2744010 | A1 | 8/1997 |
| FR | 2745999 | A1 | 9/1997 |
| FR | 2770764 | A1 | 5/1999 |
| GB | 401677 | A | 11/1933 |
| GB | 1413477 | A | 11/1975 |
| GB | 1485681 | A | 9/1977 |
| GB | 2083751 | A | 3/1982 |
| GB | 2118474 | A | 11/1983 |
| GB | 2129306 | A | 5/1984 |
| GB | 2227175 | A | 7/1990 |
| GB | 2253147 | A | 9/1992 |
| GB | 2312376 | A | 10/1997 |
| GB | 2403416 | A | 1/2005 |
| GB | 2454251 | A | 5/2009 |
| JP | 5362911 | U | 5/1978 |
| JP | 5362912 | U | 5/1978 |
| JP | 5374942 | U | 6/1978 |
| JP | 5378230 | U | 6/1978 |
| JP | 54166092 | U | 11/1979 |
| JP | 54166093 | U | 11/1979 |
| JP | 54176284 | U | 12/1979 |
| JP | 54178988 | U | 12/1979 |
| JP | 5362911 | A | 7/1987 |
| JP | 62159647 | A | 7/1987 |
| JP | 62159647 | U | 10/1987 |
| JP | 62295657 | A | 12/1987 |
| JP | 5269160 | A | 10/1993 |

(56) References Cited

FOREIGN PATENT DOCUMENTS

| | | |
|---|---|---|
| JP | 5300917 A | 11/1993 |
| JP | 751292 A | 2/1995 |
| JP | 10127672 A | 5/1998 |
| JP | 10211213 A | 8/1998 |
| JP | 5362911 B2 | 12/2013 |
| JP | 5362912 B2 | 12/2013 |
| JP | 5374942 B2 | 12/2013 |
| JP | 5378230 B2 | 12/2013 |
| RU | 2051647 C1 | 1/1996 |
| RU | 2076667 C1 | 4/1997 |
| WO | WO-8300615 A1 | 3/1983 |
| WO | WO-8603666 A1 | 7/1986 |
| WO | WO-8701270 A1 | 3/1987 |
| WO | WO-8901767 A1 | 3/1989 |
| WO | WO-8909030 A1 | 10/1989 |
| WO | WO-8910096 A1 | 11/1989 |
| WO | WO-9008510 A1 | 8/1990 |
| WO | WO-9203980 A1 | 3/1992 |
| WO | WO-9314705 A1 | 8/1993 |
| WO | WO-9315694 A1 | 8/1993 |
| WO | WO-9502373 A1 | 1/1995 |
| WO | WO-9503003 A1 | 2/1995 |
| WO | WO-9529637 A1 | 11/1995 |
| WO | WO-9532670 A1 | 12/1995 |
| WO | WO-9609797 A1 | 4/1996 |
| WO | WO-9629029 A1 | 9/1996 |
| WO | WO-9737603 A1 | 10/1997 |
| WO | WO-9812991 A1 | 4/1998 |
| WO | WO-9812992 A1 | 4/1998 |
| WO | WO-9822047 A1 | 5/1998 |
| WO | WO-9822048 A1 | 5/1998 |
| WO | WO-9901084 A2 | 1/1999 |
| WO | WO-9912480 A1 | 3/1999 |
| WO | WO-9937219 A1 | 7/1999 |
| WO | WO-9944544 A1 | 9/1999 |
| WO | WO-9952472 A1 | 10/1999 |
| WO | WO-0004159 A1 | 1/2000 |
| WO | WO-0040159 A1 | 7/2000 |
| WO | WO-0139671 A1 | 6/2001 |
| WO | WO-0236020 A1 | 5/2002 |
| WO | WO-03005914 A1 | 1/2003 |
| WO | WO-03071962 A2 | 9/2003 |
| WO | WO-03077772 A1 | 9/2003 |
| WO | WO-03092551 A1 | 11/2003 |
| WO | WO-2004091412 A1 | 10/2004 |
| WO | WO-05104992 A1 | 11/2005 |
| WO | WO-2005122954 A1 | 12/2005 |
| WO | WO-2006011786 A1 | 2/2006 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009083047 A1 | 7/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014043078 A1 | 3/2014 |
| WO | WO-2014100109 A1 | 6/2014 |
| WO | WO-2014151766 A1 | 9/2014 |

OTHER PUBLICATIONS

"U.S. Appl. No. 14/876,167, Final Office Action dated Jul. 31, 2018", 8 pgs.

"U.S. Appl. No. 14/876,167, Response filed Sep. 28, 2018 to Final Office Action dated Jul. 31, 2018", 10 pgs.

"U.S. Appl. No. 14/936,831, Response filed Aug. 16, 2018 to Non Final Office Action dated May 16, 2018", 9 pgs.

"U.S. Appl. No. 14/983,108, Final Office Action dated Aug. 30, 2018", 9 pgs.

"U.S. Appl. No. 14/983,108, Response filed Jun. 13, 2018 to Non Final Office Action dated Apr. 10, 2018", 10 pgs.

"U.S. Appl. No. 14/983,747, Notice of Allowance dated Sep. 24, 2018", 14 ogs.

"U.S. Appl. No. 14/983,747, Response filed Jun. 13, 2018 to Non Final Office Action dated Apr. 9, 2018", 9 pgs.

"U.S. Appl. No. 15/131,663, Non Final Office Action dated Oct. 2, 2018", 7 pgs.

"U.S. Appl. No. 15/131,663, Response filed Jul. 13, 208 to Restriction Requirement dated May 18, 2018", 8 pgs.

"U.S. Appl. No. 15/166,480, Notice of Allowance dated Sep. 20, 2018", 12 pgs.

"U.S. Appl. No. 15/166,480, Response filed Jul. 18, 2018 to Restriction Requirement dated May 21, 2018", 6 pgs.

"U.S. Appl. No. 15/200,546, Response Filed Sep. 17, 2018 to Restriction Requirement dated Jul. 16, 2018", 8 pgs.

"U.S. Appl. No. 15/200,546, Restriction Requirement dated Jul. 16, 2018", 6 pgs.

"U.S. Appl. No. 15/278,777, Notice of Allowance dated Jul. 15, 2018", 8 pgs.

"U.S. Appl. No. 15/288,183, Restriction Requirement dated Sep. 12, 2018", 6 pgs.

"U.S. Appl. No. 15/294,994, Non Final Office Action dated Aug. 9, 2018", 9 pgs.

"U.S. Appl. No. 15/297,844, Notice of Allowance dated Aug. 30, 2018", 10 pgs.

"U.S. Appl. No. 15/461,675, Supplemental Preliminary Amendment filed Jun. 28, 2018", 7 pgs.

"U.S. Appl. No. 15/722,002, Preliminary Amendment filed Jun. 29, 2018", 5 pgs.

"European Application Serial No. 16168202.6, Response filed Sep. 5, 2018 to Communication Pursuant to Article 94(3) EPC dated Apr. 25, 2018", 13 pgs.

"U.S. Appl. No. 14/876,167, Notice of Allowance dated Dec. 10, 2018", 8 pgs.

"U.S. Appl. No. 14/936,831, Advisory Action dated Jan. 29, 2019", 3 pgs.

"U.S. Appl. No. 14/936,831, Final Office Action dated Nov. 20, 2018", 8 pgs.

"U.S. Appl. No. 14/936,831, Response filed Jan. 21, 2019 to Final Office Action dated Nov. 20, 2018", 9 pgs.

"U.S. Appl. No. 14/983,108, Non Final Office Action dated Nov. 5, 2018", 8 pgs.

"U.S. Appl. No. 14/983,108, Response filed Feb. 4, 2019 to Non Final Office Action dated Nov. 5, 2018", 8 pgs.

"U.S. Appl. No. 14/983,108, Response filed Oct. 22, 2018 to Final Office Action dated Aug. 30, 2018", 9 pgs.

"U.S. Appl. No. 15/060,007, Final Office Action dated Jan. 3, 2019", 9 pgs.

"U.S. Appl. No. 15/060,007, Non Final Office Action dated Nov. 9, 2018", 17 pgs.

"U.S. Appl. No. 15/060,007, Response filed Nov. 26, 2018 to Non Final Office Action dated Nov. 9, 2018", 10 pgs.

"U.S. Appl. No. 15/131,663, Response Filed Jan. 2, 2019 to Non-Final Office Action dated Oct. 2, 2018", 9 pgs.

"U.S. Appl. No. 15/200,546, Non Final Office Action dated Oct. 15, 2018", 10 pgs.

"U.S. Appl. No. 15/200,546, Response Filed Jan. 15, 2019 to Non-Final Office Action dated Oct. 15, 2018", 10 pgs.

(56) References Cited

OTHER PUBLICATIONS

"U.S. Appl. No. 15/288,183, Non Final Office Action dated Dec. 10, 2018", 13 pgs.
"U.S. Appl. No. 15/288,183, Response filed Oct. 25, 2018 to Restriction Requirement dated Sep. 12, 2018", 7 pgs.
"U.S. Appl. No. 15/294,994, Final Office Action dated Jan. 25, 2019", 13 pgs.
"U.S. Appl. No. 15/294,994, Response filed Oct. 25, 2018 to Non Final Office Action dated Aug. 9, 2018", 10 pgs.
"U.S. Appl. No. 15/332,590, Notice of Allowance dated Dec. 5, 2018", 13 pgs.
"U.S. Appl. No. 15/361,917, Restriction Requirement dated Jan. 3, 2019", 6 pgs.
"U.S. Appl. No. 16/160,559, Preliminary Amendment filed Oct. 17, 2018", 6 pgs.
"U.S. Appl. No. 16/251,342, Preliminary Amendment filed Jan. 21, 2019", 6 pgs.
"U.S. Appl. No. 16/255,300, Preliminary Amendment filed Jan. 24, 2019", 6 pgs.
"European Application Serial No. 16168202.6, Communication pursuant to Article 94(3) EPC dated Dec. 11, 2018", 6 pgs.
"European Application Serial No. 17169003.5, Response Filed Dec. 19, 2018 to Extended European Search Report dated May 11, 2018", 22 pgs.
"U.S. Appl. No. 14/936,831, Notice of Allowance dated Jul. 3, 2019", 8 pgs.
"U.S. Appl. No. 15/288,183, Corrected Notice of Allowability dated Jun. 21, 2019", 7 pgs.
"U.S. Appl. No. 15/361,917, Final Office Action dated Sep. 3, 2019", 8 pgs.
"U.S. Appl. No. 15/361,917, Response filed Jun. 19, 2019 to Non Final Office Action dated Apr. 19, 2019", 9 pgs.
"U.S. Appl. No. 15/401,768, Non Final Office Action dated Jul. 22, 2019", 10 pgs.
"U.S. Appl. No. 15/401,768, Response filed Aug. 28, 2019 to Non Final Office Action dated Jul. 22, 2019", 10 pgs.
"U.S. Appl. No. 15/412,676, Non Final Office Action dated Jul. 21, 2019", 11 pgs.
"U.S. Appl. No. 15/455,895, Non Final Office Action dated Sep. 5, 2019", 11 pgs.
"U.S. Appl. No. 15/455,895, Supplemental Preliminary Amendment filed May 24, 2019", 6 pgs.
"U.S. Appl. No. 15/461,675, Non Final Office Action dated Aug. 9, 2019", 10 pgs.
"U.S. Appl. No. 15/622,718, Non Final Office Action dated Aug. 28, 2019", 14 pgs.
"U.S. Appl. No. 15/622,718, Response filed Jul. 31, 2019 to Restriction Requirement dated Jun. 7, 2019", 8 pgs.
"U.S. Appl. No. 15/622,718, Restriction Requirement dated Jun. 7, 2019", 6 pgs.
"U.S. Appl. No. 15/626,384, Notice of Allowance dated Jun. 7, 2019", 7 pgs.
"U.S. Appl. No. 15/626,384, Response filed Jul. 31, 2019 to Non-Final Office Action dated May 3, 2019", 13 pgs.
"U.S. Appl. No. 15/654,386, Response filed Aug. 23, 2019 to Restriction Requirement dated Jul. 16, 2019", 9 pgs.
"U.S. Appl. No. 15/654,386, Restriction Requirement dated Jul. 16, 2019", 6 pgs.
"U.S. Appl. No. 15/662,572, Response filed Aug. 23, 2019 to Restriction Requirement dated Jul. 1, 2019", 8 pgs.
"U.S. Appl. No. 15/662,572, Restriction Requirement dated Jul. 1, 2019", 6 pgs.
"U.S. Appl. No. 15/664,572, Notice of Allowance dated Jun. 12, 2019", 8 pgs.
"U.S. Appl. No. 15/682,187, Response filed Sep. 18, 2019 to Restriction Requirement dated Aug. 9, 2019", 7 pgs.
"U.S. Appl. No. 15/682,187, Restriction Requirement dated Aug. 9, 2019", 6 pgs.
"U.S. Appl. No. 15/703,727, Non Final Office Action dated Aug. 1, 2019", 11 pgs.
"U.S. Appl. No. 15/715,731, Restriction Requirement dated Sep. 4, 2019", 6 pgs.
"U.S. Appl. No. 15/720,997, Non Final Office Action dated Jul. 16, 2019", 11 pgs.
"U.S. Appl. No. 15/722,002, Restriction Requirement dated Sep. 17, 2019", 6 pgs.
"U.S. Appl. No. 15/793,216, Non Final Office Action dated Aug. 1, 2019", 21 pgs.
"U.S. Appl. No. 15/865,938, Notice of Allowance dated Sep. 17, 2019", 11 pgs.
"U.S. Appl. No. 16/420,676, Preliminary Amendment filed Jun. 3, 2019", 5 pgs.
"U.S. Appl. No. 16/428,277, Preliminary Amendment filed Jun. 3, 2019", 5 pgs.
"U.S. Appl. No. 16/436,023, Preliminary Amendment filed Jun. 12, 2019", 6 pgs.
"U.S. Appl. No. 16/443,391, Preliminary Amendment filed Jun. 19, 2019", 6 pgs.
"U.S. Appl. No. 16/508,764, Preliminary Amendment filed Jul. 12, 2019", 7 pgs.
"U.S. Appl. No. 16/544,293, Preliminary Amendment filed Aug. 21, 2019", 7 pgs.
"U.S. Appl. No. 14/983,108, Notice of Allowance dated Mar. 8, 2019", 8 pgs.
"U.S. Appl. No. 15/060,007, Corrected Notice of Allowability dated May 1, 2019", 2 pgs.
"U.S. Appl. No. 15/060,007, Notice of Allowance dated Mar. 6, 2019", 5 pgs.
"U.S. Appl. No. 15/060,007, Response filed Feb. 15, 2019 to Final Office Action dated Jan. 3, 2019", 9 pgs.
"U.S. Appl. No. 15/131,663, Notice of Allowance dated Mar. 19, 2019", 8 pgs.
"U.S. Appl. No. 15/200,546, Notice of Allowance dated Mar. 19, 2019", 7 pgs.
"U.S. Appl. No. 15/288,183, Notice of Allowance dated May 9, 2019", 11 pgs.
"U.S. Appl. No. 15/288,183, Response filed Feb. 27, 2019 to Non Final Office Action dated Dec. 10, 2018", 11 pgs.
"U.S. Appl. No. 15/294,994, Examiner Interview Summary dated Feb. 26, 2019", 3 pgs.
"U.S. Appl. No. 15/294,994, Notice of Allowance dated May 22, 2019", 10 pgs.
"U.S. Appl. No. 15/294,994, Response filed Feb. 27, 2019 to Final Office Action dated Jan. 25, 2019", 9 pgs.
"U.S. Appl. No. 15/361,917, Non Final Office Action dated Apr. 19, 2019", 11 pgs.
"U.S. Appl. No. 15/361,917, Response filed Feb. 14, 2019 to Restriction Requirement dated Jan. 3, 2019", 6 pgs.
"U.S. Appl. No. 15/401,768, Response filed May 15, 2019 to Restriction Requirement dated Mar. 15, 2019", 7 pgs.
"U.S. Appl. No. 15/401,768, Restriction Requirement dated Mar. 15, 2019", 6 pgs.
"U.S. Appl. No. 15/412,676, Response filed May 15, 2019 to Restriction Requirement dated Mar. 15, 2019", 7 pgs.
"U.S. Appl. No. 15/412,676, Restriction Requirement dated Mar. 15, 2019", 6 pgs.
"U.S. Appl. No. 15/461,675, Response filed May 24, 2019 to Restriction Requirement dated Mar. 26, 2019", 6 pgs.
"U.S. Appl. No. 15/461,675, Restriction Requirement dated Mar. 26, 2019", 6 pgs.
"U.S. Appl. No. 15/626,384, Non Final Office Action dated May 3, 2019", 14 pgs.
"U.S. Appl. No. 15/664,572, Non Final Office Action dated May 15, 2019", 8 pgs.
"U.S. Appl. No. 15/664,572, Response filed May 17, 2019 to Non Final Office Action dated May 15, 2019", 9 pgs.
"U.S. Appl. No. 16/380,742, Preliminary Amendment filed Apr. 12, 2019", 6 pgs.
"U.S. Appl. No. 16/400,199, Preliminary Amendment filed May 7, 2019", 7 pgs.
"Information of Polydioxanone", Dolphin Sutures, [Online] Retrieved from the internet: <https://www.dolphinsutures.com/resoucres/information-on-polydioxanone>, (2018), 2 pgs.

(56) References Cited

OTHER PUBLICATIONS

"U.S. Appl. No. 15/361,917, Advisory Action dated Nov. 19, 2019", 3 pgs.
"U.S. Appl. No. 15/361,917, Notice of Allowance dated Mar. 4, 2020", 8 pgs.
"U.S. Appl. No. 15/361,917, Response filed Nov. 4, 2019 to Final Office Action dated Sep. 3, 2019", 8 pgs.
"U.S. Appl. No. 15/401,768, Notice of Allowance dated Nov. 20, 2019", 9 pgs.
"U.S. Appl. No. 15/412,676, Notice of Allowance dated Dec. 30, 2019", 8 pgs.
"U.S. Appl. No. 15/412,676, Response filed Oct. 23, 2019 to Non Final Office Action dated Jul. 23, 2019", 12 pgs.
"U.S. Appl. No. 15/455,895, Examiner Interview Summary dated Nov. 25, 2019", 3 pgs.
"U.S. Appl. No. 15/455,895, Notice of Allowance dated Feb. 13, 2020", 7 pgs.
"U.S. Appl. No. 15/455,895, Response filed Jan. 28, 2020 to Non Final Office Action dated Sep. 5, 2019", 14 pgs.
"U.S. Appl. No. 15/461,675, Notice of Allowance dated Jan. 30, 2020", 7 pgs.
"U.S. Appl. No. 15/461,675, Response filed Nov. 12, 2019 to Non Final Office Action dated Aug. 9, 2019", 11 pgs.
"U.S. Appl. No. 15/622,718, Examiner Interview Summary dated Nov. 22, 2019", 3 pgs.
"U.S. Appl. No. 15/622,718, Notice of Allowance dated Feb. 13, 2020", 8 pgs.
"U.S. Appl. No. 15/622,718, Response filed Jan. 28, 2020 to Non Final Office Action dated Aug. 28, 2019", 11 pgs.
"U.S. Appl. No. 15/626,384, Notice of Allowability dated Oct. 18, 2019", 2 pgs.
"U.S. Appl. No. 15/654,386, Non Final Office Action dated Nov. 7, 2019", 10 pgs.
"U.S. Appl. No. 15/654,386, Notice of Allowance dated Feb. 20, 2020", 8 pgs.
"U.S. Appl. No. 15/654,386, Response filed Feb. 5, 2020 to Non Final Office Action dated Nov. 7, 2019", 12 pgs.
"U.S. Appl. No. 15/662,572, Non Final Office Action dated Oct. 10, 2019", 14 pgs.
"U.S. Appl. No. 15/662,572, Notice of Allowance dated Mar. 11, 2020", 9 pgs.
"U.S. Appl. No. 15/662,572, Response filed Jan. 8, 2020 to Non Final Office Action dated Oct. 10, 2019", 10 pgs.
"U.S. Appl. No. 15/682,187, Non Final Office Action dated Dec. 16, 2019", 10 pgs.
"U.S. Appl. No. 15/682,187, Notice of Allowance dated Mar. 25, 2020", 9 pgs.
"U.S. Appl. No. 15/682,187, Response filed Feb. 27, 2020 to Non Final Office Action dated Dec. 16, 2019", 11 pgs.
"U.S. Appl. No. 15/703,727, Notice of Allowance dated Nov. 20, 2019", 7 pgs.
"U.S. Appl. No. 15/703,727, Response filed Nov. 1, 2019 to Non Final Office Action dated Aug. 1, 2019", 10 pgs.
"U.S. Appl. No. 15/715,731, Non Final Office Action dated Jan. 21, 2020", 8 pgs.
"U.S. Appl. No. 15/715,731, Notice of Allowance dated Apr. 8, 2020", 9 pgs.
"U.S. Appl. No. 15/715,731, Response filed Feb. 27, 2020 to Non Final Office Action dated Jan. 21, 2020", 12 pgs.
"U.S. Appl. No. 15/715,731, Response Filed Nov. 4, 2019 to Restriction Requirement dated Sep. 4, 2019", 9 pgs.
"U.S. Appl. No. 15/720,997, Non Final Office Action dated Jan. 6, 2020", 10 pgs.
"U.S. Appl. No. 15/720,997, Response filed Mar. 27, 2020 to Non Final Office Action dated Jan. 6, 2020", 10 pgs.
"U.S. Appl. No. 15/720,997, Response filed Oct. 3, 2019 to Non-Final Office Action dated Jul. 16, 2019", 9 pgs.
"U.S. Appl. No. 15/722,002, Non Final Office Action dated Feb. 4, 2020", 8 pgs.
"U.S. Appl. No. 15/722,002, Notice of Allowance dated Apr. 8, 2020", 7 pgs.
"U.S. Appl. No. 15/722,002, Response filed Mar. 5, 2020 to Non Final Office Action dated Feb. 4, 2020", 7 pgs.
"U.S. Appl. No. 15/722,002, Response filed Nov. 14, 2019 to Restriction Requirement dated Sep. 17, 2019", 6 pgs.
"U.S. Appl. No. 15/793,216, Examiner Interview Summary dated Nov. 4, 2019", 4 pgs.
"U.S. Appl. No. 15/793,216, Notice of Allowance dated Mar. 23, 2020", 7 pgs.
"U.S. Appl. No. 15/793,216, Response filed Jan. 28, 2020 to Non Final Office Action dated Aug. 1, 2019", 13 pgs.
"U.S. Appl. No. 15/866,089, Final Office Action dated Mar. 25, 2020", 15 pgs.
"U.S. Appl. No. 15/866,089, Non Final Office Action dated Dec. 4, 2019", 16 pgs.
"U.S. Appl. No. 15/866,089, Response filed Feb. 27, 2020 to Non Final Office Action dated Dec. 4, 2019", 10 pgs.
"U.S. Appl. No. 15/866,089, Response filed Jun. 18, 2020 to Final Office Action dated Mar. 25, 2020", 11 pgs.
"U.S. Appl. No. 15/886,712, Non Final Office Action dated Sep. 27, 2019", 8 pgs.
"U.S. Appl. No. 15/886,712, Notice of Allowance dated Nov. 14, 2019", 7 pgs.
"U.S. Appl. No. 15/886,712, Response filed Oct. 18, 2019 to Non Final Office Action dated Sep. 27, 2019", 9 pgs.
"U.S. Appl. No. 15/891,049, Response filed May 29, 2020 to Restriction Requirement dated May 5, 2020", 9 pgs.
"U.S. Appl. No. 15/891,049, Restriction Requirement dated May 5, 2020", 6 pgs.
"U.S. Appl. No. 15/891,049, Supplemental Preliminary Amendment filed Dec. 20, 2019", 8 pgs.
"U.S. Appl. No. 15/903,261, Notice of Allowance dated Mar. 26, 2020", 9 pgs.
"U.S. Appl. No. 15/917,143, Response filed Jun. 17, 2020 to Restriction Requirement dated May 5, 2020", 8 pgs.
"U.S. Appl. No. 15/917,143, Restriction Requirement dated May 5, 2020", 6 pgs.
"U.S. Appl. No. 15/945,425, Restriction Requirement dated May 19, 2020", 7 pgs.
"U.S. Appl. No. 16/593,022, Preliminary Amendment filed Oct. 30, 2019", 8 pgs.
"U.S. Appl. No. 16/593,022, Supplemental Preliminary Amendment filed Dec. 5, 2019", 8 pgs.
"U.S. Appl. No. 16/593,022, Supplemental Preliminary Amendment filed Dec. 20, 2019", 5 pgs.
"U.S. Appl. No. 16/690,671, Preliminary Amendment filed Dec. 11, 2019", 7 pgs.
"U.S. Appl. No. 16/795,181, Preliminary Amendment filed Feb. 20, 2020", 6 pgs.
"U.S. Appl. No. 16/802,228, Preliminary Amendment filed Mar. 4, 2020", 7 pgs.
"U.S. Appl. No. 16/802,248, Preliminary Amendment filed Mar. 5, 2020", 8 pgs.
"U.S. Appl. No. 16/806,611, Preliminary Amendment filed Mar. 4, 2020", 7 pgs.
"U.S. Appl. No. 16/895,246, Preliminary Amendment filed Jun. 9, 2020", 6 pgs.
"AperFix® System Surgical Technique Guide. Single Tunnel Double Bundle.™", Cayenne Medical brochure, (Aug. 2008), 8 pgs.
"U.S. Appl. No. 10/984,624, Final Office Action dated Jan. 6, 2009", 9 pgs.
"U.S. Appl. No. 10/984,624, Non Final Office Action dated Jul. 10, 2008", 9 pgs.
"U.S. Appl. No. 10/984,624, Notice of Allowance dated Jun. 12, 2009", 9 pgs.
"U.S. Appl. No. 10/984,624, Response filed Apr. 1, 2009 to Final Office Action dated Jan. 5, 2009", 16 pgs.
"U.S. Appl. No. 10/984,624, Response filed Apr. 15, 2008 to Restriction Requirement dated Mar. 24, 2008", 1 pg.
"U.S. Appl. No. 10/984,624, Response filed Oct. 10, 2008 to Non Final Office Action dated Jul. 10, 2008", 12 pgs.

(56) References Cited

OTHER PUBLICATIONS

"U.S. Appl. No. 10/984,624, Restriction Requirement dated Mar. 24, 2008", 5 pgs.
"U.S. Appl. No. 11/294,694, Final Office Action dated Sep. 1, 2010", 14 pgs.
"U.S. Appl. No. 11/294,694, Non Final Office Action dated Mar. 15, 2010", 19 pgs.
"U.S. Appl. No. 11/294,694, Notice of Allowance dated Nov. 17, 2010", 4 pgs.
"U.S. Appl. No. 11/294,694, Preliminary Amendment filed Jan. 13, 2010", 9 pgs.
"U.S. Appl. No. 11/294,694, Response filed Jun. 15, 2010 to Non Final Office Action dated Mar. 16, 2010", 16 pgs.
"U.S. Appl. No. 11/294,694, Response filed Nov. 1, 2010 to Final Office Action dated Sep. 1, 2010", 10 pgs.
"U.S. Appl. No. 11/294,694, Response filed Dec. 22, 2009 to Restriction Requirement dated Nov. 25, 2009", 1 pg.
"U.S. Appl. No. 11/294,694, Restriction Requirement dated Nov. 25, 2009", 9 pgs.
"U.S. Appl. No. 11/347,661, Examiner Interview Summary dated Sep. 11, 2009", 2 pgs.
"U.S. Appl. No. 11/347,661, Final Office Action dated Mar. 3, 2009", 15 pgs.
"U.S. Appl. No. 11/347,661, Non Final Office Action dated Aug. 13, 2009", 19 pgs.
"U.S. Appl. No. 11/347,661, Non Final Office Action dated Aug. 21, 2008", 11 pgs.
"U.S. Appl. No. 11/347,661, Notice of Allowance dated Feb. 24, 2010", 8 pgs.
"U.S. Appl. No. 11/347,661, Notice of Allowance dated May 5, 2010", 8 pgs.
"U.S. Appl. No. 11/347,661, Response filed May 29, 2008 to Restriction Requirement dated Apr. 30, 2008", 1 pg.
"U.S. Appl. No. 11/347,661, Response filed Jun. 3, 2009 to Final Office Action dated Mar. 3, 2009", 19 pgs.
"U.S. Appl. No. 11/347,661, Response filed Nov. 6, 2009 to Non Final Office Action dated Aug. 13, 2009", 16 pgs.
"U.S. Appl. No. 11/347,661, Response filed Nov. 19, 2008 to Non Final Office Action dated Aug. 21, 2008", 12 pgs.
"Application U.S. Appl. No. 11/347,661, Restriction Requirement dated Apr. 30, 2008", 6 pgs.
"U.S. Appl. No. 11/347,662, Examiner Interview Summary dated Jun. 24, 2010", 3 pgs.
"U.S. Appl. No. 11/347,662, Examiner Interview Summary dated Nov. 9, 2009", 3 pgs.
"U.S. Appl. No. 11/347,662, Final Office Action dated Sep. 16, 2009", 13 pgs.
"U.S. Appl. No. 11/347,662, Final Office Action dated Oct. 26, 2010", 10 pgs.
"U.S. Appl. No. 11/347,662, Non Final Office Action dated Mar. 9, 2009", 11 pgs.
"U.S. Appl. No. 11/347,662, Non Final Office Action dated May 21, 2010", 19 pgs.
"U.S. Appl. No. 11/347,662, Non Final Office Action dated Oct. 28, 2008", 13 pgs.
"U.S. Appl. No. 11/347,662, Response filed Jan. 16, 2009 to Non Final Office Action dated Oct. 28, 2008", 16 pgs.
"U.S. Appl. No. 11/347,662, Response filed Feb. 12, 2010 to Final Office Action dated Sep. 16, 2009", 21 pgs.
"U.S. Appl. No. 11/347,662, Response filed Jun. 5, 2009 to Non Final Office Action dated Mar. 9, 2009", 13 pgs.
"U.S. Appl. No. 11/347,662, Response filed Aug. 20, 2010 to Non Final Office Action dated May 21, 2010", 13 pgs.
"U.S. Appl. No. 11/386,071, Advisory Action dated Dec. 23, 2010", 3 pgs.
"U.S. Appl. No. 11/386,071, Examiner Interview Summary dated Jan. 31, 2011", 3 pgs.
"U.S. Appl. No. 11/386,071, Examiner Interview Summary dated Jul. 21, 2010", 3 pgs.
"U.S. Appl. No. 11/386,071, Final Office Action dated Oct. 27, 2010", 10 pgs.
"U.S. Appl. No. 11/386,071, Non Final Office Action dated May 12, 2010", 13 pgs.
"U.S. Appl. No. 11/386,071, Notice of Allowance dated Jun. 6, 2011", 6 pgs.
"U.S. Appl. No. 11/386,071, Response filed Jan. 26, 2011 to Advisory Action dated Dec. 23, 2010", 13 pgs.
"U.S. Appl. No. 11/386,071, Response filed Aug. 12, 2010 to Non Final Office Action dated May 12, 2010", 14 pgs.
"U.S. Appl. No. 11/386,071, Response filed Dec. 15, 2010 to Final Office Action dated Oct. 27, 2010", 14 pgs.
"U.S. Appl. No. 11/408,282, Final Office Action dated Dec. 15, 2008", 8 pgs.
"U.S. Appl. No. 11/408,282, Non Final Office Action dated May 23, 2008", 12 pgs.
"U.S. Appl. No. 11/408,282, Response filed Aug. 21, 2008 to Non Final Office Action dated May 23, 2008", 10 pgs.
"U.S. Appl. No. 11/504,882, Examiner Interview Summary dated Sep. 2, 2010", 3 pgs.
"U.S. Appl. No. 11/504,882, Final Office Action dated Dec. 21, 2010", 7 pgs.
"U.S. Appl. No. 11/504,882, Non Final Office Action dated Jun. 19, 2014", 11 pgs.
"U.S. Appl. No. 11/504,882, Non Final Office Action dated Jun. 23, 2010", 8 pgs.
"U.S. Appl. No. 11/504,882, Non Final Office Action dated Nov. 13, 2013", 13 pgs.
"U.S. Appl. No. 11/504,882, Notice of Allowance dated Dec. 1, 2014", 9 pgs.
"U.S. Appl. No. 11/504,882, Response filed Feb. 10, 2014 to Non Final Office Action dated Nov. 13, 2013", 11 pgs.
"U.S. Appl. No. 11/504,882, Response filed Mar. 18, 2011 to Final Office Action dated Dec. 21, 2010", 11 pgs.
"U.S. Appl. No. 11/504,882, Response filed Sep. 17, 2014 to Non Final Office Action dated Jun. 19, 2014", 14 pgs.
"U.S. Appl. No. 11/504,882, Response filed Sep. 23, 2010 to Non Final Office Action dated Jun. 23, 2010", 12 pgs.
"U.S. Appl. No. 11/504,882, Supplemental Notice of Allowability dated Mar. 12, 2015", 5 pgs.
"U.S. Appl. No. 11/541,505, Non Final Office Action dated May 19, 2009", 7 pgs.
"U.S. Appl. No. 11/541,505, Notice of Allowance dated Sep. 18, 2009", 8 pgs.
"U.S. Appl. No. 11/541,505, Response filed Apr. 9, 2009 to Restriction Requirement dated Mar. 9, 2009", 1 pg.
"U.S. Appl. No. 11/541,505, Response filed Jun. 18, 2009 to Non Final Office Action dated May 19, 2009", 5 pgs.
"U.S. Appl. No. 11/541,505, Restriction Requirement dated Mar. 9, 2009", 9 pgs.
"U.S. Appl. No. 11/541,506, Notice of Allowance dated Jun. 1, 2009", 10 pgs.
"U.S. Appl. No. 11/541,506, Notice of Allowance dated Jun. 29, 2009", 8 pgs.
"U.S. Appl. No. 11/541,506, Response filed Apr. 9, 2009 to Restriction Requirement dated Mar. 9, 2009", 1 pg.
"U.S. Appl. No. 11/541,506, Restriction Requirement dated Mar. 9, 2009", 6 pgs.
"U.S. Appl. No. 11/739,768, Examiner Interview Summary dated May 11, 2011", 3 pgs.
"U.S. Appl. No. 11/739,768, Examiner Interview Summary dated Oct. 4, 2011", 3 pgs.
"U.S. Appl. No. 11/739,768, Final Office Action dated Aug. 22, 2011", 14 pgs.
"U.S. Appl. No. 11/739,768, Non Final Office Action dated Mar. 4, 2011", 11 pgs.
"U.S. Appl. No. 11/739,768, Notice of Allowance dated Nov. 15, 2011", 5 pgs.
"U.S. Appl. No. 11/739,768, Response filed Jun. 6, 2011 to Non Final Office Action dated Mar. 4, 2011", 15 pgs.
"U.S. Appl. No. 11/739,768, Response filed Oct. 25, 2011 to Final Office Action dated Aug. 22, 2011", 14 pgs.

(56) References Cited

OTHER PUBLICATIONS

"U.S. Appl. No. 11/740,035, Final Office Action dated Aug. 7, 2008", 9 pgs.
"U.S. Appl. No. 11/740,035, Non Final Office Action dated Jan. 3, 2008", 9 pgs.
"U.S. Appl. No. 11/740,035, Response filed Apr. 3, 2008 to Non Final Office Action dated Jan. 3, 2008", 6 pgs.
"U.S. Appl. No. 11/784,821, Corrected Notice of Allowance dated Dec. 24, 2014", 4 pgs.
"U.S. Appl. No. 11/784,821, Examiner Interview Summary dated Jun. 26, 2014", 3 pgs.
"U.S. Appl. No. 11/784,821, Examiner Interview Summary dated Nov. 17, 2009", 3 pgs.
"U.S. Appl. No. 11/784,821, Final Office Action dated Mar. 10, 2010", 11 pgs.
"U.S. Appl. No. 11/784,821, Non Final Office Action dated Mar. 28, 2014", 14 pgs.
"U.S. Appl. No. 11/784,821, Non Final Office Action dated Sep. 4, 2009", 12 pgs.
"U.S. Appl. No. 11/784,821, Notice of Allowance dated Oct. 21, 2014", 10 pgs.
"U.S. Appl. No. 11/784,821, Response filed Jun. 10, 2010 to Final Office Action dated Mar. 10, 2010", 20 pgs.
"U.S. Appl. No. 11/784,821, Response filed Jun. 15, 2009 to Restriction Requirement dated May 13, 2009", 2 pgs.
"U.S. Appl. No. 11/784,821, Response filed Jun. 26, 2014 to Non Final Office Action dated Mar. 28, 2014", 16 pgs.
"U.S. Appl. No. 11/784,821, Response filed Nov. 23, 2009 to Non Final Office Action dated Sep. 4, 2009", 17 pgs.
"U.S. Appl. No. 11/784,821, Restriction Requirement dated May 13, 2009", 6 pgs.
"U.S. Appl. No. 11/869,440, Examiner Interview Summary dated Mar. 25, 2010", 3 pgs.
"U.S. Appl. No. 11/869,440, Non Final Office Action dated Mar. 1, 2010", 13 pgs.
"U.S. Appl. No. 11/869,440, Notice of Allowance dated Aug. 19, 2010", 10 pgs.
"U.S. Appl. No. 11/869,440, Response filed Jun. 1, 2010 to Non Final Office Action dated Mar. 1, 2010", 14 pgs.
"U.S. Appl. No. 11/935,681, Examiner Interview Summary dated Jul. 19, 2010", 3 pgs.
"U.S. Appl. No. 11/935,681, Non Final Office Action dated May 24, 2010", 12 pgs.
"U.S. Appl. No. 11/935,681, Notice of Allowance dated Nov. 8, 2010", 10 pgs.
"U.S. Appl. No. 11/935,681, Response filed Apr. 19, 2010 to Restriction Requirement dated Mar. 17, 2010", 4 pgs.
"U.S. Appl. No. 11/935,681, Response filed Aug. 24, 2010 to Non Final Office Action dated May 24, 2010", 13 pgs.
"U.S. Appl. No. 11/935,681, Restriction Requirement dated Mar. 17, 2010", 6 pgs.
"U.S. Appl. No. 12/014,340, Examiner Interview Summary dated Jun. 22, 2010", 3 pgs.
"U.S. Appl. No. 12/014,340, Non Final Office Action dated May 25, 2010", 12 pgs.
"U.S. Appl. No. 12/014,340, Notice of Allowance dated Nov. 8, 2010", 9 pgs.
"U.S. Appl. No. 12/014,340, Preliminary Amendment filed May 21, 2010", 11 pgs.
"U.S. Appl. No. 12/014,340, Response filed Apr. 26, 2010 to Restriction Requirement dated Mar. 25, 2010", 2 pgs.
"U.S. Appl. No. 12/014,340, Response filed Aug. 25, 2010 to Non Final Office Action dated May 25, 2010", 16 pgs.
"U.S. Appl. No. 12/014,340, Restriction Requirement dated Mar. 25, 2010", 9 pgs.
"U.S. Appl. No. 12/014,399, Examiner Interview Summary dated Jun. 23, 2010", 3 pgs.
"U.S. Appl. No. 12/014,399, Non Final Office Action dated May 26, 2010", 13 pgs.
"U.S. Appl. No. 12/014,399, Notice of Allowance dated Nov. 12, 2010", 11 pgs.
"U.S. Appl. No. 12/014,399, Preliminary Amendment filed May 25, 2010", 10 pgs.
"U.S. Appl. No. 12/014,399, Response filed May 15, 2010 to Restriction Requirement dated Apr. 6, 2010", 2 pgs.
"U.S. Appl. No. 12/014,399, Response filed Aug. 25, 2010 to Non Final Office Action dated May 26, 2010", 14 pgs.
"U.S. Appl. No. 12/014,399, Restriction Requirement dated Apr. 6, 2010", 9 pgs.
"U.S. Appl. No. 12/029,861, Examiner Interview Summary dated Jan. 27, 2012", 3 pgs.
"U.S. Appl. No. 12/029,861, Final Office Action dated Dec. 8, 2011", 11 pgs.
"U.S. Appl. No. 12/029,861, Non Final Office Action dated Jul. 26, 2011", 11 pgs.
"U.S. Appl. No. 12/029,861, Notice of Allowance dated Apr. 26, 2012", 5 pgs.
"U.S. Appl. No. 12/029,861, Response filed Jan. 26, 2012 to Final Office Action dated Dec. 8, 2011", 15 pgs.
"U.S. Appl. No. 12/029,861, Response filed May 6, 2011 to Restriction Requirement dated Apr. 7, 2011", 10 pgs.
"U.S. Appl. No. 12/029,861, Response filed Jun. 23, 2011 to Restriction Requirement dated May 24, 2011", 1 pgs.
"U.S. Appl. No. 12/029,861, Response filed Oct. 14, 2011 to Non Final Office Action dated Jul. 26, 2011", 11 pgs.
"U.S. Appl. No. 12/029,861, Restriction Requirement dated Apr. 7, 2011", 8 pgs.
"U.S. Appl. No. 12/029,861, Restriction Requirement dated May 24, 2011", 6 pgs.
"U.S. Appl. No. 12/107,437, Examiner Interview Summary dated May 10, 2010", 4 pgs.
"U.S. Appl. No. 12/107,437, Non Final Office Action dated Mar. 17, 2010", 9 pgs.
"U.S. Appl. No. 12/107,437, Preliminary Amendment filed Feb. 23, 2010", 9 pgs.
"U.S. Appl. No. 12/107,437, Response filed Jan. 29, 2010 to Restriction Requirement dated Jan. 13, 2010", 1 pgs.
"U.S. Appl. No. 12/107,437, Restriction Requirement dated Jan. 13, 2010", 7 pgs.
"U.S. Appl. No. 12/196,398, Examiner Interview Summary dated Nov. 8, 2010", 3 pgs.
"U.S. Appl. No. 12/196,398, Notice of Allowance dated Feb. 3, 2011", 12 pgs.
"U.S. Appl. No. 12/196,398, Preliminary Amendment filed Nov. 10, 2008", 3 pgs.
"U.S. Appl. No. 12/196,398, Preliminary Amendment filed Dec. 1, 2010", 12 pgs.
"U.S. Appl. No. 12/196,398, Preliminary Amendment filed Dec. 9, 2008", 46 pgs.
"U.S. Appl. No. 12/196,398, Response filed Oct. 29, 2010 to Restriction Requirement dated Sep. 29, 2010", 2 pgs.
"U.S. Appl. No. 12/196,398, Restriction Requirement dated Sep. 29, 2010", 6 pgs.
"U.S. Appl. No. 12/196,398, Supplemental Notice of Allowability dated Mar. 9, 2011", 4 pgs.
"U.S. Appl. No. 12/196,398, Supplemental Notice of Allowability dated Apr. 15, 2011", 4 pgs.
"U.S. Appl. No. 12/196,405, Examiner Interview Summary dated Jun. 20, 2011", 3 pgs.
"U.S. Appl. No. 12/196,405, Non Final Office Action dated Apr. 11, 2011", 13 pgs.
"U.S. Appl. No. 12/196,405, Notice of Allowance dated Oct. 26, 2011", 11 pgs.
"U.S. Appl. No. 12/196,405, Preliminary Amendment filed Nov. 11, 2008", 3 pgs.
"U.S. Appl. No. 12/196,405, Response filed Mar. 16, 2011 to Restriction Requirement dated Feb. 14, 2011", 1 pgs.
"U.S. Appl. No. 12/196,405, Response filed Jul. 12, 2011 to Non Final Office Action dated Apr. 11, 2011", 19 pgs.
"U.S. Appl. No. 12/196,405, Restriction Requirement dated Feb. 14, 2011", 6 pgs.

(56) References Cited

OTHER PUBLICATIONS

"U.S. Appl. No. 12/196,405, Supplemental Amendment filed Oct. 3, 2011", 12 pgs.
"U.S. Appl. No. 12/196,407, Examiner Interview Summary dated Jul. 14, 2011", 3 pgs.
"U.S. Appl. No. 12/196,407, Non Final Office Action dated May 4, 2011", 11 pgs.
"U.S. Appl. No. 12/196,407, Notice of Allowance dated Oct. 26, 2011", 10 pgs.
"U.S. Appl. No. 12/196,407, Preliminary Amendment filed Nov. 10, 2008", 3 pgs.
"U.S. Appl. No. 12/196,407, Response filed Apr. 20, 2011 to Restriction Requirement dated Mar. 22, 2011", 12 pgs.
"U.S. Appl. No. 12/196,407, Response filed Aug. 2, 2011 to Non Final Office Action dated May 4, 2011", 27 pgs.
"U.S. Appl. No. 12/196,407, Restriction Requirement dated Mar. 22, 2011", 6 pgs.
"U.S. Appl. No. 12/196,407, Supplemental Response to Non Final Office Action filed Oct. 3, 2011", 18 pgs.
"U.S. Appl. No. 12/196,410, Examiner Interview Summary dated Jul. 14, 2011", 3 pgs.
"U.S. Appl. No. 12/196,410, Non Final Office Action dated May 9, 2011", 9 pgs.
"U.S. Appl. No. 12/196,410, Notice of Allowance dated Oct. 13, 2011", 8 pgs.
"U.S. Appl. No. 12/196,410, Response filed Apr. 20, 2011 to Restriction Requirement dated Mar. 22, 2011", 13 pgs.
"U.S. Appl. No. 12/196,410, Response filed Aug. 1, 2011 to Non Final Office Action dated May 9, 2011", 23 pgs.
"U.S. Appl. No. 12/196,410, Restriction Requirement dated Mar. 22, 2011", 6 pgs.
"U.S. Appl. No. 12/196,410, Supplemental Amendment filed Oct. 3, 2011", 15 pgs.
"U.S. Appl. No. 12/398,548, Examiner Interview Summary dated Jul. 12, 2011", 3 pgs.
"U.S. Appl. No. 12/398,548, Non Final Office Action dated Apr. 12, 2011", 7 pgs.
"U.S. Appl. No. 12/398,548, Notice of Allowance dated Oct. 18, 2011", 7 pgs.
"U.S. Appl. No. 12/398,548, Response filed Jul. 12, 2011 to Non Final Office Action dated Apr. 12, 2011", 15 pgs.
"U.S. Appl. No. 12/398,548, Supplemental Preliminary Amendment filed Sep. 7, 2010", 11 pgs.
"U.S. Appl. No. 12/419,491, Examiner Interview Summary dated May 30, 2012", 3 pgs.
"U.S. Appl. No. 12/419,491, Examiner Interview Summary dated Nov. 29, 2011", 3 pgs.
"U.S. Appl. No. 12/419,491, Final Office Action dated Apr. 12, 2012", 12 pgs.
"U.S. Appl. No. 12/419,491, Non Final Office Action dated Sep. 22, 2011", 12 pgs.
"U.S. Appl. No. 12/419,491, Notice of Allowance dated Jul. 13, 2012", 10 pgs.
"U.S. Appl. No. 12/419,491, Response filed May 30, 2012 to Final Office Action dated Apr. 12, 2012", 12 pgs.
"U.S. Appl. No. 12/419,491, Response filed Dec. 9, 2011 to Non Final Office Action dated Sep. 22, 2011", 17 pgs.
"U.S. Appl. No. 12/474,802, Notice of Allowance dated Aug. 31, 2011", 13 pgs.
"U.S. Appl. No. 12/474,802, Notice of Allowance dated Oct. 26, 2011", 4 pgs.
"U.S. Appl. No. 12/474,802, Response filed Mar. 28, 2011 to Restriction Requirement dated Feb. 24, 2011", 12 pgs.
"U.S. Appl. No. 12/474,802, Restriction Requirement dated Feb. 24, 2011", 6 pgs.
"U.S. Appl. No. 12/489,168, Examiner Interview Summary dated Feb. 21, 2012", 3 pgs.
"U.S. Appl. No. 12/489,168, Non Final Office Action dated Dec. 7, 2011", 10 pgs.
"U.S. Appl. No. 12/489,168, Notice of Allowance dated Apr. 26, 2012", 8 pgs.
"U.S. Appl. No. 12/489,168, Notice of Allowance dated Sep. 5, 2012", 8 pgs.
"U.S. Appl. No. 12/489,168, Preliminary Amendment filed Oct. 22, 2009", 3 pgs.
"U.S. Appl. No. 12/489,168, Response filed Feb. 27, 2012 to Non Final Office Action dated Dec. 7, 2011", 15 pgs.
"U.S. Appl. No. 12/489,168, Response filed Nov. 11, 2011 to Restriction Requirement dated Oct. 20, 2011", 1 pg.
"U.S. Appl. No. 12/489,168, Restriction Requirement dated Oct. 20, 2011", 8 pgs.
"U.S. Appl. No. 12/489,181, Examiner Interview Summary dated Feb. 13, 2012", 3 pgs.
"U.S. Appl. No. 12/489,181, Non Final Office Action dated Jan. 3, 2012", 9 pgs.
"U.S. Appl. No. 12/489,181, Notice of Allowance dated May 23, 2012", 9 pgs.
"U.S. Appl. No. 12/489,181, Preliminary Amendment filed Mar. 31, 2011", 10 pgs.
"U.S. Appl. No. 12/489,181, Preliminary Amendment filed Oct. 22, 2009", 3 pgs.
"U.S. Appl. No. 12/489,181, Response filed Mar. 27, 2012 to Non Final Office Action dated Jan. 3, 2012", 12 pgs.
"U.S. Appl. No. 12/489,181, Response filed Dec. 5, 2011 to Restriction Requirement dated Nov. 4, 2011", 1 pg.
"U.S. Appl. No. 12/489,181, Restriction Requirement dated Nov. 4, 2011", 7 pgs.
"U.S. Appl. No. 12/570,854, Examiner Interview Summary dated Apr. 16, 2012", 3 pgs.
"U.S. Appl. No. 12/570,854, Non Final Office Action dated Feb. 10, 2012", 8 pgs.
"U.S. Appl. No. 12/570,854, Notice of Allowance dated Jun. 29, 2012", 10 pgs.
"U.S. Appl. No. 12/570,854, Notice of Allowance dated Sep. 19, 2012", 6 pgs.
"U.S. Appl. No. 12/570,854, Response filed May 10, 2012 to Non Final Office Action dated Feb. 10, 2012", 27 pgs.
"U.S. Appl. No. 12/570,854, Response filed Dec. 20, 2011 to Restriction Requirement dated Dec. 14, 2011", 1 pg.
"U.S. Appl. No. 12/570,854, Restriction Requirement dated Dec. 14, 2011", 6 pgs.
"U.S. Appl. No. 12/702,067, Non Final Office Action dated Mar. 5, 2013", 8 pgs.
"U.S. Appl. No. 12/702,067, Notice of Allowance dated Oct. 7, 2013", 11 pgs.
"U.S. Appl. No. 12/702,067, Preliminary Amendment filed Jan. 11, 2011", 13 pgs.
"U.S. Appl. No. 12/702,067, Response filed Jun. 5, 2013 to Non Final Office Action dated Mar. 5, 2013", 17 pgs.
"U.S. Appl. No. 12/702,067, Response filed Oct. 2, 2012 to Restriction Requirement dated Sep. 4, 2012", 1 pg.
"U.S. Appl. No. 12/702,067, Restriction Requirement dated Sep. 4, 2012", 9 pgs.
"U.S. Appl. No. 12/719,337, Advisory Action dated Sep. 30, 2014", 4 pgs.
"U.S. Appl. No. 12/719,337, Examiner Interview Summary dated Apr. 4, 2014", 4 pgs.
"U.S. Appl. No. 12/719,337, Examiner Interview Summary dated May 14, 2013", 3 pgs.
"U.S. Appl. No. 12/719,337, Examiner Interview Summary dated Sep. 18, 2014", 3 pgs.
"U.S. Appl. No. 12/719,337, Final Office Action dated Mar. 12, 2013", 8 pgs.
"U.S. Appl. No. 12/719,337, Final Office Action dated Jul. 18, 2014", 15 pgs.
"U.S. Appl. No. 12/719,337, Non Final Office Action dated Jan. 10, 2014", 14 pgs.
"U.S. Appl. No. 12/719,337, Non Final Office Action dated Sep. 5, 2012", 7 pgs.
"U.S. Appl. No. 12/719,337, Notice of Allowance dated Mar. 11, 2015", 10 pgs.

(56) References Cited

OTHER PUBLICATIONS

"U.S. Appl. No. 12/719,337, Notice of Non-Compliant Amendment dated May 2, 2014", 3 pgs.
"U.S. Appl. No. 12/719,337, Response filed Apr. 10, 2014 to Non Final Office Action dated Jan. 10, 2014", 16 pgs.
"U.S. Appl. No. 12/719,337, Response filed May 25, 2012 to Restriction Requirement dated Apr. 26, 2012", 9 pgs.
"U.S. Appl. No. 12/719,337, Response filed Jun. 5, 2013 to Final Office Action dated Mar. 12, 2013", 16 pgs.
"U.S. Appl. No. 12/719,337, Response filed Jun. 25, 2014 to Notice of Non-Compliant Amendment dated May 2, 2014", 10 pgs.
"U.S. Appl. No. 12/719,337, Response filed Sep. 18, 2014 to Final Office Action dated Jul. 18, 2014", 13 pgs.
"U.S. Appl. No. 12/719,337, Response filed Nov. 28, 2012 to Non Final Office Action dated Sep. 5, 2012", 14 pgs.
"U.S. Appl. No. 12/719,337, Restriction Requirement dated Apr. 26, 2012", 8 pgs.
"U.S. Appl. No. 12/788,966, Examiner Interview Summary dated Jun. 1, 2012", 3 pgs.
"U.S. Appl. No. 12/788,966, Final Office Action dated May 4, 2012", 16 pgs.
"U.S. Appl. No. 12/788,966, Non Final Office Action dated Jan. 4, 2012", 12 pgs.
"U.S. Appl. No. 12/788,966, Notice of Allowance dated Aug. 16, 2012", 10 pgs.
"U.S. Appl. No. 12/788,966, Notice of Allowance dated Nov. 23, 2012", 2 pgs.
"U.S. Appl. No. 12/788,966, Response filed Apr. 4, 2012 to Non Final Office Action dated Jan. 4, 2012", 15 pgs.
"U.S. Appl. No. 12/788,966, Response filed Aug. 6, 2012 to Final Office Action dated May 4, 2012", 12 pgs.
"U.S. Appl. No. 12/788,966, Response filed Dec. 16, 2011 to Restriction Requirement dated Dec. 7, 2011", 11 pgs.
"U.S. Appl. No. 12/788,966, Restriction Requirement dated Dec. 7, 2011", 9 pgs.
"U.S. Appl. No. 12/788,973, Advisory Action dated Jan. 23, 2013", 3 pgs.
"U.S. Appl. No. 12/788,973, Advisory Action dated Dec. 27, 2012", 8 pgs.
"U.S. Appl. No. 12/788,973, Final Office Action dated Sep. 18, 2012", 16 pgs.
"U.S. Appl. No. 12/788,973, Non Final Office Action dated May 8, 2012", 12 pgs.
"U.S. Appl. No. 12/788,973, Notice of Allowance dated Mar. 21, 2013", 6 pgs.
"U.S. Appl. No. 12/788,973, Response filed Jan. 16, 2013 to Advisory Action dated Dec. 27, 2012", 9 pgs.
"U.S. Appl. No. 12/788,973, Response filed Jul. 19, 2012 to Non Final Office Action dated May 8, 2012", 21 pgs.
"U.S. Appl. No. 12/788,973, Response filed Dec. 16, 2011 to Restriction Requirement dated Dec. 6, 2011", 11 pgs.
"U.S. Appl. No. 12/788,973, Response filed Dec. 17, 2012 to Final Office Action dated Sep. 18, 2012", 15 pgs.
"U.S. Appl. No. 12/788,973, Restriction Requirement dated Dec. 6, 2011", 9 pgs.
"U.S. Appl. No. 12/788,973, Supplemental Notice of Allowance dated May 24, 2013", 2 pgs.
"U.S. Appl. No. 12/788,978, Advisory Action dated Dec. 24, 2013", 4 pgs.
"U.S. Appl. No. 12/788,978, Applicant's Summary of Examiner Interview filed Dec. 12, 2013", 2 pgs.
"U.S. Appl. No. 12/788,978, Corrected Notice of Allowance dated Apr. 30, 2014", 2 pgs.
"U.S. Appl. No. 12/788,978, Examiner Interview Summary dated Jan. 28, 2014", 3 pgs.
"U.S. Appl. No. 12/788,978, Examiner Interview Summary dated Mar. 22, 2013", 3 pgs.
"U.S. Appl. No. 12/788,978, Examiner Interview Summary dated Sep. 11, 2012", 3 pgs.
"U.S. Appl. No. 12/788,978, Examiner Interview Summary dated Oct. 29, 2013", 4 pgs.
"U.S. Appl. No. 12/788,978, Examiner Interview Summary dated Dec. 16, 2013", 3 pgs.
"U.S. Appl. No. 12/788,978, Examiner Interview Summary dated Dec. 27, 2012", 3 pgs.
"U.S. Appl. No. 12/788,978, Final Office Action dated Aug. 20, 2013", 17 pgs.
"U.S. Appl. No. 12/788,978, Final Office Action dated Nov. 2, 2012", 14 pgs.
"U.S. Appl. No. 12/788,978, Non Final Office Action dated Jan. 11, 2013", 16 pgs.
"U.S. Appl. No. 12/788,978, Non Final Office Action dated Jul. 13, 2012", 17 pgs.
"U.S. Appl. No. 12/788,978, Notice of Allowance dated Jan. 24, 2014", 9 pgs.
"U.S. Appl. No. 12/788,978, Notice of Non-Compliant Amendment dated Jun. 6, 2013", 3 pgs.
"U.S. Appl. No. 12/788,978, Response filed Jan. 2, 2013 to Final Office Action dated Nov. 2, 2012", 13 pgs.
"U.S. Appl. No. 12/788,978, Response filed Jan. 20, 2014 to Advisory Action dated Dec. 24, 2013", 4 pgs.
"U.S. Appl. No. 12/788,978, Response filed Apr. 8, 2013 to Non Final Office Action dated Jan. 11, 2013", 16 pgs.
"U.S. Appl. No. 12/788,978, Response filed May 21, 2012 to Restriction Requirement dated Apr. 20, 2012", 12 pgs.
"U.S. Appl. No. 12/788,978, Response filed Jul. 3, 2013 to Notice of Non-Compliant Amendment dated Jun. 6, 2013", 17 pgs.
"U.S. Appl. No. 12/788,978, Response filed Oct. 5, 2012 to Non Final Office Action dated Jul. 13, 2012", 20 pgs.
"U.S. Appl. No. 12/788,978, Response filed Nov. 20, 2013 to Final Office Action dated Aug. 20, 2013", 15 pgs.
"U.S. Appl. No. 12/788,978, Restriction Requirement dated Apr. 20, 2012", 8 pgs.
"U.S. Appl. No. 12/828,977, Examiner Interview Summary dated Jul. 9, 2012", 3 pgs.
"U.S. Appl. No. 12/828,977, Non Final Office Action dated May 3, 2012", 9 pgs.
"U.S. Appl. No. 12/828,977, Notice of Allowance dated Sep. 5, 2012", 9 pgs.
"U.S. Appl. No. 12/828,977, Preliminary Amendment filed Jul. 19, 2011", 10 pgs.
"U.S. Appl. No. 12/828,977, Response filed Mar. 14, 2012 to Restriction Requirement dated Feb. 13, 2012", 9 pgs.
"U.S. Appl. No. 12/828,977, Response filed Jul. 25, 2012 to Non Final Office Action dated May 3, 2012", 11 pgs.
"U.S. Appl. No. 12/828,977, Restriction Requirement dated Feb. 13, 2012", 7 pgs.
"U.S. Appl. No. 12/915,962, Examiner Interview Summary dated Jul. 25, 2012", 3 pgs.
"U.S. Appl. No. 12/915,962, Non Final Office Action dated May 7, 2012", 11 pgs.
"U.S. Appl. No. 12/915,962, Non Final Office Action dated Oct. 15, 2012", 9 pgs.
"U.S. Appl. No. 12/915,962, Notice of Allowance dated Jun. 10, 2013", 12 pgs.
"U.S. Appl. No. 12/915,962, Response filed Jan. 10, 2013 to Non Final Office Action dated Oct. 15, 2012", 21 pgs.
"U.S. Appl. No. 12/915,962, Response filed Mar. 16, 2012 to Restriction Requirement dated Feb. 15, 2012", 15 pgs.
"U.S. Appl. No. 12/915,962, Response filed Aug. 7, 2012 to Non Final Office Action dated May 7, 2012", 26 pgs.
"U.S. Appl. No. 12/915,962, Restriction Requirement dated Feb. 15, 2012", 8 pgs.
"U.S. Appl. No. 12/938,902, Examiner Interview Summary dated Dec. 3, 2012", 3 pgs.
"U.S. Appl. No. 12/938,902, Non Final Office Action dated Sep. 17, 2012", 11 pgs.
"U.S. Appl. No. 12/938,902, Notice of Allowance dated Jun. 21, 2013", 13 pgs.
"U.S. Appl. No. 12/938,902, Notice of Allowance dated Oct. 1, 2013", 9 pgs.

(56) References Cited

OTHER PUBLICATIONS

"U.S. Appl. No. 12/938,902, Response filed Aug. 6, 2012 to Restriction Requirement dated Jul. 6, 2012", 14 pgs.
"U.S. Appl. No. 12/938,902, Response filed Dec. 10, 2012 to Non Final Office Action dated Sep. 17, 2012", 20 pgs.
"U.S. Appl. No. 12/938,902, Restriction Requirement dated Jul. 6, 2012", 8 pgs.
"U.S. Appl. No. 12/976,328, Examiner Interview Summary dated Feb. 13, 2012", 3 pgs.
"U.S. Appl. No. 12/976,328, Non Final Office Action dated Dec. 15, 2011", 13 pgs.
"U.S. Appl. No. 12/976,328, Notice of Allowance dated Apr. 30, 2012", 9 pgs.
"U.S. Appl. No. 12/976,328, Response filed Mar. 2, 2012 to Non Final Office Action dated Dec. 15, 2011", 15 pgs.
"U.S. Appl. No. 13/045,689, Examiner Interview Summary dated May 14, 2012", 3 pgs.
"U.S. Appl. No. 13/045,689, Non Final Office Action dated Mar. 20, 2012", 11 pgs.
"U.S. Appl. No. 13/045,689, Notice of Allowance dated Aug. 10, 2012", 10 pgs.
"U.S. Appl. No. 13/045,689, Notice of Allowance dated Sep. 24, 2012", 7 pgs.
"U.S. Appl. No. 13/045,689, Response filed Jan. 30, 2012 to Restriction Requirement dated Dec. 29, 2011", 13 pgs.
"U.S. Appl. No. 13/045,689, Response filed Jun. 8, 2012 to Non Final Office Action dated Mar. 20, 2012", 15 pgs.
"U.S. Appl. No. 13/045,689, Restriction Requirement dated Dec. 29, 2011", 6 pgs.
"U.S. Appl. No. 13/045,691, Examiner Interview Summary dated May 14, 2012", 3 pgs.
"U.S. Appl. No. 13/045,691, Non Final Office Action dated Mar. 20, 2012", 12 pgs.
"U.S. Appl. No. 13/045,691, Notice of Allowance dated Jun. 19, 2012", 10 pgs.
"U.S. Appl. No. 13/045,691, Response filed Feb. 9, 2012 to Restriction Requirement dated Jan. 9, 2012", 1 pg.
"U.S. Appl. No. 13/045,691, Response filed Jun. 8, 2012 to Non Final Office Action dated Mar. 20, 2012", 17 pgs.
"U.S. Appl. No. 13/045,691, Restriction Requirement dated Jan. 9, 2012", 6 pgs.
"U.S. Appl. No. 13/071,563, Final Office Action dated May 23, 2014", 13 pgs.
"U.S. Appl. No. 13/071,563, Non Final Office Action dated Oct. 23, 2013", 18 pgs.
"U.S. Appl. No. 13/071,563, Notice of Allowance dated Aug. 15, 2014", 7 pgs.
"U.S. Appl. No. 13/071,563, Preliminary Amendment filed May 1, 2012", 8 pgs.
"U.S. Appl. No. 13/071,563, Preliminary Amendment filed Dec. 6, 2011", 7 pgs.
"U.S. Appl. No. 13/071,563, Response filed Jan. 21, 2014 to Non Final Office Action dated Oct. 23, 2013", 13 pgs.
"U.S. Appl. No. 13/071,563, Response filed Jul. 23, 14 to Final Office Action mailed May 23, 2014", 14 pgs.
"U.S. Appl. No. 13/071,563, Response filed Sep. 19, 2013 to Restriction Requirement dated Aug. 19, 2013", 11 pgs.
"U.S. Appl. No. 13/071,563, Restriction Requirement dated Aug. 19, 2013", 7 pgs.
"U.S. Appl. No. 13/098,897, Examiner Interview Summary dated Nov. 27, 2012", 3 pgs.
"U.S. Appl. No. 13/098,897, Non Final Office Action dated Sep. 21, 2012", 9 pgs.
"U.S. Appl. No. 13/098,897, Notice of Allowance dated Jun. 11, 2013", 13 pgs.
"U.S. Appl. No. 13/098,897, Response filed Aug. 30, 2012 to Restriction Requirement dated Jul. 30, 2012", 16 pgs.
"U.S. Appl. No. 13/098,897, Response filed Dec. 18, 2012 to Non Final Office Action dated Sep. 21, 2012", 21 pgs.
"U.S. Appl. No. 13/098,897, Restriction Requirement dated Jul. 30, 2012", 8 pgs.
"U.S. Appl. No. 13/098,927, Advisory Action dated Aug. 8, 2013", 3 pgs.
"U.S. Appl. No. 13/098,927, Applicant's Summary of Examiner Interview filed Sep. 23, 2013", 12 pgs.
"U.S. Appl. No. 13/098,927, Examiner Interview Summary dated Jun. 28, 2013", 3 pgs.
"U.S. Appl. No. 13/098,927, Examiner Interview Summary dated Sep. 20, 2013", 3 pgs.
"U.S. Appl. No. 13/098,927, Final Office Action dated May 22, 2013", 10 pgs.
"U.S. Appl. No. 13/098,927, Non Final Office Action dated Sep. 24, 2012", 12 pgs.
"U.S. Appl. No. 13/098,927, Notice of Allowance dated Jan. 8, 2014", 5 pgs.
"U.S. Appl. No. 13/098,927, Notice of Allowance dated Sep. 26, 2013", 14 pgs.
"U.S. Appl. No. 13/098,927, Response filed Jul. 22, 2015 to Final Office Action dated May 22, 2013", 17 pgs.
"U.S. Appl. No. 13/098,927, Response filed Aug. 27, 2012 to Restriction Requirement dated Jul. 25, 2012", 14 pgs.
"U.S. Appl. No. 13/098,927, Response filed Dec. 21, 2012 to Non Final Office Action dated Sep. 24, 2012", 21 pgs.
"U.S. Appl. No. 13/098,927, Restriction Requirement dated Jul. 25, 2012", 8 pgs.
"U.S. Appl. No. 13/102,182, Notice of Allowance dated Mar. 22, 2012", 10 pgs.
"U.S. Appl. No. 13/109,667, Advisory Action dated Feb. 4, 2014", 4 pgs.
"U.S. Appl. No. 13/109,667, Examiner Interview Summary dated Dec. 20, 2013", 3 pgs.
"U.S. Appl. No. 13/109,667, Final Office Action dated Oct. 11, 2013", 19 pgs.
"U.S. Appl. No. 13/109,667, Non Final Office Action dated May 21, 2013", 21 pgs.
"U.S. Appl. No. 13/109,667, Notice of Allowance dated Feb. 18, 2014", 10 pgs.
"U.S. Appl. No. 13/109,667, Response filed Jan. 13, 2014 to Final Office Action dated Oct. 11, 2013", 20 pgs.
"U.S. Appl. No. 13/109,667, Response filed May 2, 2013 to Restriction Requirement dated Apr. 2, 2013", 1 pg.
"U.S. Appl. No. 13/109,667, Response filed Aug. 21, 2013 to Non Final Office Action dated May 21, 2013", 27 pgs.
"U.S. Appl. No. 13/109,667, Restriction Requirement dated Apr. 2, 2013", 8 pgs.
"U.S. Appl. No. 13/109,667, Supplemental Notice of Allowability dated Jun. 12, 2014", 3 pgs.
"U.S. Appl. No. 13/109,667, Supplemental Notice of Allowance dated May 28, 2014", 2 pgs.
"U.S. Appl. No. 13/109,667, Supplemental Preliminary Amendment filed Feb. 4, 2014", 16 pgs.
"U.S. Appl. No. 13/109,672, 312 Amendment filed Jan. 15, 2015", 3 pgs.
"U.S. Appl. No. 13/109,672, Non Final Office Action dated May 15, 2014", 10 pgs.
"U.S. Appl. No. 13/109,672, Notice of Allowance dated Feb. 3, 2015", 2 pgs.
"U.S. Appl. No. 13/109,672, Notice of Allowance dated Sep. 29, 2014", 9 pgs.
"U.S. Appl. No. 13/109,672, PTO Response to Rule 312 Communication dated Jan. 27, 2015", 2 pgs.
"U.S. Appl. No. 13/109,672, Response filed Apr. 14, 2014 to Restriction Requirement dated Feb. 14, 2014", 15 pgs.
"U.S. Appl. No. 13/109,672, Response filed Aug. 15, 2014 to Non Final Office Action dated May 15, 2014", 20 pgs.
"U.S. Appl. No. 13/109,672, Response filed Nov. 4, 2013 to Restriction Requirement dated Oct. 2, 2013", 10 pgs.
"U.S. Appl. No. 13/109,672, Restriction Requirement dated Feb. 14, 2014", 7 pgs.
"U.S. Appl. No. 13/109,672, Restriction Requirement dated Oct. 2, 2013", 7 pgs.

(56) References Cited

OTHER PUBLICATIONS

"U.S. Appl. No. 13/111,564, Corrected Notice of Allowance dated Oct. 9, 2013", 2 pgs.
"U.S. Appl. No. 13/111,564, Examiner Interview Summary dated Jun. 18, 2013", 3 pgs.
"U.S. Appl. No. 13/111,564, Non Final Office Action dated Mar. 18, 2013", 8 pgs.
"U.S. Appl. No. 13/111,564, Notice of Allowance dated Jun. 28, 2013", 12 pgs.
"U.S. Appl. No. 13/111,564, Response filed Feb. 4, 2013 to Restriction Requirement dated Jan. 3, 2013", 20 pgs.
"U.S. Appl. No. 13/111,564, Response filed Jun. 18, 2013 to Non Final Office Action dated Mar. 18, 2013", 25 pgs.
"U.S. Appl. No. 13/111,564, Restriction Requirement dated Jan. 3, 2013", 5 pgs.
"U.S. Appl. No. 13/177,153, Final Office Action dated May 28, 2013", 11 pgs.
"U.S. Appl. No. 13/177,153, Non Final Office Action dated Oct. 2, 2012", 11 pgs.
"U.S. Appl. No. 13/177,153, Notice of Allowance dated Jan. 7, 2014", 4 pgs.
"U.S. Appl. No. 13/177,153, Notice of Allowance dated Sep. 17, 2013", 13 pgs.
"U.S. Appl. No. 13/177,153, Response filed Aug. 28, 2013 to Final Office Action dated May 28, 2013", 19 pgs.
"U.S. Appl. No. 13/177,153, Response filed Sep. 4, 2012 to Restriction Requirement dated Aug. 2, 2012", 15 pgs.
"U.S. Appl. No. 13/177,153, Response filed Dec. 20, 2012 to Non Final Office Action dated Oct. 2, 2012", 16 pgs.
"U.S. Appl. No. 13/177,153, Restriction Requirement dated Aug. 2, 2012", 9 pgs.
"U.S. Appl. No. 13/181,729, Examiner Interview Summary dated May 9, 2013", 3 pgs.
"U.S. Appl. No. 13/181,729, Final Office Action dated Mar. 13, 2013", 14 pgs.
"U.S. Appl. No. 13/181,729, Non Final Office Action dated Oct. 2, 2012", 7 pgs.
"U.S. Appl. No. 13/181,729, Notice of Allowance dated May 23, 2013", 9 pgs.
"U.S. Appl. No. 13/181,729, Response filed May 13, 2013 to Final Office Action dated Mar. 13, 2013", 13 pgs.
"U.S. Appl. No. 13/181,729, Response filed Dec. 20, 2012 to Non Final Office Action dated Oct. 2, 2012", 15 pgs.
"U.S. Appl. No. 13/269,097, Final Office Action dated Aug. 8, 2013", 7 pgs.
"U.S. Appl. No. 13/269,097, Non Final Office Action dated Feb. 12, 2013", 10 pgs.
"U.S. Appl. No. 13/269,097, Notice of Allowance dated Feb. 3, 2014", 5 pgs.
"U.S. Appl. No. 13/269,097, Notice of Allowance dated Oct. 21, 2013", 9 pgs.
"U.S. Appl. No. 13/269,097, Response filed May 13, 2013 to Non Final Office Action dated Feb. 12, 2013", 17 pgs.
"U.S. Appl. No. 13/269,097, Response filed Oct. 8, 2013 to Final Office Action dated Aug. 8, 2013", 12 pgs.
"U.S. Appl. No. 13/269,097, Response filed Nov. 13, 2012 to Restriction Requirement dated Oct. 17, 2012", 1 pg.
"U.S. Appl. No. 13/269,097, Restriction Requirement dated Oct. 17, 2012", 8 pgs.
"U.S. Appl. No. 13/278,341, Notice of Allowance dated Jun. 18, 2013", 10 pgs.
"U.S. Appl. No. 13/278,341, Response filed Mar. 8, 2013 to Restriction Requirement dated Feb. 11, 2013", 1 pg.
"U.S. Appl. No. 13/278,341, Restriction Requirement dated Feb. 11, 2013", 6 pgs.
"U.S. Appl. No. 13/281,009, Corrected Notice of Allowance dated Nov. 18, 2016", 4 pgs.
"U.S. Appl. No. 13/281,009, Corrected Notice of Allowance dated Dec. 12, 2016", 2 pgs.
"U.S. Appl. No. 13/281,009, Examiner Interview Summary dated Nov. 18, 2016", 2 pgs.
"U.S. Appl. No. 13/281,009, Non Final Office Action dated Jun. 2, 2015", 9 pgs.
"U.S. Appl. No. 13/281,009, Notice of Allowance dated Feb. 24, 2016", 9 pgs.
"U.S. Appl. No. 13/281,009, Notice of Allowance dated Jun. 23, 2016", 9 pgs.
"U.S. Appl. No. 13/281,009, Notice of Allowance dated Oct. 29, 2015", 8 pgs.
"U.S. Appl. No. 13/281,009, Response filed Sep. 2, 2015 to Non Final Office Action dated Jun. 2, 2015", 13 pgs.
"U.S. Appl. No. 13/281,009, Restriction Requirement dated Feb. 11, 2015", 6 pgs.
"U.S. Appl. No. 13/288,459, Corrected Notice of Allowance dated Aug. 3, 2016", 4 pgs.
"U.S. Appl. No. 13/288,459, Corrected Notice of Allowance dated Sep. 9, 2016", 4 pgs.
"U.S. Appl. No. 13/288,459, Corrected Notice of Allowance dated Sep. 23, 2016", 4 pgs.
"U.S. Appl. No. 13/288,459, Examiner Interview Summary dated Feb. 6, 2015", 3 pgs.
"U.S. Appl. No. 13/288,459, Non Final Office Action dated Jun. 24, 2015", 10 pgs.
"U.S. Appl. No. 13/288,459, Non Final Office Action dated Nov. 4, 2014", 15 pgs.
"U.S. Appl. No. 13/288,459, Notice of Allowance dated Jan. 11, 2016", 13 pgs.
"U.S. Appl. No. 13/288,459, Notice of Allowance dated May 10, 2016", 7 pgs.
"U.S. Appl. No. 13/288,459, Response filed Mar. 3, 2015 to Non Final Office Action dated Nov. 4, 2014", 16 pgs.
"U.S. Appl. No. 13/288,459, Response filed Oct. 13, 2014 to Restriction Requirement dated Aug. 11, 2014", 15 pgs.
"U.S. Appl. No. 13/288,459, Response filed Oct. 23, 2015 to Non Final Office Action dated Jun. 24, 2015", 14 pgs.
"U.S. Appl. No. 13/288,459, Restriction Requirement dated Aug. 11, 2014", 9 pgs.
"U.S. Appl. No. 13/288,463, Examiner Interview Summary dated Jun. 3, 2014", 3 pgs.
"U.S. Appl. No. 13/288,463, Non Final Office Action dated Feb. 24, 2014", 13 pgs.
"U.S. Appl. No. 13/288,463, Notice of Allowance dated Aug. 27, 2014", 9 pgs.
"U.S. Appl. No. 13/288,463, Response filed May 27, 2014 to Non Final Office Action dated Feb. 24, 2014", 15 pgs.
"U.S. Appl. No. 13/288,463, Supplemental Notice of Allowability dated Dec. 8, 2014", 5 pgs.
"U.S. Appl. No. 13/288,463, Supplemental Notice of Allowability dated Dec. 19, 2014", 5 pgs.
"U.S. Appl. No. 13/293,825, Notice of Allowability dated Jun. 22, 2015", 7 pgs.
"U.S. Appl. No. 13/293,825, Notice of Allowance dated May 19, 2015", 9 pgs.
"U.S. Appl. No. 13/293,825, Response filed Apr. 15, 2015 to Restriction Requirement dated Feb. 12, 2015", 17 pgs.
"U.S. Appl. No. 13/293,825, Restriction Requirement dated Feb. 12, 2015", 9 pgs.
"U.S. Appl. No. 13/295,126, Non Final Office Action dated May 19, 2015", 9 pgs.
"U.S. Appl. No. 13/295,126, Notice of Allowance dated Oct. 22, 2015", 9 pgs.
"U.S. Appl. No. 13/295,126, Response filed Apr. 13, 2015 to Restriction Requirement dated Feb. 12, 2015", 1 pgs.
"U.S. Appl. No. 13/295,126, Response filed Aug. 17, 2015 to Non Final Office Action dated May 19, 2015", 21 pgs.
"U.S. Appl. No. 13/295,126, Restriction Requirement dated Feb. 12, 2015", 9 pgs.
"U.S. Appl. No. 13/311,936, Examiner Interview Summary dated Feb. 12, 2015", 2 pgs.
"U.S. Appl. No. 13/311,936, Non Final Office Action dated Feb. 9, 2015", 13 pgs.

(56) References Cited

OTHER PUBLICATIONS

"U.S. Appl. No. 13/311,936, Non Final Office Action dated Oct. 19, 2015", 8 pgs.
"U.S. Appl. No. 13/311,936, Notice of Allowance dated Mar. 29, 2016", 8 pgs.
"U.S. Appl. No. 13/311,936, Response filed Jan. 18, 2016 to Non Final Office Action dated Oct. 19, 2015", 8 pgs.
"U.S. Appl. No. 13/311,936, Response filed Jun. 9, 2015 to Non Final Office Action dated Feb. 9, 2015", 12 pgs.
"U.S. Appl. No. 13/311,936, Response filed Oct. 3, 2014 to Restriction Requirement dated Aug. 5, 2014", 10 pgs.
"U.S. Appl. No. 13/311,936, Restriction Requirement dated Aug. 5, 2014", 7 pgs.
"U.S. Appl. No. 13/350,985, Final Office Action dated Apr. 16, 2015", 8 pgs.
"U.S. Appl. No. 13/350,985, Non Final Office Action dated Dec. 15, 2014", 8 pgs.
"U.S. Appl. No. 13/350,985, Notice of Allowance dated Jul. 27, 2015", 5 pgs.
"U.S. Appl. No. 13/350,985, Response filed Mar. 13, 2015 to Non Final Office Action dated Dec. 15, 2014", 10 pgs.
"U.S. Appl. No. 13/350,985, Response filed Jul. 9, 2015 to Final Office Action dated Apr. 16, 2015", 8 pgs.
"U.S. Appl. No. 13/350,985, Response filed Dec. 2, 2014 to Restriction Requirement dated Oct. 2, 2014", 9 pgs.
"U.S. Appl. No. 13/350,985, Restriction Requirement dated Oct. 2, 2014", 6 pgs.
"U.S. Appl. No. 13/399,125, Corrected Notice of Allowance dated Aug. 28, 2014", 2 pgs.
"U.S. Appl. No. 13/399,125, Examiner Interview Summary dated May 17, 2013", 3 pgs.
"U.S. Appl. No. 13/399,125, Final Office Action dated Mar. 20, 2013", 12 pgs.
"U.S. Appl. No. 13/399,125, Non Final Office Action dated Oct. 24, 2012", 12 pgs.
"U.S. Appl. No. 13/399,125, Notice of Allowance dated May 16, 2014", 8 pgs.
"U.S. Appl. No. 13/399,125, Response filed Jan. 10, 2013 to Non Final Office Action dated Oct. 24, 2012", 15 pgs.
"U.S. Appl. No. 13/399,125, Response filed May 20, 2013 to Final Office Action dated Mar. 20, 2013", 14 pgs.
"U.S. Appl. No. 13/412,105, Advisory Action dated Feb. 24, 2014", 3 pgs.
"U.S. Appl. No. 13/412,105, Examiner Interview Summary dated Feb. 6, 2014", 3 pgs.
"U.S. Appl. No. 13/412,105, Examiner Interview Summary dated Oct. 11, 2013", 3 pgs.
"U.S. Appl. No. 13/412,105, Final Office Action dated Dec. 13, 2013", 9 pgs.
"U.S. Appl. No. 13/412,105, Non Final Office Action dated Jul. 15, 2013", 10 pgs.
"U.S. Appl. No. 13/412,105, Notice of Allowance dated Aug. 18, 2014", 9 pgs.
"U.S. Appl. No. 13/412,105, Response filed Feb. 10, 2014 to Final Office Action dated Dec. 13, 2013", 14 pgs.
"U.S. Appl. No. 13/412,105, Response filed Mar. 13, 2014 to Advisory Action dated Feb. 24, 2014", 19 pgs.
"U.S. Appl. No. 13/412,105, Response filed May 6, 2013 to Restriction Requirement dated Apr. 5, 2013", 9 pgs.
"U.S. Appl. No. 13/412,105, Response filed Oct. 14, 2013 to Non Final Office Action dated Jul. 15, 2013", 13 pgs.
"U.S. Appl. No. 13/412,105, Restriction Requirement dated Apr. 5, 2013", 9 pgs.
"U.S. Appl. No. 13/412,116, Corrected Notice of Allowance dated Jun. 2, 2014", 2 pgs.
"U.S. Appl. No. 13/412,116, Examiner Interview Summary dated Dec. 13, 2013", 3 pgs.
"U.S. Appl. No. 13/412,116, Non Final Office Action dated Sep. 11, 2013", 9 pgs.
"U.S. Appl. No. 13/412,116, Notice of Allowance dated Feb. 19, 2014", 9 pgs.
"U.S. Appl. No. 13/412,116, Response filed Jul. 3, 2013 to Restriction Requirement dated Jun. 19, 2013", 1 pg.
"U.S. Appl. No. 13/412,116, Response filed Dec. 11, 2013 to Non Final Office Action dated Sep. 11, 2013", 11 pgs.
"U.S. Appl. No. 13/412,116, Restriction Requirement dated Jun. 19, 2013", 9 pgs.
"U.S. Appl. No. 13/412,127, Examiner Interview Summary dated Nov. 5, 2013", 3 pgs.
"U.S. Appl. No. 13/412,127, Non Final Office Action dated Aug. 7, 2013", 15 pgs.
"U.S. Appl. No. 13/412,127, Notice of Allowance dated Dec. 24, 2013", 10 pgs.
"U.S. Appl. No. 13/412,127, Response filed May 23, 2013 to Restriction Requirement dated Apr. 24, 2013", 2 pgs.
"U.S. Appl. No. 13/412,127, Response filed Nov. 5, 2013 to Non Final Office Action dated Aug. 7, 2013", 16 pgs.
"U.S. Appl. No. 13/412,127, Restriction Requirement dated Apr. 24, 2013", 10 pgs.
"U.S. Appl. No. 13/587,374, Final Office Action dated Nov. 6, 2013", 9 pgs.
"U.S. Appl. No. 13/587,374, Non Final Office Action dated Jul. 17, 2013", 8 pgs.
"U.S. Appl. No. 13/587,374, Notice of Allowance dated Feb. 28, 2014", 5 pgs.
"U.S. Appl. No. 13/587,374, Preliminary Amendment filed Jun. 21, 2013", 9 pgs.
"U.S. Appl. No. 13/587,374, Response filed Jan. 24, 2014 to Final Office Action dated Nov. 6, 2013", 15 pgs.
"U.S. Appl. No. 13/587,374, Response filed Oct. 14, 2013 to Non Final Office Action dated Jul. 17, 2013", 14 pgs.
"U.S. Appl. No. 13/625,413, Final Office Action dated Oct. 30, 2015", 8 pgs.
"U.S. Appl. No. 13/625,413, Non Final Office Action dated Jun. 8, 2015", 11 pgs.
"U.S. Appl. No. 13/625,413, Notice of Allowance dated Apr. 1, 2016", 8 pgs.
"U.S. Appl. No. 13/625,413, Notice of Allowance dated Dec. 11, 2015", 9 pgs.
"U.S. Appl. No. 13/625,413, Response filed May 11, 2015 to Restriction Requirement dated Mar. 10, 2015", 1 pg.
"U.S. Appl. No. 13/625,413, Response filed Sep. 8, 2015 to Non Final Office Action dated Jun. 8, 2015", 16 pgs.
"U.S. Appl. No. 13/625,413, Response filed Dec. 1, 2015 to Final Office Action dated Oct. 30, 2015", 9 pgs.
"U.S. Appl. No. 13/625,413, Restriction Requirement dated Mar. 10, 2015", 7 pgs.
"U.S. Appl. No. 13/645,964, Advisory Action dated Feb. 4, 2016", 2 pgs.
"U.S. Appl. No. 13/645,964, Final Office Action dated Oct. 6, 2015", 17 pgs.
"U.S. Appl. No. 13/645,964, Non Final Office Action dated Mar. 15, 2016", 15 pgs.
"U.S. Appl. No. 13/645,964, Non Final Office Action dated Mar. 17, 2015", 15 pgs.
"U.S. Appl. No. 13/645,964, Notice of Allowance dated Jul. 21, 2016", 9 pgs.
"U.S. Appl. No. 13/645,964, Response filed Jun. 13, 2016 to Non Final Office Action dated Mar. 15, 2016", 11 pgs.
"U.S. Appl. No. 13/645,964, Response filed Jul. 17, 2015 to Non Final Office Action dated Mar. 17, 2015", 17 pgs.
"U.S. Appl. No. 13/645,964, Response filed Dec. 4, 2015 to Final Office Action dated Oct. 6, 2015", 14 pgs.
"U.S. Appl. No. 13/656,821, Notice of Allowance dated Jun. 18, 2015", 11 pgs.
"U.S. Appl. No. 13/656,821, Response filed May 11, 2015 to Restriction Requirement dated Mar. 10, 2015", 1 pg.
"U.S. Appl. No. 13/656,821, Restriction Requirement dated Mar. 10, 2015", 6 pgs.
"U.S. Appl. No. 13/720,648, Final Office Action dated Nov. 16, 2015", 7 pgs.

(56) References Cited

OTHER PUBLICATIONS

"U.S. Appl. No. 13/720,648, Non Final Office Action dated Jun. 10, 2015", 11 pgs.
"U.S. Appl. No. 13/720,648, Notice of Allowance dated Feb. 5, 2016", 11 pgs.
"U.S. Appl. No. 13/720,648, Response filed Jan. 13, 2016 to Final Office Action dated Nov. 16, 2015", 9 pgs.
"U.S. Appl. No. 13/720,648, Response filed May 11, 2015 to Restriction Requirement dated Mar. 10, 2015", 8 pgs.
"U.S. Appl. No. 13/720,648, Response filed Oct. 9, 2015 to Non Final Office Action dated Jun. 10, 2015", 12 pgs.
"U.S. Appl. No. 13/720,648, Restriction Requirement dated Mar. 10, 2015", 8 pgs.
"U.S. Appl. No. 13/721,970, Notice of Allowance dated Aug. 12, 2013", 13 pgs.
"U.S. Appl. No. 13/721,970, Preliminary Amendment filed Mar. 15, 2013", 13 pgs.
"U.S. Appl. No. 13/721,970, Response filed May 8, 2013 to Restriction Requirement dated Apr. 11, 2013", 1 pgs.
"U.S. Appl. No. 13/721,970, Restriction Requirement dated Apr. 11, 2013", 6 pgs.
"U.S. Appl. No. 13/751,846, Final Office Action dated Nov. 17, 2015", 9 pgs.
"U.S. Appl. No. 13/751,846, Non Final Office Action dated Jun. 15, 2015", 10 pgs.
"U.S. Appl. No. 13/751,846, Notice of Allowance dated Mar. 16, 2016", 11 pgs.
"U.S. Appl. No. 13/751,846, Notice of Allowance dated Jul. 6, 2016", 9 pgs.
"U.S. Appl. No. 13/751,846, Response filed Feb. 5, 2016 to Final Office Action dated Nov. 17, 2015", 14 pgs.
"U.S. Appl. No. 13/751,846, Response filed May 11, 2015 to Restriction Requirement dated Mar. 10, 2015", 15 pgs.
"U.S. Appl. No. 13/751,846, Response filed Oct. 9, 2015 to Non Final Office Action dated Jun. 15, 2015", 20 pgs.
"U.S. Appl. No. 13/751,846, Restriction Requirement dated Mar. 10, 2015", 7 pgs.
"U.S. Appl. No. 13/757,003, Non Final Office Action dated Jun. 25, 2015", 8 pgs.
"U.S. Appl. No. 13/757,003, Notice of Allowance dated Feb. 8, 2016", 10 pgs.
"U.S. Appl. No. 13/757,003, Response filed May 12, 2015 to Restriction Requirement dated Mar. 12, 2015", 9 pgs.
"U.S. Appl. No. 13/757,003, Response filed Oct. 26, 2015 to Non Final Office Action dated Jul. 25, 2015", 8 pgs.
"U.S. Appl. No. 13/757,003, Restriction Requirement dated Mar. 12, 2015", 6 pgs.
"U.S. Appl. No. 13/757,019, Non Final Office Action dated Jun. 25, 2015", 11 pgs.
"U.S. Appl. No. 13/757,019, Notice of Allowance dated Dec. 10, 2015", 10 pgs.
"U.S. Appl. No. 13/757,019, Response filed May 11, 2015 to Restriction Requirement dated Mar. 11, 2015", 9 pgs.
"U.S. Appl. No. 13/757,019, Response filed Oct. 26, 2015 to Non Final Office Action dated Jun. 25, 2015", 9 pgs.
"U.S. Appl. No. 13/757,019, Restriction Requirement dated Mar. 11, 2015", 10 pgs.
"U.S. Appl. No. 13/767,401, Non Final Office Action dated Aug. 26, 2015", 9 pgs.
"U.S. Appl. No. 13/767,401, Notice of Allowance dated Apr. 8, 2016", 9 pgs.
"U.S. Appl. No. 13/767,401, Notice of Allowance dated Dec. 30, 2015", 9 pgs.
"U.S. Appl. No. 13/767,401, Response filed May 18, 2015 to Restriction Requirement dated Mar. 17, 2015", 15 pgs.
"U.S. Appl. No. 13/767,401, Response filed Nov. 6, 2015 to Non Final Office Action dated Aug. 26, 2015", 12 pgs.
"U.S. Appl. No. 13/767,401, Restriction Requirement dated Mar. 17, 2015", 8 pgs.

"U.S. Appl. No. 13/790,982, Examiner Interview Summary dated Jun. 9, 2015", 3 pgs.
"U.S. Appl. No. 13/790,982, Non Final Office Action dated Sep. 16, 2015", 11 pgs.
"U.S. Appl. No. 13/790,982, Notice of Allowance dated Feb. 24, 2016", 10 pgs.
"U.S. Appl. No. 13/790,982, Response filed Jun. 2, 2015 to Restriction Requirement dated Apr. 2, 2015", 11 pgs.
"U.S. Appl. No. 13/790,982, Response filed Dec. 16, 2015 to Non Final Office Action dated Sep. 16, 2015", 10 pgs.
"U.S. Appl. No. 13/790,982, Restriction Requirement dated Apr. 2, 2015", 10 pgs.
"U.S. Appl. No. 13/790,997, Examiner Interview Summary dated Jun. 8, 2015", 3 pgs.
"U.S. Appl. No. 13/790,997, Non Final Office Action dated Sep. 21, 2015", 8 pgs.
"U.S. Appl. No. 13/790,997, Notice of Allowance dated Mar. 2, 2016", 9 pgs.
"U.S. Appl. No. 13/790,997, Response filed Jun. 2, 2015 to Restriction Requirement dated Apr. 2, 2015", 12 pgs.
"U.S. Appl. No. 13/790,997, Response filed Dec. 18, 15 to Non Final Office Action dated Sep. 21, 2015", 9 pgs.
"U.S. Appl. No. 13/790,997, Restriction Requirement dated Apr. 2, 2015", 8 pgs.
"U.S. Appl. No. 13/791,014, Non Final Office Action dated Aug. 14, 2015", 9 pgs.
"U.S. Appl. No. 13/791,014, Response filed Aug. 3, 2015 to Restriction Requirement dated May 1, 2015", 9 pgs.
"U.S. Appl. No. 13/791,014, Response filed Nov. 10, 2015 to Non Final Office Action dated Aug. 14, 2015", 13 pgs.
"U.S. Appl. No. 13/791,014, Restriction Requirement dated May 1, 2015", 6 pgs.
"U.S. Appl. No. 13/833,567, Advisory Action dated Apr. 28, 2016", 3 pgs.
"U.S. Appl. No. 13/833,567, Final Office Action dated Mar. 9, 2016", 9 pgs.
"U.S. Appl. No. 13/833,567, Non Final Office Action dated Mar. 27, 2016", 9 pgs.
"U.S. Appl. No. 13/833,567, Non Final Office Action dated Oct. 23, 2015", 10 pgs.
"U.S. Appl. No. 13/833,567, Notice of Allowance dated Sep. 27, 2016", 9 pgs.
"U.S. Appl. No. 13/833,567, Response filed Jan. 22, 2016 to Non Final Office Action dated Oct. 23, 2015", 11 pgs.
"U.S. Appl. No. 13/833,567, Response filed Apr. 20, 2016 to Final Office Action dated Mar. 9, 2016", 10 pgs.
"U.S. Appl. No. 13/833,567, Response filed Jun. 25, 2015 to Restriction Requirement dated Apr. 3, 2015", 10 pgs.
"U.S. Appl. No. 13/833,567, Response filed Aug. 4, 2016 to Non Final Office Action dated May 27, 2016", 11 pgs.
"U.S. Appl. No. 13/833,567, Restriction Requirement dated Apr. 3, 2015", 6 pgs.
"U.S. Appl. No. 13/838,755, Final Office Action dated Feb. 22, 2016", 9 pgs.
"U.S. Appl. No. 13/838,755, Non Final Office Action dated Sep. 17, 2015", 11 pgs.
"U.S. Appl. No. 13/838,755, Notice of Allowance dated Apr. 27, 2016", 7 pgs.
"U.S. Appl. No. 13/838,755, Notice of Allowance dated Aug. 3, 2016", 8 pgs.
"U.S. Appl. No. 13/838,755, Response filed Apr. 15, 2016 to Final Office Action dated Feb. 22, 2016", 11 pgs.
"U.S. Appl. No. 13/838,755, Response filed Jun. 8, 2015 to Restriction Requirement dated Apr. 6, 2015", 1 pg.
"U.S. Appl. No. 13/838,755, Response filed Dec. 1, 15 to Non Final Office Action dated Sep. 17, 2015", 13 pgs.
"U.S. Appl. No. 13/838,755, Restriction Requirement dated Apr. 6, 2015", 6 pgs.
"U.S. Appl. No. 13/889,851, Non Final Office Action dated Apr. 6, 2015", 10 pgs.
"U.S. Appl. No. 13/889,851, Notice of Allowance dated Aug. 12, 2015", 8 pgs.

(56) References Cited

OTHER PUBLICATIONS

"U.S. Appl. No. 13/889,851, Response filed Feb. 26, 2015 to Restriction Requirement dated Jan. 21, 2015", 12 pgs.
"U.S. Appl. No. 13/889,851, Response filed Jul. 6, 2015 to Non Final Office Action dated Apr. 6, 2015", 14 pgs.
"U.S. Appl. No. 13/889,851, Restriction Requirement dated Jan. 21, 2015", 6 pgs.
"U.S. Appl. No. 13/889,851, Supplemental Amendment and Response filed Jul. 6, 2015 to Non Final Office Action dated Apr. 6, 2015", 8 pgs.
"U.S. Appl. No. 13/959,145, Examiner Interview Summary dated Sep. 16, 2015", 3 pgs.
"U.S. Appl. No. 13/959,145, Final Office Action dated Jan. 29, 2016", 16 pgs.
"U.S. Appl. No. 13/959,145, Final Office Action dated Feb. 5, 2015", 22 pgs.
"U.S. Appl. No. 13/959,145, Non Final Office Action dated Jul. 31, 2015", 21 pgs.
"U.S. Appl. No. 13/959,145, Non Final Office Action dated Sep. 15, 2014", 20 pgs.
"U.S. Appl. No. 13/959,145, Notice of Allowability dated Jun. 14, 2016", 2 pgs.
"U.S. Appl. No. 13/959,145, Notice of Allowance dated Apr. 13, 2016", 5 pgs.
"U.S. Appl. No. 13/959,145, Response filed Mar. 28, 2016 to Final Office Action dated Jan. 29, 2016", 10 pgs.
"U.S. Appl. No. 13/959,145, Response filed Jul. 6, 2015 to Final Office Action dated Feb. 5, 2015", 18 pgs.
"U.S. Appl. No. 13/959,145, Response filed Oct. 30, 2015 to Non Final Office Action dated Jul. 31, 2015", 14 pgs.
"U.S. Appl. No. 13/959,145, Response filed Dec. 15, 2014 to Non Final Office Action dated Sep. 15, 2014", 21 pgs.
"U.S. Appl. No. 14/055,172, Final Office Action dated Dec. 22, 2016", 8 pgs.
"U.S. Appl. No. 14/055,172, Non Final Office Action dated Jul. 14, 2016", 12 pgs.
"U.S. Appl. No. 14/055,172, Notice of Allowance dated Mar. 29, 2017", 10 pgs.
"U.S. Appl. No. 14/055,172, Response filed Feb. 22, 2017 to Final Office Action dated Dec. 22, 2016", 11 pgs.
"U.S. Appl. No. 14/055,172, Response filed May 4, 2016 to Restriction Requirement dated Mar. 4, 2016", 8 pgs.
"U.S. Appl. No. 14/055,172, Response filed Nov. 14, 2016 to Non Final Office Action dated Jul. 14, 2016", 19 pgs.
"U.S. Appl. No. 14/055,172, Restriction Requirement dated Mar. 4, 2016", 6 pgs.
"U.S. Appl. No. 14/055,191, Non Final Office Action dated May 16, 2016", 8 pgs.
"U.S. Appl. No. 14/055,191, Notice of Allowability dated Sep. 8, 2016", 7 pgs.
"U.S. Appl. No. 14/055,191, Notice of Allowance dated Aug. 31, 2016", 13 pgs.
"U.S. Appl. No. 14/055,191, Response filed Apr. 29, 2016 to Restriction Requirement dated Mar. 7, 2016", 8 pgs.
"U.S. Appl. No. 14/055,191, Response filed Aug. 3, 2016 to Non Final Office Action dated May 16, 2016", 11 pgs.
"U.S. Appl. No. 14/055,191, Restriction Requirement dated Mar. 7, 2016", 6 pgs.
"U.S. Appl. No. 14/071,295, Non Final Office Action dated Aug. 15, 2014", 6 pgs.
"U.S. Appl. No. 14/071,295, Notice of Allowance dated Dec. 10, 2014", 8 pgs.
"U.S. Appl. No. 14/071,295, Response filed Nov. 17, 2014 to Non Final Office Action dated Aug. 15, 2014", 14 pgs.
"U.S. Appl. No. 14/071,295, Supplemental Notice of Allowability dated Jan. 26, 2015", 2 pgs.
"U.S. Appl. No. 14/094,311, Corrected Notice of Allowance dated Mar. 28, 2017", 5 pgs.
"U.S. Appl. No. 14/094,311, Notice of Allowance dated Aug. 16, 2016", 12 pgs.
"U.S. Appl. No. 14/094,311, Notice of Allowance dated Dec. 27, 2016", 8 pgs.
"U.S. Appl. No. 14/094,311, Response filed Jul. 26, 2016 to Restriction Requirement dated Jun. 22, 2016", 10 pgs.
"U.S. Appl. No. 14/094,311, Restriction Requirement dated Jun. 22, 2016", 6 pgs.
"U.S. Appl. No. 14/095,614, Non Final Office Action dated Jan. 19, 2017", 9 pgs.
"U.S. Appl. No. 14/095,614, Notice of Allowance dated May 8, 2017", 8 pgs.
"U.S. Appl. No. 14/095,614, Notice of Allowance dated Nov. 6, 2017", 9 pgs.
"U.S. Appl. No. 14/095,614, Preliminary Amendment filed Apr. 15, 2014", 17 pgs.
"U.S. Appl. No. 14/095,614, Response filed Mar. 2, 2017 to Non Final Office Action dated Jan. 19, 2017", 14 pgs.
"U.S. Appl. No. 14/095,614, Response filed Sep. 12, 2016 to Restriction Requirement dated Jul. 11, 2016", 11 pgs.
"U.S. Appl. No. 14/095,614, Restriction Requirement dated Jul. 11, 2016", 8 pgs.
"U.S. Appl. No. 14/095,639, Non Final Office Action dated Jan. 18, 2017", 10 pgs.
"U.S. Appl. No. 14/095,639, Notice of Allowance dated Apr. 13, 2017", 9 pgs.
"U.S. Appl. No. 14/095,639, Notice of Allowance dated Oct. 30, 2017", 9 pgs.
"U.S. Appl. No. 14/095,639, Response filed Mar. 2, 2017 to Non Final Office Action dated Jan. 18, 2017", 9 pgs.
"U.S. Appl. No. 14/095,639, Response filed Sep. 12, 2016 to Restriction Requirement dated Jul. 19, 2016", 7 pgs.
"U.S. Appl. No. 14/095,639, Restriction Requirement dated Jul. 19, 2016", 8 pgs.
"U.S. Appl. No. 14/107,350, Notice of Allowance dated Feb. 26, 2016", 11 pgs.
"U.S. Appl. No. 14/107,350, Notice of Allowance dated Jul. 27, 2016", 7 pgs.
"U.S. Appl. No. 14/107,350, Preliminary Amendment filed Feb. 28, 2014", 4 pgs.
"U.S. Appl. No. 14/159,094, Examiner Interview Summary dated Nov. 29, 2016", 1 pg.
"U.S. Appl. No. 14/159,094, Non Final Office Action dated Jun. 29, 2016", 15 pgs.
"U.S. Appl. No. 14/159,094, Notice of Allowance dated Nov. 29, 2016", Examiner Interview Summary dated Nov. 29, 2016 included, 11 pgs.
"U.S. Appl. No. 14/159,094, Response filed Jun. 3, 2016 to Restriction Requirement dated Apr. 20, 2016", 9 pgs.
"U.S. Appl. No. 14/159,094, Response filed Sep. 19, 2016 to Non Final Office Action dated Jun. 29, 2016", 13 pgs.
"U.S. Appl. No. 14/159,094, Restriction Requirement dated Apr. 20, 2016", 6 pgs.
"U.S. Appl. No. 14/182,038, Advisory Action dated Mar. 1, 2017", 3 pgs.
"U.S. Appl. No. 14/182,038, Final Office Action dated Dec. 19, 2016", 8 pgs.
"U.S. Appl. No. 14/182,038, Non Final Office Action dated Jul. 19, 2016", 10 pgs.
"U.S. Appl. No. 14/182,038, Notice of Allowance dated May 24, 2017", 9 pgs.
"U.S. Appl. No. 14/182,038, Response filed Feb. 20, 2017 to Final Office Action dated Dec. 19, 2016", 11 pgs.
"U.S. Appl. No. 14/182,038, Response filed Jun. 27, 2016 to Restriction Requirement dated Apr. 26, 2016", 8 pgs.
"U.S. Appl. No. 14/182,038, Response filed Oct. 19, 2016 to Non Final Office Action dated Jul. 19, 2016", 15 pgs.
"U.S. Appl. No. 14/182,038, Restriction Requirement dated Apr. 26, 2016", 7 pgs.
"U.S. Appl. No. 14/182,046, Corrected Notice of Allowance dated Jan. 20, 2017", 6 pgs.
"U.S. Appl. No. 14/182,046, Non Final Office Action dated Jul. 15, 2016", 9 pgs.
"U.S. Appl. No. 14/182,046, Notice of Allowance dated Dec. 8, 2016", 7 pgs.

(56) References Cited

OTHER PUBLICATIONS

"U.S. Appl. No. 14/182,046, Response filed Jun. 27, 2016 to Restriction Requirement dated Apr. 26, 2016", 7 pgs.
"U.S. Appl. No. 14/182,046, Response filed Oct. 17, 2016 to Non Final Office Action dated Jul. 15, 2016", 11 pgs.
"U.S. Appl. No. 14/182,046, Restriction Requirement dated Apr. 26, 2016", 6 pgs.
"U.S. Appl. No. 14/211,977, Notice of Allowance dated Jul. 12, 2016", 9 pgs.
"U.S. Appl. No. 14/211,977, Preliminary Amendment filed Mar. 2, 2016", 7 pgs.
"U.S. Appl. No. 14/211,977, Response filed Apr. 29, 2016 to Restriction Requirement dated Mar. 11, 2016", 8 pgs.
"U.S. Appl. No. 14/211,977, Restriction Requirement dated Mar. 11, 2016", 6 pgs.
"U.S. Appl. No. 14/215,550, Corrected Notice of Allowance dated Jul. 27, 2017", 2 pgs.
"U.S. Appl. No. 14/215,550, Examiner Interview Summary dated Mar. 9, 2017", 3 pgs.
"U.S. Appl. No. 14/215,550, Final Office Action dated Feb. 1, 2017", 11 pgs.
"U.S. Appl. No. 14/215,550, Non Final Office Action dated Jul. 19, 2016", 12 pgs.
"U.S. Appl. No. 14/215,550, Notice of Allowance dated Jun. 21, 2017", 8 pgs.
"U.S. Appl. No. 14/215,550, Response filed May 1, 2017 to Final Office Action dated Feb. 1, 2017", 10 pgs.
"U.S. Appl. No. 14/215,550, Response filed Jun. 22, 2016 to Restriction Requirement dated Apr. 28, 2016", 7 pgs.
"U.S. Appl. No. 14/215,550, Response filed Dec. 5, 2016 to Non Final Office Action dated Jul. 19, 2016", 13 pgs.
"U.S. Appl. No. 14/215,550, Restriction Requirement dated Apr. 28, 2016", 6 pgs.
"U.S. Appl. No. 14/275,548, Examiner Interview Summary dated May 25, 2016", 3 pgs.
"U.S. Appl. No. 14/275,548, Non Final Office Action dated Feb. 19, 2016", 14 pgs.
"U.S. Appl. No. 14/275,548, Notice of Allowance dated Jul. 27, 2016", 7 pgs.
"U.S. Appl. No. 14/275,548, Response filed May 19, 2016 to Non Final Office Action dated Feb. 19, 2016", 19 pgs.
"U.S. Appl. No. 14/324,688, Corrected Notice of Allowance dated Sep. 22, 2016", 2 pgs.
"U.S. Appl. No. 14/324,688, Non Final Office Action dated Jan. 8, 2016", 18 pgs.
"U.S. Appl. No. 14/324,688, Notice of Allowance dated Jun. 9, 2016", 7 pgs.
"U.S. Appl. No. 14/324,688, Response filed Apr. 8, 2016 to Non Final Office Action dated Jan. 8, 2016", 15 pgs.
"U.S. Appl. No. 14/456,286, Advisory Action dated Jun. 21, 2016", 3 pgs.
"U.S. Appl. No. 14/456,286, Final Office Action dated May 27, 2016", 15 pgs.
"U.S. Appl. No. 14/456,286, Non Final Office Action dated Oct. 17, 2016", 17 pgs.
"U.S. Appl. No. 14/456,286, Non Final Office Action dated Dec. 30, 2015", 16 pgs.
"U.S. Appl. No. 14/456,286, Notice of Allowance dated Feb. 15, 2017", 9 pgs.
"U.S. Appl. No. 14/456,286, Response filed Mar. 30, 2016 to Non Final Office Action dated Dec. 30, 2015", 15 pgs.
"U.S. Appl. No. 14/456,286, Response filed Jun. 13, 2016 to Final Office Action dated May 27, 2016", 10 pgs.
"U.S. Appl. No. 14/456,286, Response filed Nov. 16, 2016 to Non Final Office Action dated Oct. 17, 2016", 9 pgs.
"U.S. Appl. No. 14/456,286, Response filed Dec. 11, 2015 to Restriction Requirement dated Oct. 29, 2015", 6 pgs.
"U.S. Appl. No. 14/456,286, Restriction Requirement dated Oct. 29, 2015", 9 pgs.
"U.S. Appl. No. 14/492,590, Notice of Allowance dated Oct. 5, 2016", 10 pgs.
"U.S. Appl. No. 14/492,590, Response filed Sep. 15, 2016 to Restriction Requirement dated Jul. 25, 2015", 7 pgs.
"U.S. Appl. No. 14/492,590, Restriction Requirement dated Jul. 25, 2016", 6 pgs.
"U.S. Appl. No. 14/492,590, Supplemental Response filed Sep. 26, 2016 to Restriction Requirement dated Jul. 25, 2016", 10 pgs.
"U.S. Appl. No. 14/514,453, Non Final Office Action dated Sep. 24, 2015", 11 pgs.
"U.S. Appl. No. 14/514,453, Response filed Dec. 16, 2015 to Non Final Office Action dated Sep. 24, 2015", 14 pgs.
"U.S. Appl. No. 14/589,101, Advisory Action dated Feb. 21, 2017", 5 pgs.
"U.S. Appl. No. 14/589,101, Examiner Interview Summary dated Jan. 30, 2017", 3 pgs.
"U.S. Appl. No. 14/589,101, Final Office Action dated Feb. 22, 2018", 15 pgs.
"U.S. Appl. No. 14/589,101, Final Office Action dated Oct. 2, 2015", 10 pgs.
"U.S. Appl. No. 14/589,101, Final Office Action dated Nov. 16, 2016", 12 pgs.
"U.S. Appl. No. 14/589,101, Non Final Office Action dated Feb. 12, 2015", 10 pgs.
"U.S. Appl. No. 14/589,101, Non Final Office Action dated May 5, 2016", 14 pgs.
"U.S. Appl. No. 14/589,101, Non Final Office Action dated Sep. 14, 2017", 13 pgs.
"U.S. Appl. No. 14/589,101, Response filed Jan. 23, 2017 to Final Office Action dated Nov. 16, 2016", 9 pgs.
"U.S. Appl. No. 14/589,101, Response filed Jun. 12, 2015 to Non Final Office Action dated Feb. 12, 2015", 11 pgs.
"U.S. Appl. No. 14/589,101, Response filed Nov. 13, 2017 to Non Final Office Action dated Sep. 14, 2017", 10 pgs.
"U.S. Appl. No. 14/589,101, Response filed Dec. 29, 2015 to Final Office Action dated Oct. 2, 2015", 15 pgs.
"U.S. Appl. No. 14/589,191, Response filed Aug. 5, 2016 to Non Final Office Action dated May 5, 2016", 16 pgs.
"U.S. Appl. No. 14/594,285, Final Office Action dated May 22, 2017", 12 pgs.
"U.S. Appl. No. 14/594,285, Non Final Office Action dated Jan. 11, 2017", 15 pgs.
"U.S. Appl. No. 14/594,285, Notice of Allowance dated Jun. 27, 2017", 10 pgs.
"U.S. Appl. No. 14/594,285, Response filed Apr. 11, 2017 to Non Final Office Action mailed 01-11-17", 12 pgs.
"U.S. Appl. No. 14/594,285, Response filed Jun. 14, 2017 to Final Office Action dated May 22, 2017", 9 pgs.
"U.S. Appl. No. 14/594,285, Response filed Dec. 14, 2016 to Restriction Requirement dated Nov. 7, 2016", 8 pgs.
"U.S. Appl. No. 14/594,285, Restriction Requirement dated Nov. 7, 2016", 6 pgs.
"U.S. Appl. No. 14/599,909, Non Final Office Action dated Jul. 27, 2017", 18 pgs.
"U.S. Appl. No. 14/599,909, Notice of Allowance dated Feb. 13, 2018", 9 pgs.
"U.S. Appl. No. 14/599,909, Response filed Sep. 21, 2017 to Non Final Office Action dated Jul. 27, 2017", 10 pgs.
"U.S. Appl. No. 14/635,055, Non Final Office Action dated Aug. 28, 2017", 8 pgs.
"U.S. Appl. No. 14/635,055, Notice of Allowance dated Feb. 28, 2018", 11 pgs.
"U.S. Appl. No. 14/635,055, Response filed Jun. 27, 2017 to Restriction Requirement dated Apr. 27, 2017", 11 pgs.
"U.S. Appl. No. 14/635,055, Response filed Nov. 28, 2017 to Non Final Office Action dated Aug. 28, 2017", 13 pgs.
"U.S. Appl. No. 14/635,055, Restriction Requirement dated Apr. 27, 2017", 7 pgs.
"U.S. Appl. No. 14/697,140, Advisory Action dated Aug. 11, 2017", 3 pgs.
"U.S. Appl. No. 14/697,140, Final Office Action dated Jun. 30, 2017", 13 pgs.

(56) References Cited

OTHER PUBLICATIONS

"U.S. Appl. No. 14/697,140, Final Office Action dated Sep. 23, 2016", 10 pgs.
"U.S. Appl. No. 14/697,140, Non Final Office Action dated Jan. 10, 2017", 12 pgs.
"U.S. Appl. No. 14/697,140, Non Final Office Action dated Apr. 8, 2016", 8 pgs.
"U.S. Appl. No. 14/697,140, Notice of Allowance dated Sep. 5, 2017", 7 pgs.
"U.S. Appl. No. 14/697,140, Response filed Mar. 1, 2017 to Non Final Office Action dated Jan. 10, 2017", 11 pgs.
"U.S. Appl. No. 14/697,140, Response filed Jun. 13, 2016 to Non Final Office Action dated Apr. 8, 2016", 10 pgs.
"U.S. Appl. No. 14/697,140, Response filed Jul. 27, 2017 to Final Office Action dated Jun. 30, 2017", 10 pgs.
"U.S. Appl. No. 14/697,140, Response filed Nov. 16, 2016 to Final Office Action dated Sep. 23, 2016", 13 pgs.
"U.S. Appl. No. 14/794,309, Final Office Action dated Mar. 20, 2017", 18 pgs.
"U.S. Appl. No. 14/794,309, Non Final Office Action dated Jun. 20, 2017", 16 pgs.
"U.S. Appl. No. 14/794,309, Non Final Office Action dated Nov. 22, 2016", 13 pgs.
"U.S. Appl. No. 14/794,309, Notice of Allowance dated Sep. 18, 2017", 5 pgs.
"U.S. Appl. No. 14/794,309, Preliminary Amendment filed Sep. 22, 2015", 6 pgs.
"U.S. Appl. No. 14/794,309, Response filed Feb. 22, 2017 to Non Final Office Action dated Nov. 22, 2016", 12 pgs.
"U.S. Appl. No. 14/794,309, Response filed May 22, 2017 to Final Office Action dated Mar. 20, 2017", 13 pgs.
"U.S. Appl. No. 14/794,309, Response filed Aug. 17, 2017 to Non Final Office Action dated Jun. 20, 2017", 12 pgs.
"U.S. Appl. No. 14/794,309, Supplemental Preliminary Amendment filed Mar. 3, 2016", 8 pgs.
"U.S. Appl. No. 14/854,308, Notice of Allowance dated Mar. 16, 2018", 11 pgs.
"U.S. Appl. No. 14/854,308, Response filed Dec. 20, 2017 to Restriction Requirement dated Oct. 20, 2017", 8 pgs.
"U.S. Appl. No. 14/854,308, Restriction Requirement dated Oct. 20, 2017", 8 pgs.
"U.S. Appl. No. 14/854,308, Supplemental Preliminary Amendment Filed Aug. 31, 2017", 3 pgs.
"U.S. Appl. No. 14/876,167, Non Final Office Action dated Mar. 13, 2018", 8 pgs.
"U.S. Appl. No. 14/876,167, Preliminary Amendment filed Oct. 27, 2015", 8 pgs.
"U.S. Appl. No. 14/876,167, Restriction Requirement dated Nov. 22, 2017", 9 pgs.
"U.S. Appl. No. 14/936,831, Preliminary Amendment filed Nov. 11, 2015", 6 pgs.
"U.S. Appl. No. 14/936,831, Response filed Jan. 10, 2018 to Restriction Requirement dated Nov. 22, 2017", 6 pgs.
"U.S. Appl. No. 14/936,831, Restriction Requirement dated Nov. 22, 2017", 8 pgs.
"U.S. Appl. No. 14/956,724, Examiner Interview Summary dated Jun. 20, 2017", 3 pgs.
"U.S. Appl. No. 14/956,724, Non Final Office Action dated Mar. 31, 2017", 17 pgs.
"U.S. Appl. No. 14/956,724, Notice of Allowance dated Aug. 23, 2017", 9 pgs.
"U.S. Appl. No. 14/956,724, Preliminary Amendment filed Dec. 7, 2015", 8 pgs.
"U.S. Appl. No. 14/956,724, Response filed Jun. 16, 2017 to Non Final Office Action dated Mar. 31, 2017", 12 pgs.
"U.S. Appl. No. 14/956,724, Supplemental Preliminary Amendment filed Feb. 11, 2016", 7 pgs.
"U.S. Appl. No. 14/956,724, Supplemental Preliminary Amendment filed Oct. 3, 2016", 8 pgs.
"U.S. Appl. No. 14/983,108, Preliminary Amendment filed Dec. 30, 2015", 7 pgs.
"U.S. Appl. No. 14/983,108, Response filed Jan. 24, 2018 to Restriction Requirement dated Dec. 4, 2017", 6 pgs.
"U.S. Appl. No. 14/983,108, Restriction Requirement dated Dec. 4, 2017", 7 pgs.
"U.S. Appl. No. 14/983,747, Preliminary Amendment filed Jan. 4, 2016", 5 pgs.
"U.S. Appl. No. 14/983,747, Response filed Jan. 24, 2018 to Restriction Requirement dated Dec. 20, 2017", 5 pgs.
"U.S. Appl. No. 14/983,747, Restriction Requirement dated Dec. 20, 2017", 7 pgs.
"U.S. Appl. No. 15/060,007, Preliminary Amendment filed Mar. 9, 2016", 9 pgs.
"U.S. Appl. No. 15/061,352, Corrected Notice of Allowance dated Feb. 12, 2018", 2 pgs.
"U.S. Appl. No. 15/061,352, Non Final Office Action dated Nov. 17, 2017", 6 pgs.
"U.S. Appl. No. 15/061,352, Notice of Allowance dated Jan. 19, 2018", 10 pgs.
"U.S. Appl. No. 15/061,352, Preliminary Amendment filed Mar. 7, 2016", 8 pgs.
"U.S. Appl. No. 15/061,352, Response filed Dec. 12, 2017 to Non Final Office Action dated Nov. 17, 2017", 9 pgs.
"U.S. Appl. No. 15/074,553, Corrected Notice of Allowance dated Feb. 12, 2018", 2 pgs.
"U.S. Appl. No. 15/074,553, Non Final Office Action dated Nov. 17, 2017", 6 pgs.
"U.S. Appl. No. 15/074,553, Notice of Allowance dated Jan. 19, 2018", 10 pgs.
"U.S. Appl. No. 15/074,553, Preliminary Amendment filed Mar. 21, 2016", 8 pgs.
"U.S. Appl. No. 15/074,553, Response filed Dec. 12, 2017 to Non Final Office Action dated Nov. 17, 2017", 8 pgs.
"U.S. Appl. No. 15/131,663, Preliminary Amendment filed Dec. 21, 2016", 6 pgs.
"U.S. Appl. No. 15/166,480, Supplemental Preliminary Amendment filed Jul. 18, 2017", 7 pgs.
"U.S. Appl. No. 15/200,546, Preliminary Amendment filed Dec. 21, 2016", 6 pgs.
"U.S. Appl. No. 15/278,777, Non Final Office Action dated Feb. 28, 2018", 14 pgs.
"U.S. Appl. No. 15/278,777, Preliminary Amendment filed Oct. 3, 2016", 7 pgs.
"U.S. Appl. No. 15/288,183, Preliminary Amendment filed Oct. 31, 2016", 7 pgs.
"U.S. Appl. No. 15/288,183, Supplemental Preliminary Amendment filed Jul. 27, 2017", 7 pgs.
"U.S. Appl. No. 15/294,994, Preliminary Amendment filed Jan. 25, 2017", 8 pgs.
"U.S. Appl. No. 15/294,994, Supplemental Preliminary Amendment filed May 31, 2017", 6 pgs.
"U.S. Appl. No. 15/297,844, Preliminary Amendment filed Oct. 20, 2016", 7 pgs.
"U.S. Appl. No. 15/297,844, Supplemental Preliminary Amendment filed Jan. 25, 2018", 6 pgs.
"U.S. Appl. No. 15/332,590, Preliminary Amendment filed Nov. 22, 2016", 5 pgs.
"U.S. Appl. No. 15/361,917, Preliminary Amendment filed Nov. 30, 2016", 6 pgs.
"U.S. Appl. No. 15/401,768, Preliminary Amendment filed Mar. 23, 2017", 6 pgs.
"U.S. Appl. No. 15/401,768, Supplemental Preliminary Amendment filed Jun. 22, 2017", 7 pgs.
"U.S. Appl. No. 15/412,676, Preliminary Amendment filed Jul. 3, 2017", 7 pgs.
"U.S. Appl. No. 15/455,895, Preliminary Amendment filed Mar. 13, 2017", 6 pgs.
"U.S. Appl. No. 15/461,675, Preliminary Amendment filed Jun. 24, 2017", 6 pgs.
"U.S. Appl. No. 15/622,718, Preliminary Amendment filed Jun. 15, 2017", 7 pgs.

(56) References Cited

OTHER PUBLICATIONS

"U.S. Appl. No. 15/626,384, Preliminary Amendment filed Aug. 10, 2018", 11 pgs.
"U.S. Appl. No. 15/654,386, Preliminary Amendment filed Aug. 30, 2017", 11 pgs.
"U.S. Appl. No. 15/662,572, Preliminary Amendment filed Jul. 31, 2017", 7 pgs.
"U.S. Appl. No. 15/664,572, Preliminary Amendment filed Aug. 3, 2017", 7 pgs.
"U.S. Appl. No. 15/682,187, Preliminary Amendment filed Sep. 7, 2017", 6 pgs.
"U.S. Appl. No. 15/703,727, Preliminary Amendment filed Sep. 14, 2017", 7 pgs.
"U.S. Appl. No. 15/715,731, Preliminary Amendment Filed Sep. 26, 2017", 9 pgs.
"U.S. Appl. No. 15/715,731, Supplemental Preliminary Amendment filed Dec. 29, 2017", 8 pgs.
"U.S. Appl. No. 15/720,997, Preliminary Amendment filed Oct. 2, 2017", 6 pgs.
"U.S. Appl. No. 15/793,216, Preliminary Amendment filed Oct. 26, 2017", 8 pgs.
"U.S. Appl. No. 15/865,938, Preliminary Amendment filed Jan. 10, 2018", 7 pgs.
"U.S. Appl. No. 15/866,089, Preliminary Amendment filed Jan. 10, 2018", 10 pgs.
"U.S. Appl. No. 15/886,712, Preliminary Amendment filed Feb. 2, 2018", 8 pgs.
"U.S. Appl. No. 15/891,049, Preliminary Amendment filed Feb. 8, 2018", 6 pgs.
"U.S. Appl. No. 15/903,261, Preliminary Amendment filed Feb. 28, 2018", 6 pgs.
"U.S. Appl. No. 15/917,143, Preliminary Amendment filed Mar. 14, 2018", 7 pgs.
"Arthroscopic Meniscal Repair using the Meniscal Cinch™", Surgical Technique brochure. Arthrex®, 6 sheets, (2008), 6 sheets.
"Australian Application Serial No. 2014236885, First Examination Report dated Dec. 11, 2017", 2 pgs.
"Australian Application Serial No. 2014236885, Response filed Feb. 14, 2018 to First Examination Report dated Dec. 11, 2017", 6 pgs.
"Bio-Intrafix Tibial Soft Tissue Fastener, Building on the Legacy of IntraFix", DePuy Mitek brochure, (Feb. 2007), 6 pgs.
"Biomechanical Evaluation of the Biomet Sports Medicine JurggerKnot™ Soft Anchor in Porcine Bone", Study completed Jan. 2010. Biomet Sports Medicine Research and Develo ment, Warsaw, Indiana, (Jan. 2010), 2 pgs.
"Chinese Application Serial No. 201480027708.4, Office Action dated Feb. 14, 2017", (W/ English Translation), 18 pgs.
"Chinese Application Serial No. 201480027708.4, Office Action dated May 26, 2016", W/ English Translation, 15 pgs.
"Chinese Application Serial No. 201480027708.4, Office Action dated Aug. 18, 2017", (W/ English Translation), 8 pgs.
"Chinese Application Serial No. 201480027708.4, Response filed May 2, 2017 to Office Action dated Feb. 14, 2017", (W/ English Translation), 17 pgs.
"Chinese Application Serial No. 201480027708.4, Response filed Oct. 10, 2016 to Office Action dated May 26, 2016", (W/ English Translation of Claims), 14 pgs.
"Chinese Application Serial No. 201480027708.4, Response filed Oct. 31, 2017 to Office Action dated Aug. 18, 2017", With English Claims, 7 pgs.
"Declaration of John White regarding PSCD and Customized Device and Exhibits 1-5".
"Do your next distal tendon repair with . . . The Lubbers Technique", Teno Fix@ brochure, Ortheon® Medical, (2003), 2 pgs.
"European Application No. 16168202.6, Extended European Search Report dated Aug. 16, 2017", 11 pgs.
"European Application No. 16168202.6, Response filed Nov. 3, 2017 to Extended European Search Report dated Aug. 16, 2017", 9 pgs.
"European Application Serial No. 10727548.9, Examination Notification Art. 94(3) dated Sep. 18, 2014", 6 pgs.
"European Application Serial No. 10727548.9, Office Action dated Jan. 11, 2016", 6 pgs.
"European Application Serial No. 10727548.9, Office Action dated Jan. 19, 2012", 2 pgs.
"European Application Serial No. 10727548.9, Response filed Mar. 19, 2015 to Examination Notification Art. 94(3) dated Sep. 18, 2014", 23 pgs.
"European Application Serial No. 11707316.3, Examination Notification Art. 94(3) dated Feb. 4, 2014", 3 pgs.
"European Application Serial No. 11707316.3, Examination Notification Art. 94(3) dated Dec. 17, 2014", 5 pgs.
"European Application Serial No. 11707316.3, Office Action dated Nov. 10, 2015", 6 pgs.
"European Application Serial No. 11707316.3, Response filed Jun. 5, 2014 to Examination Notification Art. 94(3) Serial Feb. 4, 2014", 7 pgs.
"European Application Serial No. 11707316.3, Response filed Jun. 29, 2015 to Examination Notification Art. 94(3) dated Dec. 17, 2014", 25 pgs.
"European Application Serial No. 12721676.0, Communication pursuant to Article 94(3) EPC dated Sep. 30, 2015", 4 pgs.
"European Application Serial No. 12721676.0, Office Action dated Jan. 3, 2014", 2 pgs.
"European Application Serial No. 12721676.0, Preliminary Amendment filed Nov. 19, 2013", 9 pgs.
"European Application Serial No. 12721676.0, Response filed Apr. 11, 2016 to Communication pursuant to Article 94(3) EPC dated Sep. 30, 2015", 38 pgs.
"European Application Serial No. 12721676.0, Response filed Jul. 10, 2014 to Office Action dated Jan. 3, 2014", 2 pgs.
"European Application Serial No. 12791902.5, Examination Notification Art. 94(3) dated Aug. 14, 2015", 4 pgs.
"European Application Serial No. 12791902.5, Office Action dated Jul. 15, 2014", 2 pgs.
"European Application Serial No. 12791902.5, Response filed Feb. 23, 2016 to Examination Notification Art. 94(3) dated Aug. 14, 2015", 12 pgs.
"European Application Serial No. 12806211.4, Examination Notification Art. 94(3) dated Aug. 13, 2015", 5 pgs.
"European Application Serial No. 12806211.4, Office Action dated Jul. 18, 2014", 2 pgs.
"European Application Serial No. 12806211.4, Response filed Feb. 23, 2016 to Communication Pursuant to Article 94(3) EPC dated Aug. 13, 2015", 11 pgs.
"European Application Serial No. 13818131.8, Office Action dated Jul. 28, 2015", 2 pgs.
"European Application Serial No. 13818131.8, Response filed Feb. 8, 2016 to Office Action dated Jul. 28, 2015", 14 pgs.
"European Application Serial No. 14716173.1, Office Action dated Nov. 5, 2015", 2 pgs.
"European Application Serial No. 14716173.1, Response filed May 16, 2016 to Communication pursuant to Rules 161(1) and 162 EPC dated Nov. 5, 2015", 10 pgs.
"European Application Serial No. 14716173.1, Response filed Sep. 25, 2017 to Office Action dated Mar. 14, 2017", 12pgs.
"European Application Serial No. 16168202.6, Partial European Search Report dated May 9, 2017", 12 pgs.
"European Application Serial No. 12806211.4, Communication Pursuant to Article 94(3) EPC dated Jun. 23, 2016", 4 pgs.
"EZ Loc Femoral Fixation Device", copyright 2005 Arthrotek, Inc, (2005), 8 pgs.
"International Application Serial No. PCT/US2009/039580, International Preliminary Report on Patentability dated Nov. 4, 2010", 9 pgs.
"International Application Serial No. PCT/US2009/039580, International Search Report dated Jul. 30, 2009", 4 pgs.
"International Application Serial No. PCT/US2009/039580, Written Opinion dated Jul. 30, 2009", 7 pgs.
"International Application Serial No. PCT/US2010/036602, International Preliminary Report on Patentability dated Dec. 8, 2011", 9 pgs.

(56) References Cited

OTHER PUBLICATIONS

"International Application Serial No. PCT/US2010/036602, International Search Report dated Nov. 8, 2010", 6 pgs.

"International Application Serial No. PCT/US2010/036602, Written Opinion dated Nov. 8, 2010", 7 pgs.

"International Application Serial No. PCT/US2011/026349, International Preliminary Report on Patentability dated Sep. 20, 2012", 11 pgs.

"International Application Serial No. PCT/US2011/026349, International Search Report dated Jul. 28, 2011", 6 pgs.

"International Application Serial No. PCT/US2011/026349, Invitation to Pay Additional Fees dated Jun. 9, 2011", 5 pgs.

"International Application Serial No. PCT/US2011/026349, Written Opinion dated Jul. 28, 2011", 9 pgs.

"International Application Serial No. PCT/US2011/038188, International Preliminary Report on Patentability dated Dec. 6, 2012", 14 pgs.

"International Application Serial No. PCT/US2011/038188, International Search Report dated Oct. 14, 2011", 6 pgs.

"International Application Serial No. PCT/US2011/038188, Invitation to Pay Additional Fees dated Aug. 5, 2011", 5 pgs.

"International Application Serial No. PCT/US2011/038188, Written Opinion dated Oct. 14, 2011", 12 pgs.

"International Application Serial No. PCT/US2012/030294, International Preliminary Report on Patentability dated Oct. 10, 2013", 9 pgs.

"International Application Serial No. PCT/US2012/030294, International Search Report dated May 23, 2012", 6 pgs.

"International Application Serial No. PCT/US2012/030294, Written Opinion dated May 23, 2012", 7 pgs.

"International Application Serial No. PCT/US2012/037703, International Preliminary Report on Patentability dated Nov. 28, 2013", 10 pgs.

"International Application Serial No. PCT/US2012/037703, International Search Report dated Sep. 21, 2012", 6 pgs.

"International Application Serial No. PCT/US2012/037703, Written Opinion dated Sep. 21, 2012", 8 pgs.

"International Application Serial No. PCT/US2012/062738, International Preliminary Report on Patentability dated May 15, 2014", 9 pgs.

"International Application Serial PCT/US2012/062738, International Search Report dated Mar. 6, 2013", 6 pgs.

"International Application Serial No. PCT/US2012/062738, Written Opinion dated Mar. 6, 2013", 7 pgs.

"International Application Serial No. PCT/US2012/064832, International Preliminary Report on Patentability dated May 30, 2014", 9 pgs.

"International Application Serial No. PCT/US2012/064832, International Search Report dated Feb. 6, 2013", 3 pgs.

"International Application Serial No. PCT/US2012/064832, Written Opinion dated Feb. 6, 2013", 7 pgs.

"International Application Serial No. PCT/US2013/075989, International Preliminary Report on Patentability dated Jul. 2, 2015", 10 pgs.

"International Application Serial No. PCT/US2013/075989, International Search Report dated Mar. 6, 2014", 4 pgs.

"International Application Serial No. PCT/US2013/075989, Written Opinion dated Mar. 6, 2014", 7 pgs.

"International Application Serial No. PCT/US2014/026413, International Preliminary Report on Patentability dated Sep. 24, 2015", 10 pgs.

"International Application Serial No. PCT/US2014/026413, International Search Report dated Jun. 6, 2014", 5 pgs.

"International Application Serial No. PCT/US2014/026413, Written Opinion dated Jun. 6, 2014", 8 pgs.

"JuggerKnot™ Soft Anchor Midfoot Repair", brochure. Biomet Sports Medicine, (Jul. 2011), 12 pgs.

"JuggerKnot™ Soft Anchor. It's Small. It's strong. And it's all suture . . . ", Ordering Information brochure. Biomet Sports Medicine, (Jun. 2011), 2 pgs.

"JuggerKnot™ Soft Anchor. Labral Repair", brochure. Biomet Sports Medicine, (Apr. 2011), 12 pgs.

"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique", brochure, Biomet® Sports Medicine, (2013), 16 pgs.

"Make your next tendon repair an open-and-shut case. The Teno Fix® Tendon Repair System", Teno Fix® brochure, Ortheon® Medical, (2003), 2 pgs.

"Mallory-Head Modular Calcar Revision System", Biomet Orthopedics, Inc., (2006), 20 pgs.

"Next Generation in Knee Ligament Reconstruction & Repair Technology", Suture Tensioner w/Tensiometer, Arthrex®, Inc. catalog, (2009).

"PANALOK Anchor with PDS II and ETHIBOND Suture", Mitek Products ETHICON, (1997), 2 pgs.

"Rapid Sternal Closure", KLS Martin L.P., [Online] retrieved from the internet: U.S. Appl. No. 13/645,964 , (2006).

"Rotator Cuff Fixation", Acufex Fastenator System: Shoulder Arthroscopy, H-2-H-22.

"SE Graft Tensioning System Surgical Technique", Linvatec Corporation copyright 2003, (2004), 12 pgs.

"SportMesh™ Soft Tissue Reinforcment, Made from . . . Artelon® optimal tissue repair", Biomet® Sports Medicine, Inc., (2007), 8 pgs.

"Sternal Cable System", Pioneer®, [Online] retrieved from the internet: U.S. Appl. No. 13/645,964 , (2010).

"The AutoCuff System", Opus Medical, [Online]. Retrieved from the Internet: <www.opusmedical.com>, (2003), 4 pgs.

"Toggleloc™ Femoral Fixation Device", Arthrotek, (Mar. 31, 2006), 8 pgs.

"TriTis™ Tibial Fixation System and Implant", brochure. Scandius Biomedical, (2006).

Albritton, Mark J, et al., "Toggleloc Fixation Device with Ziploop Technology: Biceps Tendon Reattachment", Biomet Sports Medicine, a Biomet Company Brochure 2099, (2011), 1-12.

Alford, J Winslow, et al., "Cartilage Restoration, Part 1. Basic Science, Historical Perspective, Patient Evaluation, and Treatment Options", The American Journal of Sports Medicine, 33(2), (2005), 295-306.

Andrews, James R, "Toggleloc™ Fixation Device with Ziploop™ Technology: ACL Reconstruction Bone-Tendon-Bone", Biomet Sports Medicine, a Biomet Company Brochure, (2013), 1-20.

Anitua, Eduardo, et al., "Autologous platelets as a source of proteins for healing and tissue regeneration", Thromb Haemost, vol. 91, (2004), 4-15.

Arthrotek, "A Biomet Company; Sure fire Hybrid Meniscal Device", Fall AANA, (2004), 37 pgs.

Barber, Alan F, "Uses and Abuses of Sutures and Anchors", Shoulder Scope, San Diego Shoulder Arthroscopy Library, (Jul. 1999), 6 pgs.

Barber, Alan F, "Using Sutures and Anchors", San Diego Shoulder Arthroscopy Course, 17th Annual Meetina, (Jun. 14, 2000), 9 pgs.

Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.

Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.

Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.

Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.

Fromm, Stuart M.D. E, "", Rapidloc, Meniscal Repair System, Mitek Products, Ethicon, (2001), 6 pgs.

Haynesworth, S E, et al., "Mitogenic Stimulation of Human Mesenchymal Stem Cells by Platelet Releasate Suggests a Mecha-

(56) References Cited

OTHER PUBLICATIONS nism for Enhancement of Bone Repair by Platelet Concentrate", 48th Annual Meeting of the Orthopaedic Research Society Poster No. 0462, (2002), 1 pg.
Hecker, AT, et al., "Pull-out strength of suture anchors for rotator cuff and Bankart lesion repairs", The American Journal of Sports Medicine 21(6), (1993), 874-879.
Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.
Lawhorn, M D, et al., "MaxFire™ Meniscal Repair Device with Zip Loop™ Technology", Biomet Sports Medicine, (Feb. 29, 2008), 12 pgs.
Majors, MD, Roy Alan, "Meniscal repairs: proven techniques and current trends", Lippincott Williams & Wilkins, Inc.;, (2002), 30-36.
Miller, Mark D, et al., "Pitfalls Associated with FasT-Fix Meniscal Repair", Arthroscopy: The Journal of Arthroscopic and Related Surgery, vol. 18 No. 8 :, (Oct. 2002), 939-943.
Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.
Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.
Roseberg, MD, Thomas D, "ACL Reconstruction with Acufex Director Drill Guide and Endobutton CL Fixation System", Smith & Nephew: Knee Series, Technique Guide, (2005), 12 pgs.
Saxena, Pankaj, et al., "Use of Double Wires in Sternal Closure, A Useful Technique", Texas Heart® Institute. Journal List> Tex Heart Inst J > v.33(4), (2006).
Smith, et al., "Endoscopic Meniscal Repair Using the T-Fix", (1996), 16 pgs.
Smith, et al., "Fast-Fix", Meniscal Repair System;, (2001), 3 pgs.
Steadman, et al., "Microfracture: Surgical Technique and Rehabilitation to Treat Chondral Defects", Clinical Orthopaedics and Related Research 391, (2001), S362-S369.
Thomas, Roseberg D, "Technique for ACL Reconstruction with Acufex Director Drill Guide and Endobutton CL", Smith & Nephew, Technique Guide, (1999), 18 pgs.
Weiler, A, et al., "Biodegradierbare Interferenzschrauben in der Kreuzbandchirurgie", Opjournal 14, (1998), 278-284.
Zeitani, Jacob M.D, "A New Sternal Reinforcement Device to Prevent and Treat Sternal Dehiscence", CTSNet, [Online]. Retrieved from the Internet: <URL: http://www.ctsnet.org/print/article/new-sternal-reinforcement-device-prevent-and-treat-sternal-dehiscence>, (Jun. 30, 2008), 6 pgs.
"U.S. Appl. No. 15/720,997, Advisory Action dated Oct. 13, 2020", 2 pgs.
"U.S. Appl. No. 15/720,997, Final Office Action dated Aug. 4, 2020", 10 pgs.
"U.S. Appl. No. 15/720,997, Response filed Sep. 30, 2020 to Final Office Action dated Aug. 4, 2020", 11 pgs.
"U.S. Appl. No. 15/866,089, Corrected Notice of Allowability dated Aug. 27, 2020", 2 pgs.
"U.S. Appl. No. 15/866,089, Notice of Allowance dated Jul. 15, 2020", 5 pgs.
"U.S. Appl. No. 15/891,049, Examiner Interview Summary dated Aug. 10, 2020", 3 pgs.
"U.S. Appl. No. 15/891,049, Final Office Action dated Nov. 10, 2020", 10 pgs.
"U.S. Appl. No. 15/891,049, Non Final Office Action dated Jul. 14, 2020", 16 pgs.
"U.S. Appl. No. 15/891,049, Response filed Aug. 17, 2020 to Non Final Office Action dated Jul. 14, 2020", 18 pgs.
"U.S. Appl. No. 15/917,143, Non Final Office Action dated Aug. 7, 2020", 6 pgs.
"U.S. Appl. No. 15/917,143, Response filed Oct. 29, 2020 to Non Final Office Action dated Aug. 7, 2020", 11 pgs.
"U.S. Appl. No. 15/945,425, Non Final Office Action Aug. 25, 2020", 11 pgs.
"U.S. Appl. No. 15/945,425, Response filed Jun. 24, 2020 to Restriction Requirement dated May 19, 2020", 7 pgs.
"U.S. Appl. No. 15/956,444, Response filed Sep. 14, 2020 to Restriction Requirement dated Jul. 14, 2020", 8 pgs.
"U.S. Appl. No. 15/956,444, Restriction Requirement dated Jul. 14, 2020", 7 pgs.
"U.S. Appl. No. 15/972,646, Response filed Sep. 21, 2020 to Restriction Requirement dated Jul. 27, 2020", 7 pgs.
"U.S. Appl. No. 15/972,646, Restriction Requirement dated Jul. 27, 2020", 6 pgs.
"U.S. Appl. No. 16/251,342, Supplemental Preliminary Amendment filed Oct. 28, 2020", 7 pgs.
"U.S. Appl. No. 16/251,342, Supplemental Preliminary Amendment filed Nov. 4, 2020", 7 pgs.
"U.S. Appl. No. 16/255,300 Supplemental Preliminary Amendment Filed Nov. 12, 2020", 8 pgs.
"U.S. Appl. No. 16/544,293, Supplemental Preliminary Amendment filed Oct. 28, 2020", 6 pgs.
"U.S. Appl. No. 16/593,022, Supplemental Preliminary Amendment filed Oct. 21, 2020", 8 pgs.
"U.S. Appl. No. 16/989,386, Supplemental Preliminary Amendment filed Oct. 21, 2020", 8 pgs.
"European Application Serial No. 14716173.1, Communication Pursuant to Article 94(3) EPC dated Jul. 13, 2020", 4 pgs.
"U.S. Appl. No. 13/288,459, Examiner Interview Summary dated Jan. 11, 2016", 1 pg.
"U.S. Appl. No. 13/311,936, PTO Response to Rule 312 Communication dated May 10, 2016", 2 pgs.
"U.S. Appl. No. 13/609,389, 312 Amendment filed Sep. 15, 2014", 4 pgs.
"U.S. Appl. No. 13/609,389, Examiner Interview Summary dated Feb. 4, 2014", 4 pgs.
"U.S. Appl. No. 13/609,389, Final Office Action dated May 5, 2014", 14 pgs.
"U.S. Appl. No. 13/609,389, Non Final Office Action dated Nov. 27, 2013", 12 pgs.
"U.S. Appl. No. 13/609,389, Notice of Allowance dated Jul. 23, 2014", 5 pgs.
"U.S. Appl. No. 13/609,389, PTO Response to Rule 312 Communication dated Oct. 16, 2014", 2 pgs.
"U.S. Appl. No. 13/609,389, Response filed Feb. 27, 2014 to Non Final Office Action dated Nov. 27, 2013", 18 pgs.
"U.S. Appl. No. 13/609,389, Response filed Jul. 10, 2014 to Final Office Action dated May 5, 2014", 12 pgs.
"U.S. Appl. No. 13/720,631, Final Office Action dated Jun. 25, 2014", 10 pgs.
"U.S. Appl. No. 13/720,631, Non Final Office Action dated Mar. 6, 2014", 7 pgs.
"U.S. Appl. No. 13/720,631, Notice of Allowance dated Jul. 25, 2014", 5 pgs.
"U.S. Appl. No. 13/720,631, Response filed Jun. 6, 2014 to Non Final Office Action dated Mar. 6, 2014", 11 pgs.
"U.S. Appl. No. 13/720,631, Response filed Jul. 14, 2014 to Final Office Action dated Jun. 25, 2014", 6 pgs.
"U.S. Appl. No. 13/720,631, Supplemental Notice of Allowance dated Sep. 8, 2014", 2 pgs.
"U.S. Appl. No. 13/791,014, Final Office Action dated Jan. 8, 2016", 11 pgs.
"U.S. Appl. No. 13/791,014, Notice of Allowability dated Jul. 27, 2017", 2 pgs.
"U.S. Appl. No. 13/791,014, Notice of Allowance dated Jan. 10, 2017", 15 pgs.
"U.S. Appl. No. 13/791,014, Notice of Allowance dated Apr. 27, 2017", 8 pgs.
"U.S. Appl. No. 13/791,014, Response filed Jun. 6, 2016 to Final Office Action dated Jan. 8, 2016", 13 pgs.
"U.S. Appl. No. 14/514,453, Final Office Action dated Mar. 17, 2016", 17 pgs.

(56) References Cited

OTHER PUBLICATIONS

"U.S. Appl. No. 14/532,333, Response filed Apr. 7, 2016 to Restriction Requirement dated Feb. 8, 2016", 10 pgs.
"U.S. Appl. No. 14/532,333, Restriction Requirement dated Feb. 8, 2016", 6 pgs.
"U.S. Appl. No. 14/589,101, Advisory Action dated May 22, 2018", 3 pgs.
"U.S. Appl. No. 14/589,101, Response filed Apr. 10, 2018 to Final Office Action dated Feb. 22, 2018", 10 pgs.
"U.S. Appl. No. 14/876,167, Response filed Jan. 9, 2018 to Restriction Requirement dated Nov. 22, 2017", 6 pgs.
"U.S. Appl. No. 14/876,167, Response filed Jun. 6, 2018 to Non Final Office Action dated Mar. 13, 2018", 9 pgs.
"U.S. Appl. No. 14/936,831, Non Final Office Action dated May 16, 2018", 11 pgs.
"U.S. Appl. No. 14/936,831, Notice of Non-Compliant Amendment dated Mar. 14, 2018", 2 pgs.
"U.S. Appl. No. 14/936,831, Response filed Mar. 26, 2018 to Notice of Non-Compliant Amendment dated Mar. 14, 2018", 6 pgs.
"U.S. Appl. No. 14/983,108, Non Final Office Action dated Apr. 10, 2018", 7 pgs.
"U.S. Appl. No. 14/983,747, Non Final Office Action dated Apr. 9, 2018", 13 pgs.
"U.S. Appl. No. 14/983,747, Supplemental Response to Restriction Requirement filed Jan. 24, 2018", 5 pgs.
"U.S. Appl. No. 15/131,663, Restriction Requirement dated May 18, 2018", 7 pgs.
"U.S. Appl. No. 15/166,480, Restriction Requirement dated May 21, 2018", 6 pgs.
"U.S. Appl. No. 15/278,777, Response filed May 29, 2018 to Non Final Office action dated Feb. 28, 2018", 11 pgs.
"U.S. Appl. No. 15/659,689, Preliminary Amendment filed Jul. 26, 2017", 7 pgs.
"U.S. Appl. No. 15/945,425, Preliminary Amendment filed Apr. 5, 2018", 8 pgs.
"U.S. Appl. No. 15/945,425, Supplemental Preliminary Amendment filed May 10, 2018", 6 pgs.
"U.S. Appl. No. 15/956,444, Preliminary Amendment filed Apr. 19, 2018", 7 pgs.
"U.S. Appl. No. 15/972,646, Preliminary Amendment filed May 9, 2018", 6 pgs.
"Bio-Intrafix (TCP/PLA) & Intrafix, Tibial Soft Tissue Fasteners", DePuy Mitek, ((date unknown)), 6 pgs.
"Canadian Application Serial No. 2906596, Office Action dated Feb. 26, 2018", 3 pgs.
"European Application Serial No. 16168202.6, Communication Pursuant to Article 94(3) EPC dated Apr. 25, 2018", 5 pgs.
"European Application Serial No. 17169003.5, Extended European Search Report dated May 11, 2018", 8 pgs.
"International Application Serial No. PCT/US2012/037703, Invitation to Pay Additional Fees dated Jul. 19, 2012".
"International Application Serial No. PCT/US2013/058921, International Preliminary Report on Patentability dated Mar. 26, 2015", 9 pgs.
"International Application Serial No. PCT/US2013/058921, International Search Report dated Oct. 21, 2013", 5 pgs.
"International Application Serial No. PCT/US2013/058921, Written Opinion dated Oct. 21, 2013", 6 pgs.

\* cited by examiner

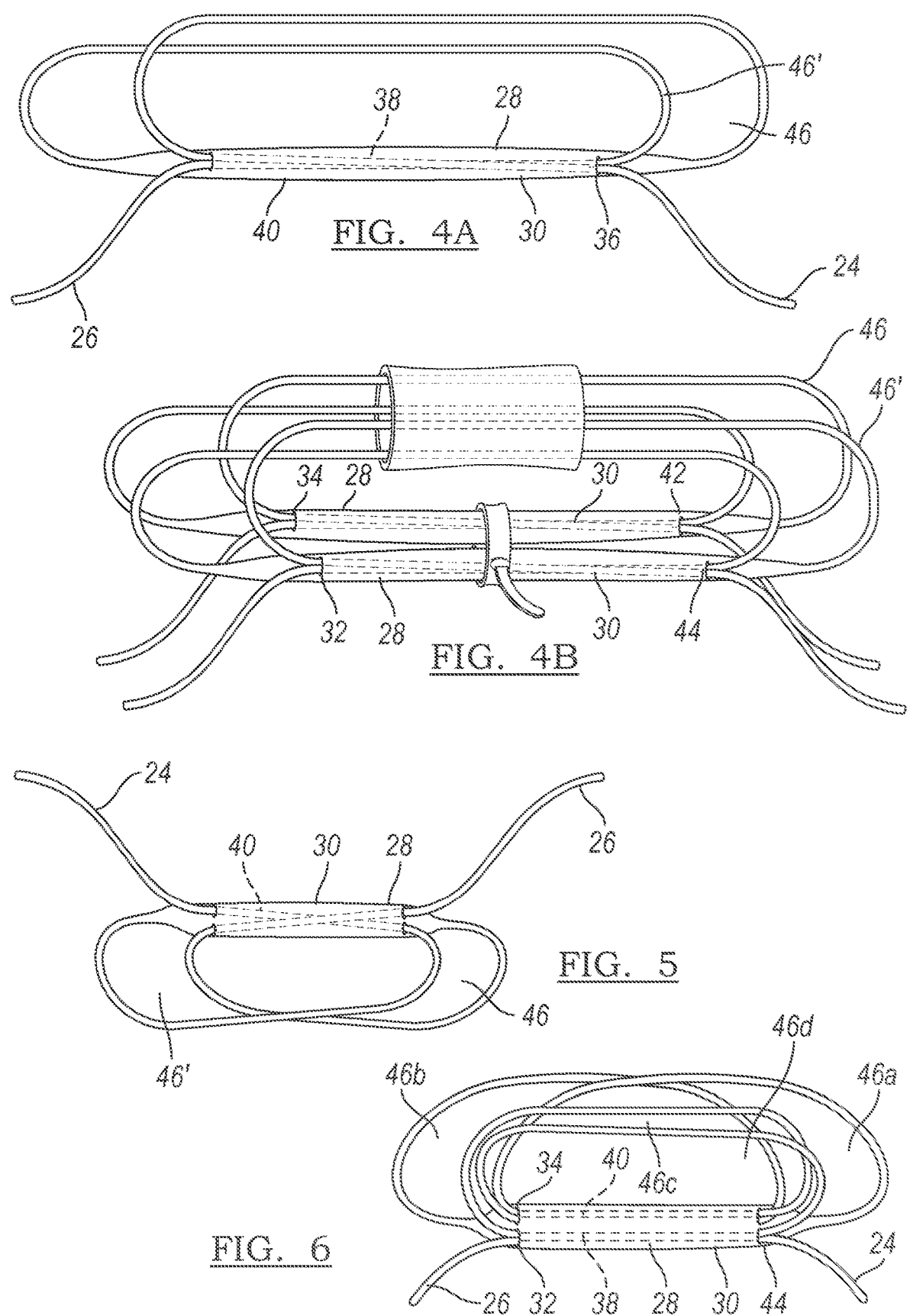

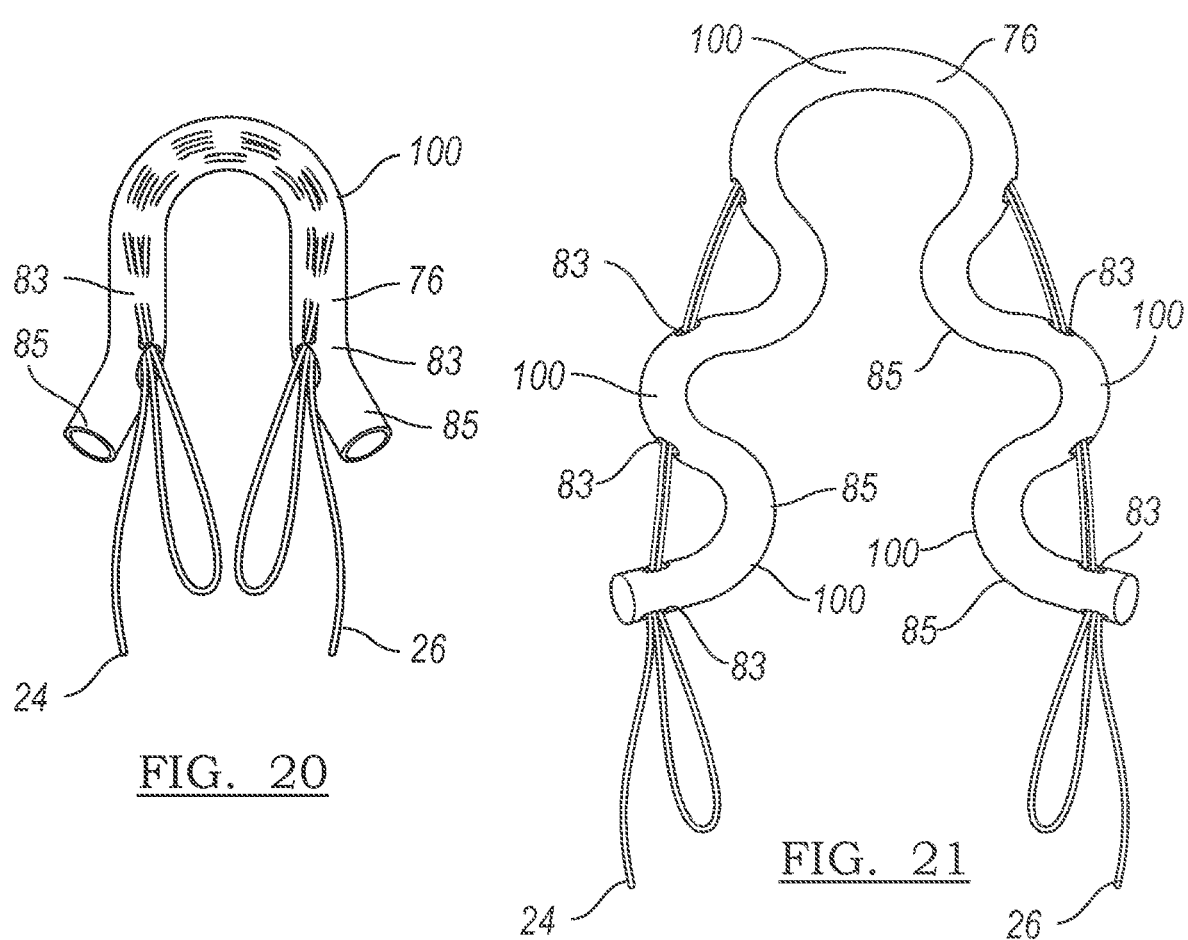
FIG. 20
FIG. 21
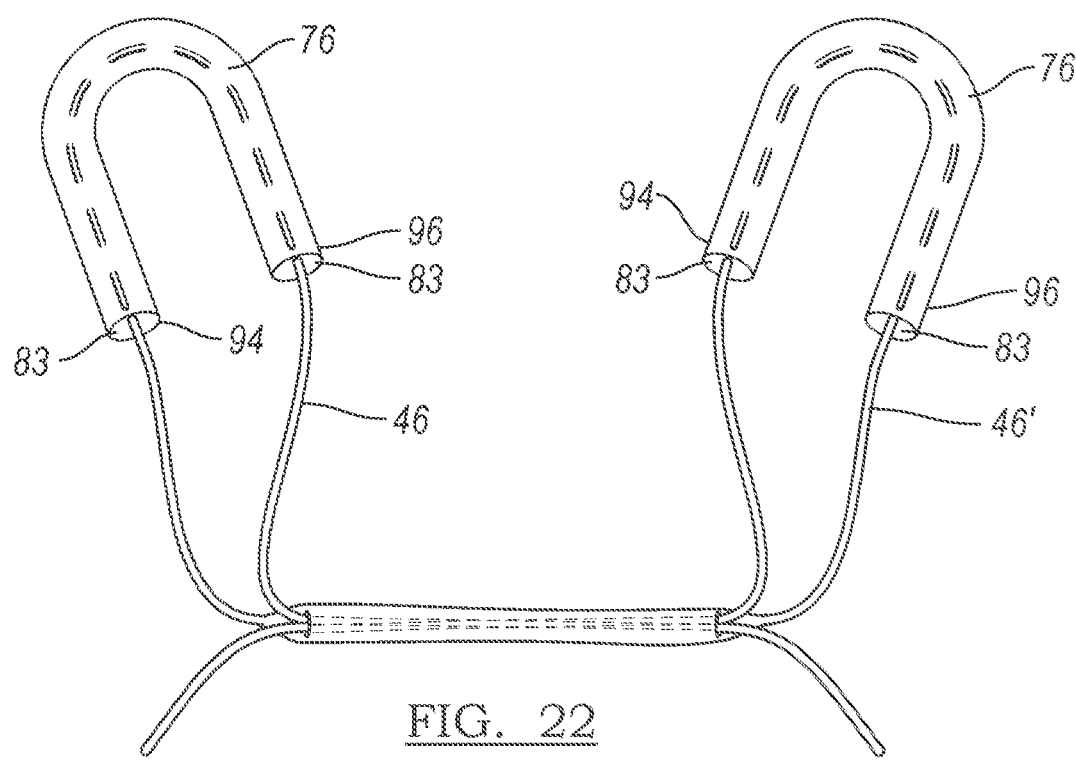
FIG. 22

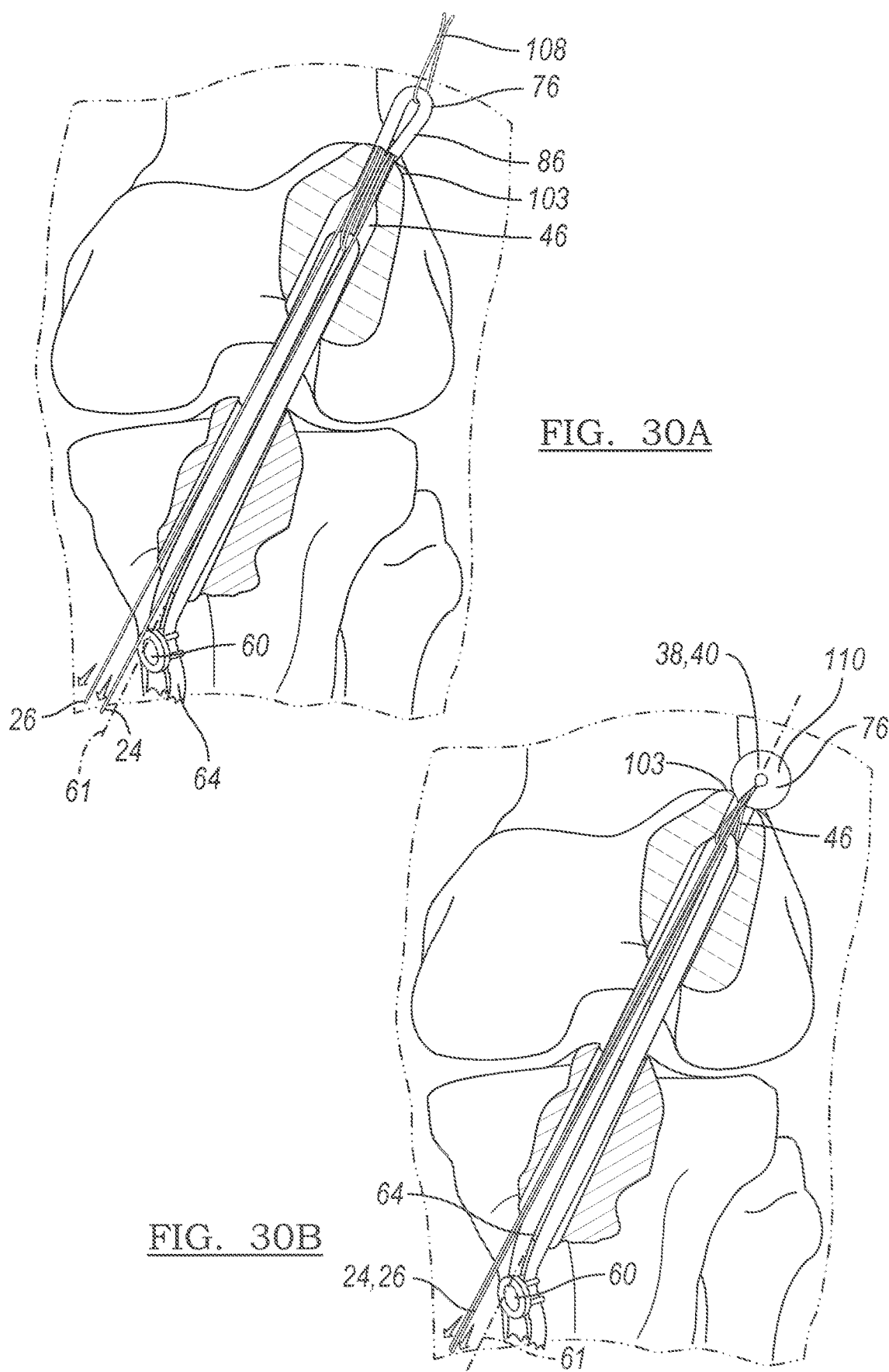

METHOD AND APPARATUS FOR COUPLING SOFT TISSUE TO A BONE

CROSS-REFERENCE TO RELATED APPLICATIONS

This application is a continuation of U.S. patent application Ser. No. 14/983,747 filed Dec. 30, 2015, which is a continuation of U.S. patent application Ser. No. 13/751,846 filed Jan. 28, 2013, now U.S. Pat. No. 9,492,158 issued on Nov. 15, 2016, which is a divisional of U.S. patent application Ser. No. 12/489,168 filed Jun. 22, 2009, now U.S. Pat. No. 8,361,113 issued on Jan. 29, 2013, which is a continuation-in-part application of: (1.) U.S. patent application Ser. No. 12/474,802 filed on May 29, 2009, now U.S. Pat. No. 8,088,130 issued on Jan. 3, 2012; (2.) U.S. patent application Ser. No. 11/541,506 filed on Sep. 29, 2006, now U.S. Pat. No. 7,601,165 issued on Oct. 13, 2009; (3.) U.S. patent application Ser. No. 11/541,505 filed on Sep. 29, 2006, now U.S. Pat. No. 7,658,751 issued on Feb. 9, 2010; (4.) U.S. patent application Ser. No. 12/014,399 filed on Jan. 15, 2008, now U.S. Pat. No. 7,909,851 issued on Mar. 22, 2011; (5.) U.S. patent application Ser. No. 12/014,340 filed on Jan. 15, 2008, now U.S. Pat. No. 7,905,904 issued on Mar. 15, 2011; (6.) U.S. patent application Ser. No. 11/935,681 filed on Nov. 6, 2007, now U.S. Pat. No. 7,905,903 issued on Mar. 15, 2011; (7.) U.S. patent application Ser. No. 11/869,440 filed on Oct. 9, 2007, now U.S. Pat. No. 7,857,830 issued on Dec. 28, 2010; (8.) U.S. patent application Ser. No. 11/784,821 filed on Apr. 10, 2007; (9.) U.S. patent application Ser. No. 11/347,661 filed on Feb. 3, 2006, now U.S. Pat. No. 7,749,250 issued on Jul. 6, 2010; (10.) U.S. patent application Ser. No. 11/347,662 filed on Feb. 3, 2006, now abandoned; (11.) U.S. patent application Ser. No. 12/196,405 filed on Aug. 22, 2008, now U.S. Pat. No. 8,128,658 issued on Mar. 6, 2012; (12.) U.S. patent application Ser. No. 12/196,407, filed on Aug. 22, 2008, now U.S. Pat. No. 8,137,382 issued on Mar. 20, 2012; and (13.) U.S. patent application Ser. No. 12/196,410, filed on Aug. 22, 2008, now U.S. Pat. No. 8,118,836 issued on Feb. 21, 2012.

The disclosures of the above applications are incorporated herein by reference.

FIELD

The present disclosure relates to method of coupling soft tissue to a bone and, more particularly, to a method of implanting an ACL within a femoral tunnel.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for configuring a braided tubular suture and a suture configuration are disclosed. The method includes passing a first n of the suture through a first aperture into a passage defined by the suture and out a second aperture defined by the suture so as to place the first end outside of the passage, A second end of the suture is passed through the second aperture into the passage and out the first aperture so as to place the second end outside of the passage.

A method of surgically implanting a suture construction in a femoral tunnel is disclosed. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. The first and second ends and the first and second loops are then passed through the femoral tunnel. Soft tissue is then passed through the first and second loops. Tension is applied onto the first and second ends to constrict the first and second loops to pull the soft tissue into the tunnel.

In another embodiment, a method of surgically implanting a suture is disclosed. The suture is passed through a bore defined by a first fastener. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A second fastener is coupled to at least one of the first and second loops. After the fastener is coupled to the patient, tension is applied onto the first and second ends to constrict at least one of the first and second loops.

In another embodiment a method of surgically implanting a soft tissue replacement for attaching two bone members is disclosed. A first and second tunnel is formed in first and second bones. A locking member having a first profile which allows insertion of the locking member through the tunnel and a second profile which allows engagement with the positive locking surface upon rotation of the locking member is provided. The suture construction described above is coupled to the locking member. The first and second ends and the first and second loops of the construction and the locking member are threaded through the first and second tunnels. Soft tissue is threaded through the first and second loops so as to engage bearing surfaces on the first and second loops. The locking member is then engaged.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes on and are not intended to limit the scope of the present disclosure in any way.

FIGS. 4A and 4B represent alternate suture configurations;

FIGS. 5-7 represent further alternate suture configurations;

FIGS. 17-21 represent adjustable length textile anchors according to the teachings herein;

FIGS. 22-24 represent alternate adjustable length textile anchors;

FIGS. 30A and 30B represent the coupling of an ACL replacement in a femoral/tibial reconstruction using the textile anchor of FIG. 17;

DETAILED DESCRIPTION

Figure 1:
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
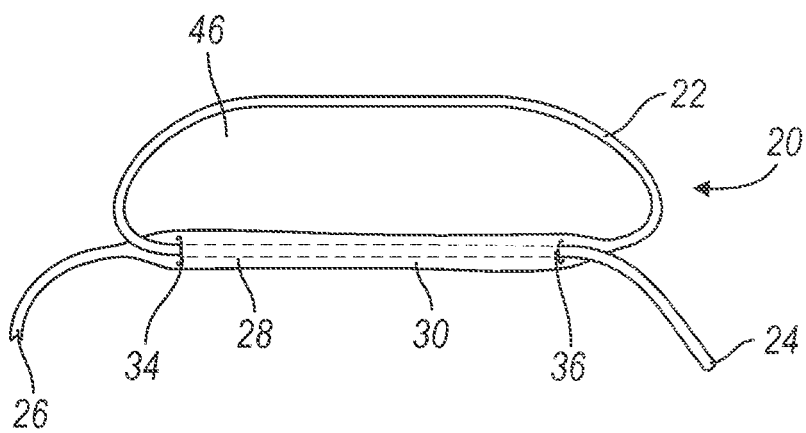
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
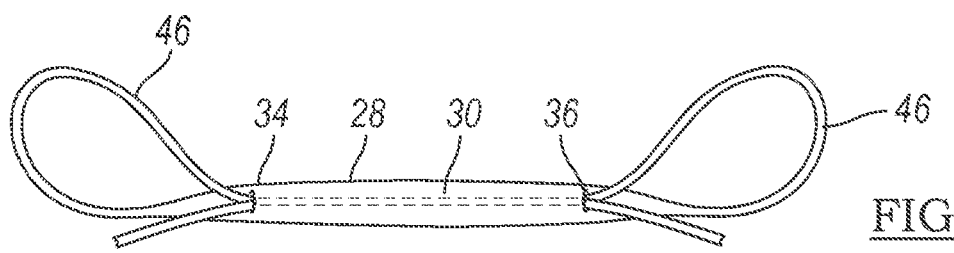
Figure 3:
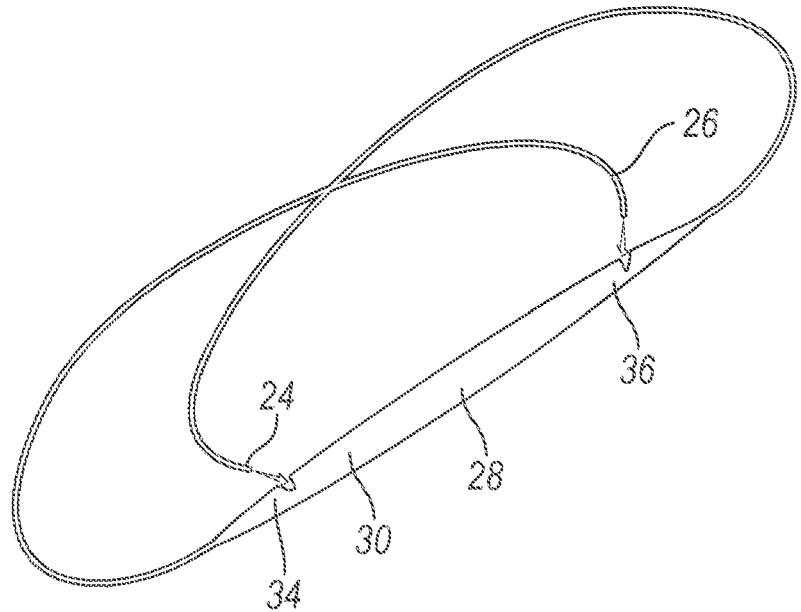
FIG. 3 represents the formation of the suture configuration shown in FIG. 4A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 7:
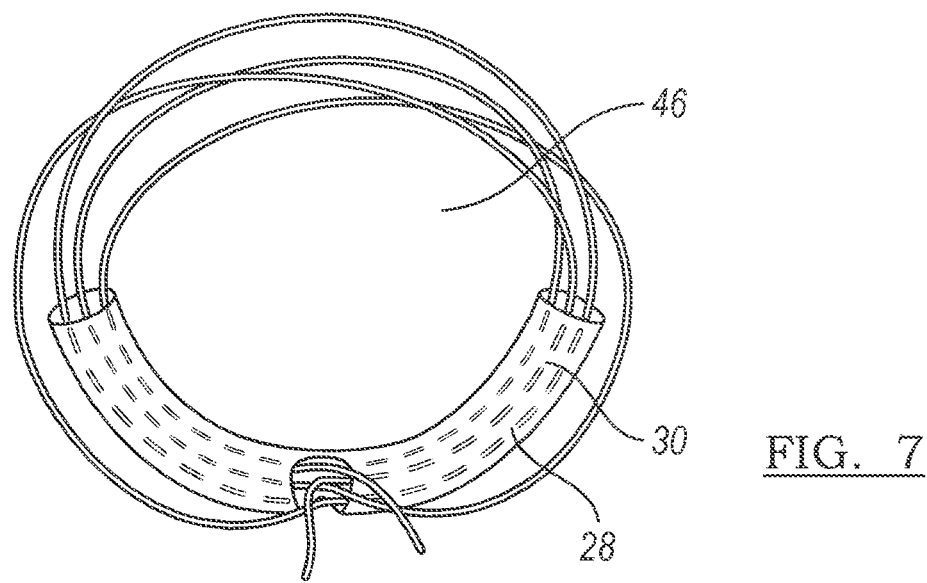
Figure 8:
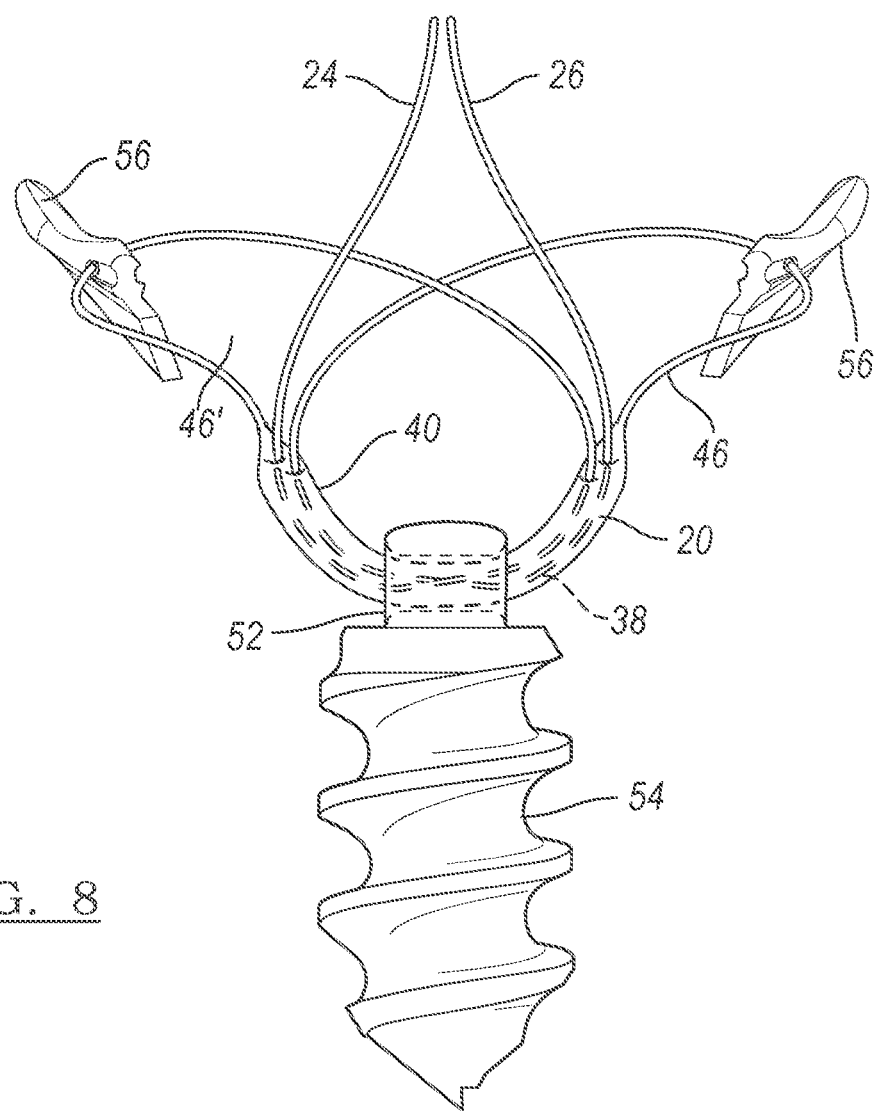
FIG. 8 represents the suture construction according to FIG. 5 coupled to a bone engaging fastener.
Figure 9:
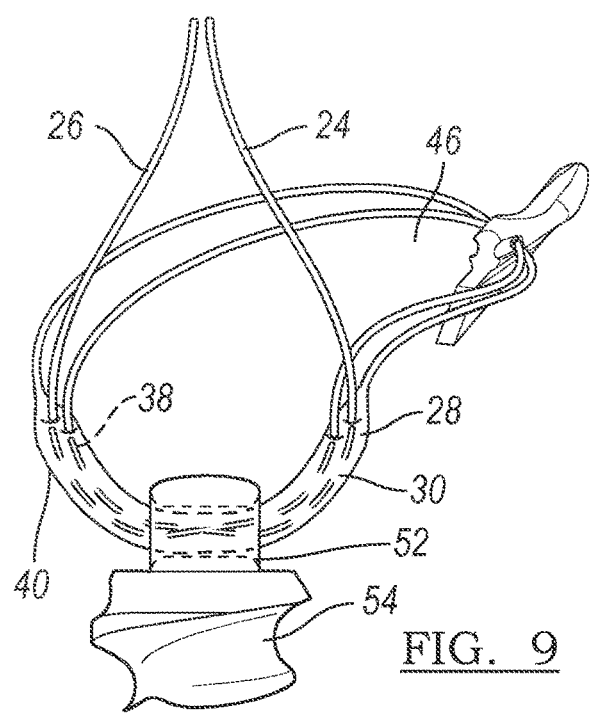
FIGS. 9-11B represent the coupling of the suture construction according to FIG. 5 to a bone screw.
Figure 10:
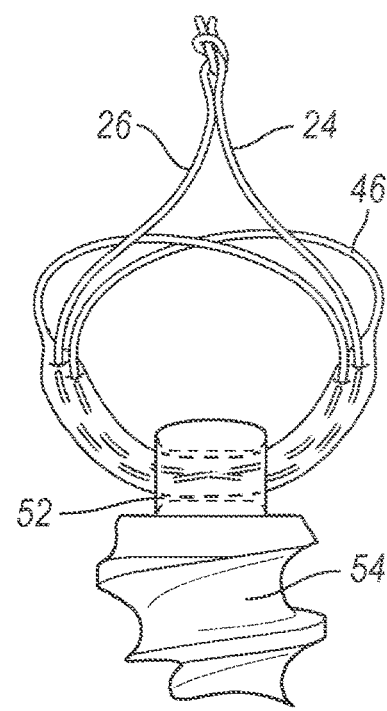

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46a-d is reduced to a desired size or load. At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
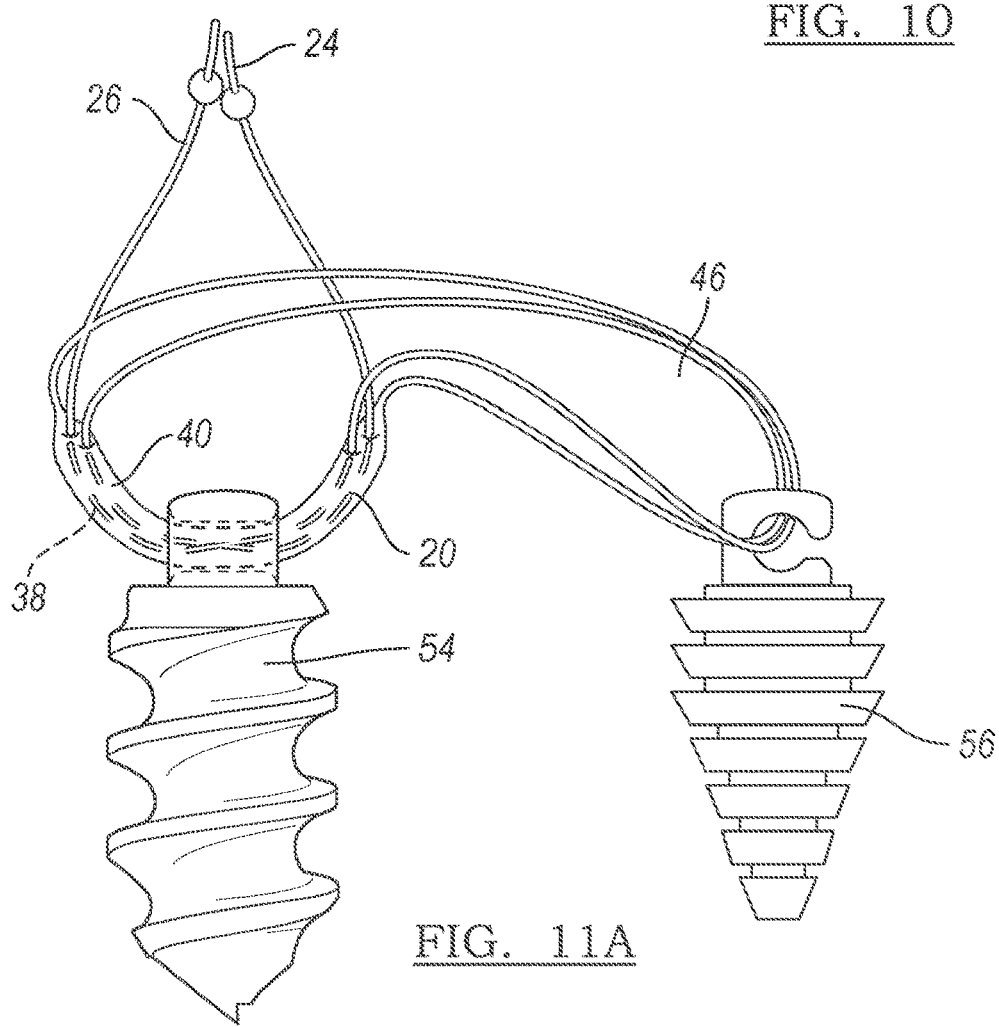
Figure 11B:
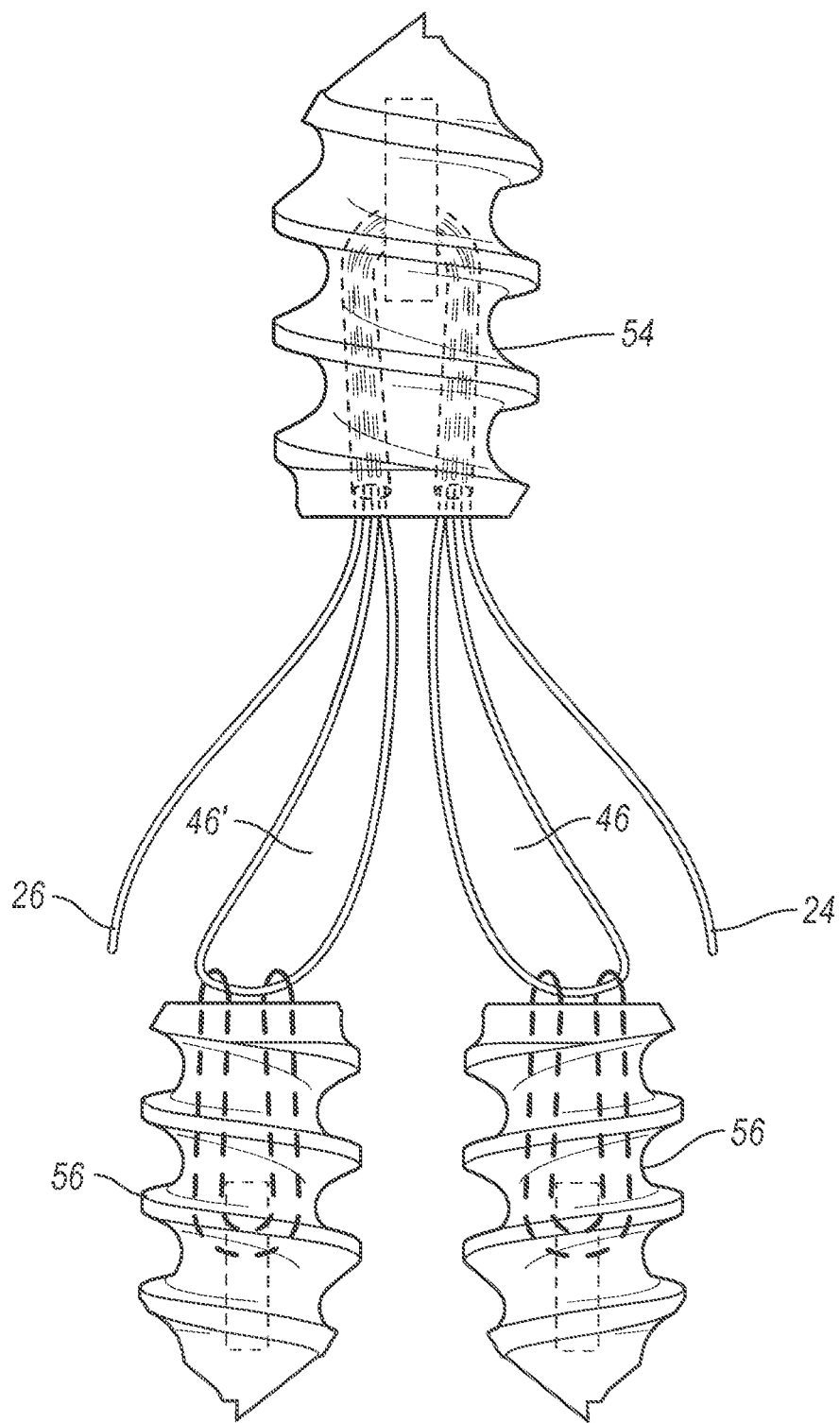

FIG. 11B represents the coupling of the suture construction according to FIG. 2B with a bone fastening member. Coupled to a pair of loops 46 and 46' is tissue fastening members 56. The application of tension to either the first or second end 24 or 26 will tighten the loops 46 or 46' separately.

Figure 12A:
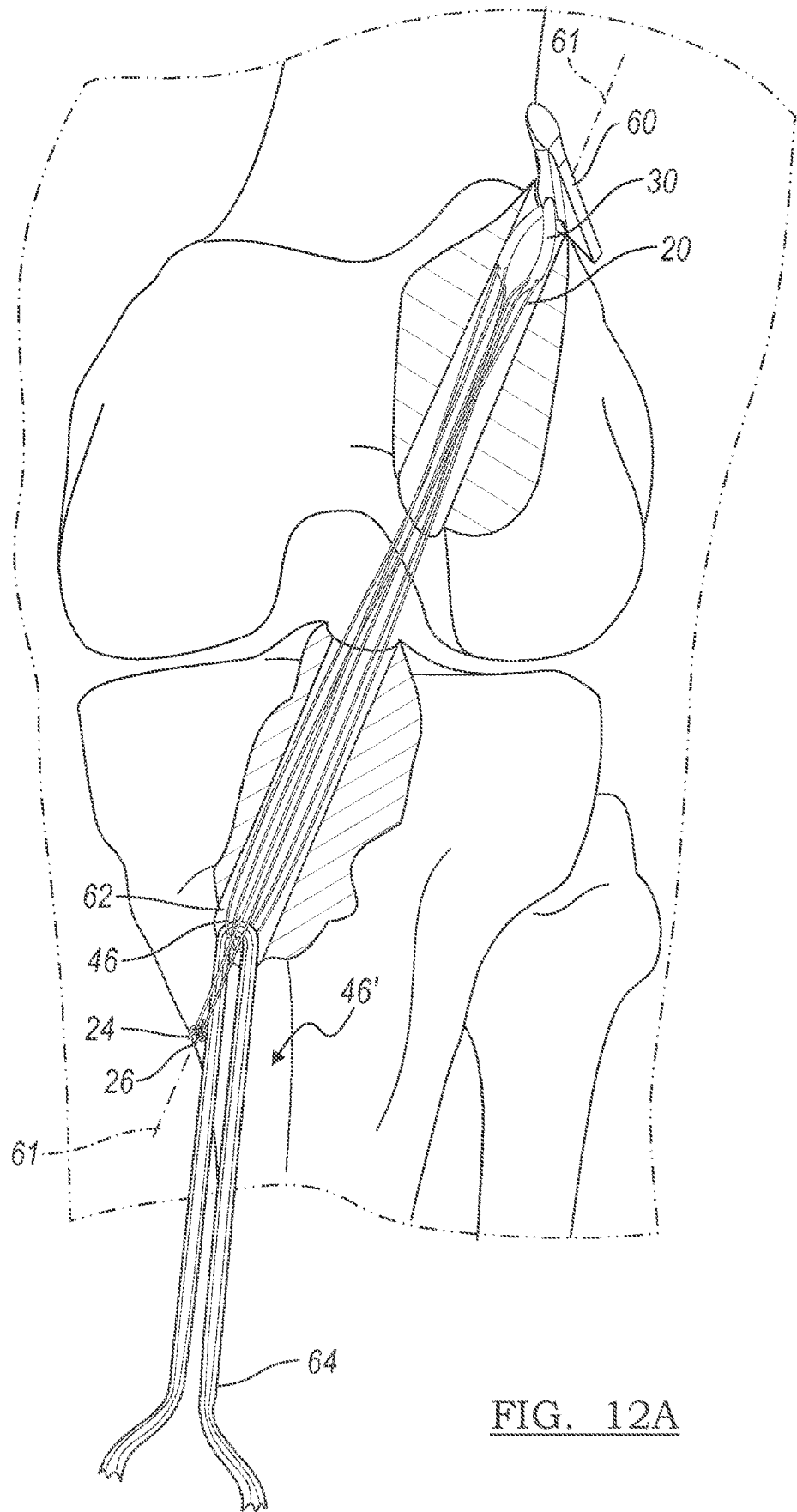
FIGS. 12A-12E represent the coupling of a soft tissue to an ACL replacement in a femoral/humeral reconstruction.
Figure 12B:
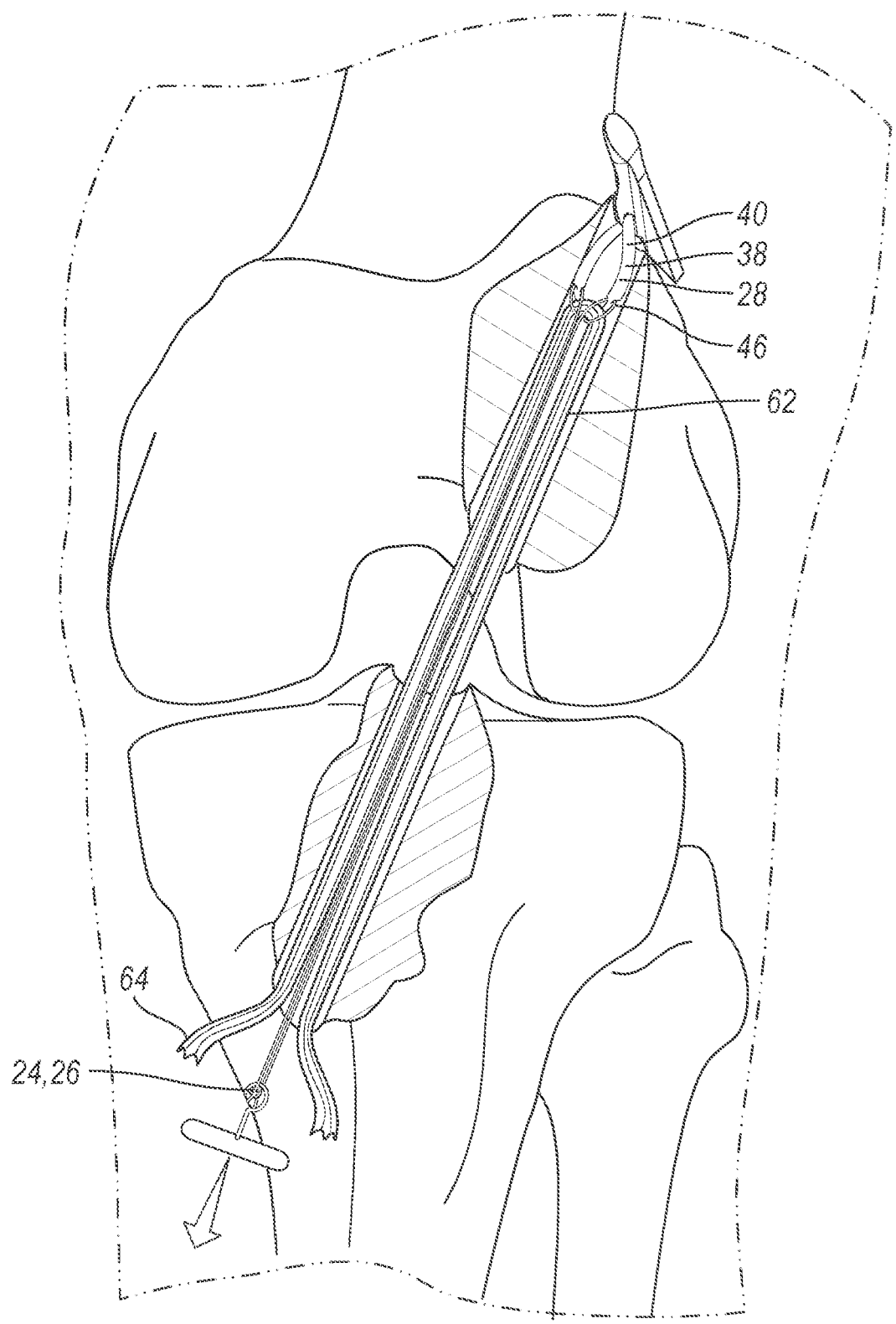
Figure 12C:
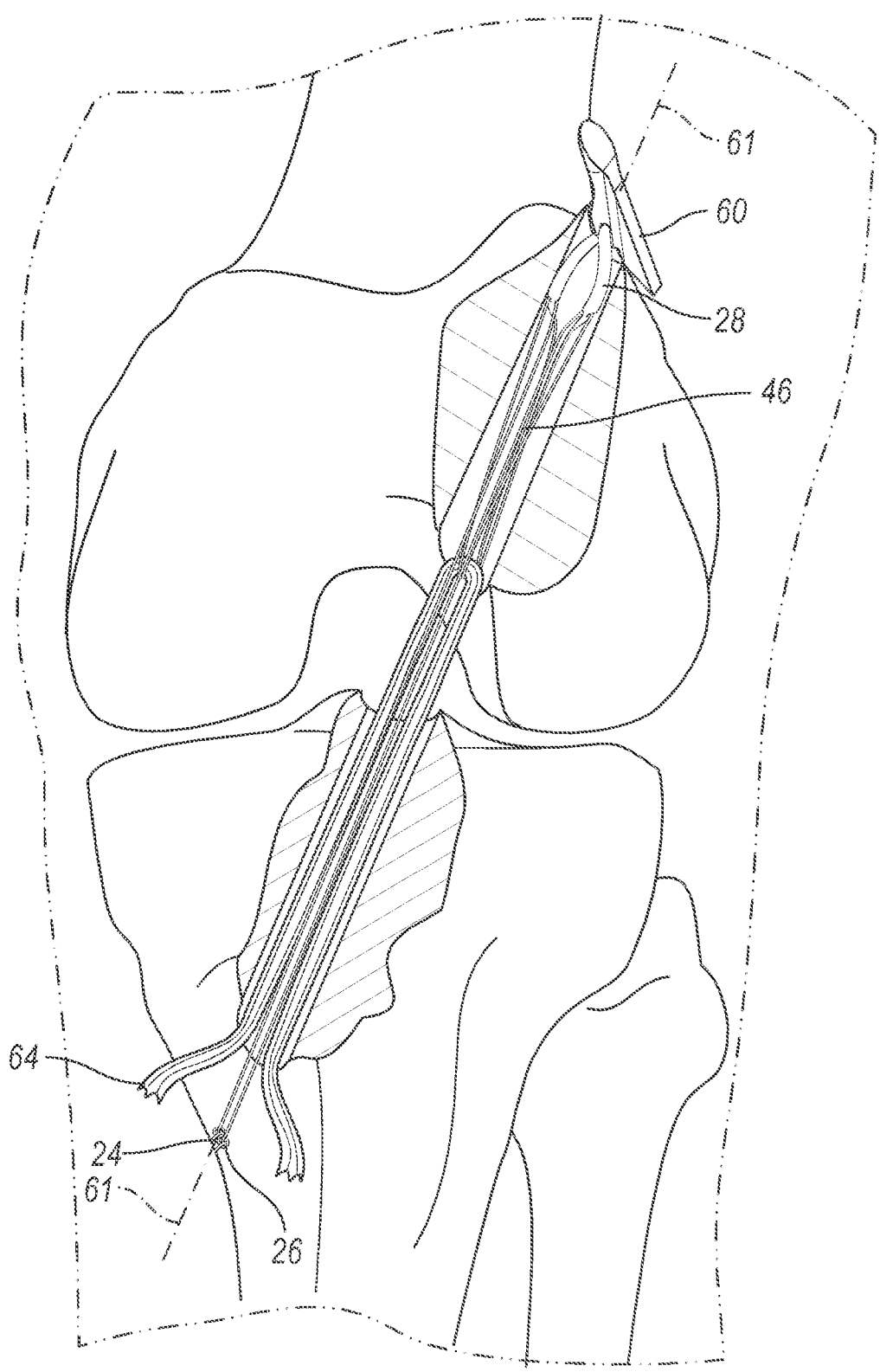
Figure 12D:
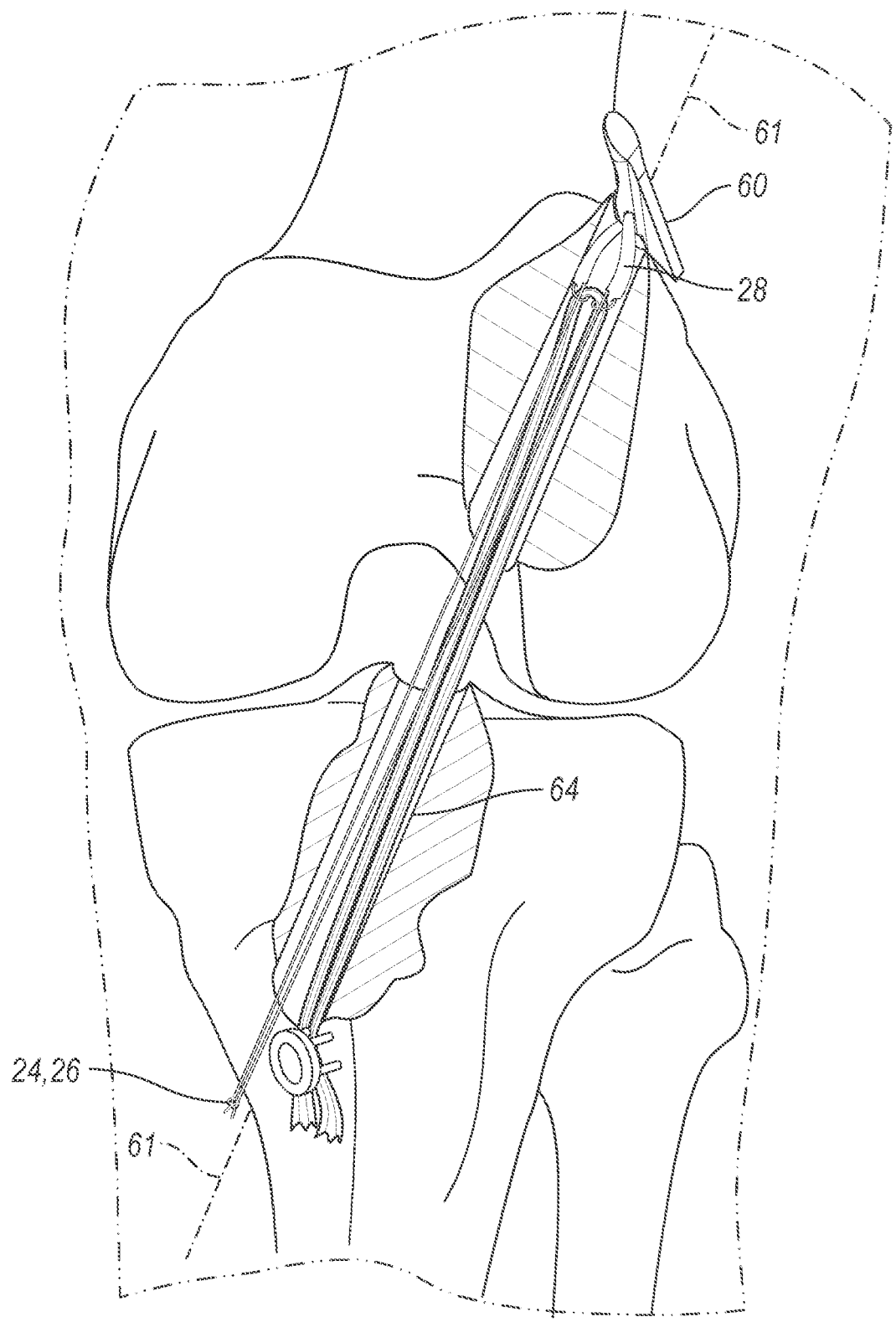

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member 60. The member 60 can have a first profile which allows insertion of the member 60 through the tunnel and a second profile which allows engagement with a positive locking surface upon rotation. The longitudinal passage portion 30 of the suture construction 20, member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the Orientation of the longitudinal passage portion 30, the loops 46, and ends 24, 26 allow for tension to be applied to the construction 20 without applying non-seating forces to the fixation member 60. As an example, should the loops 24, 26 be positioned at the member 60, application of forces to the ends 24, 26 may reduce the seating force applied by the member 60 onto the bone.

As best seen in FIG. 120, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known. The suture construction has loops 46 and 46' with a first length which allows rotation of the fixation member 60. Application of tension onto the ends 24, 26 of the sutures pulls the fixation member 60 into position and the loops 46 and 46' into a second length. In this position, rotation of the locking member in inhibited.

Figure 12E:
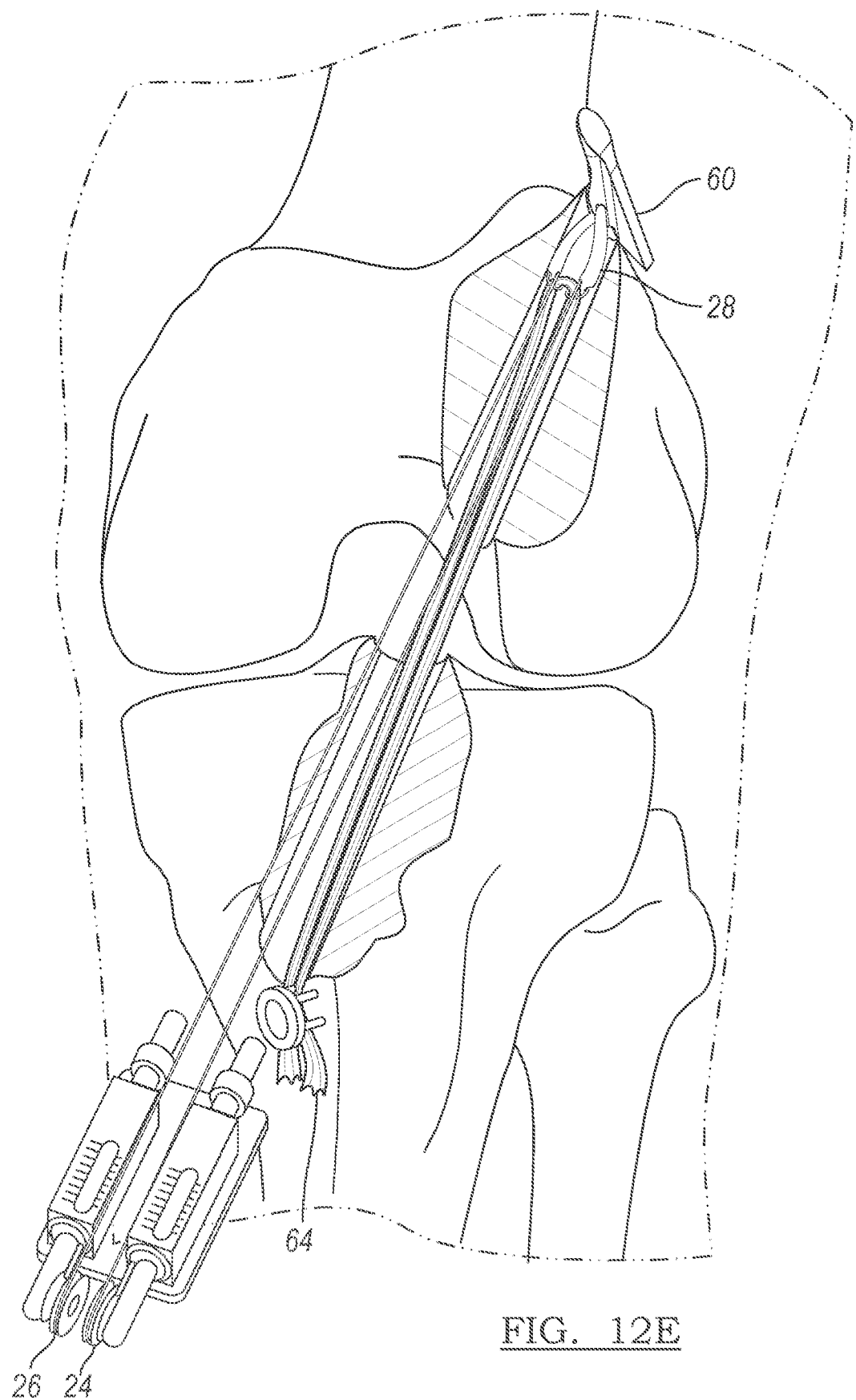
Figure 13A:
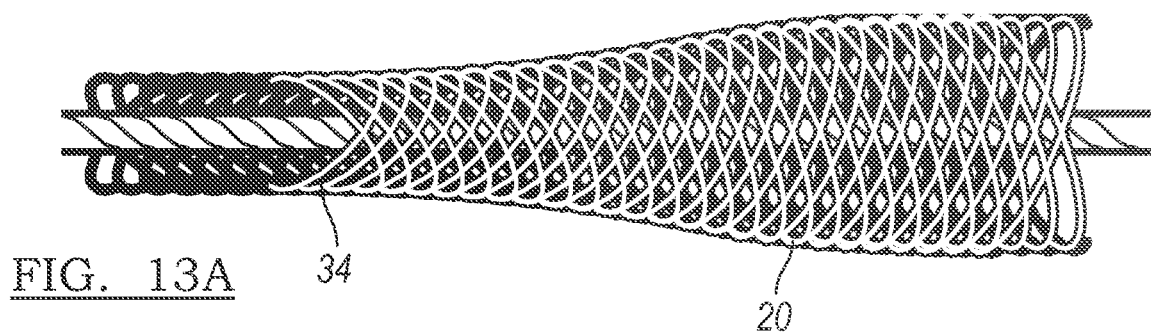
FIGS. 13A-13D represent a close-up view of the suture shown in FIGS. 1-11C.
Figure 13B:
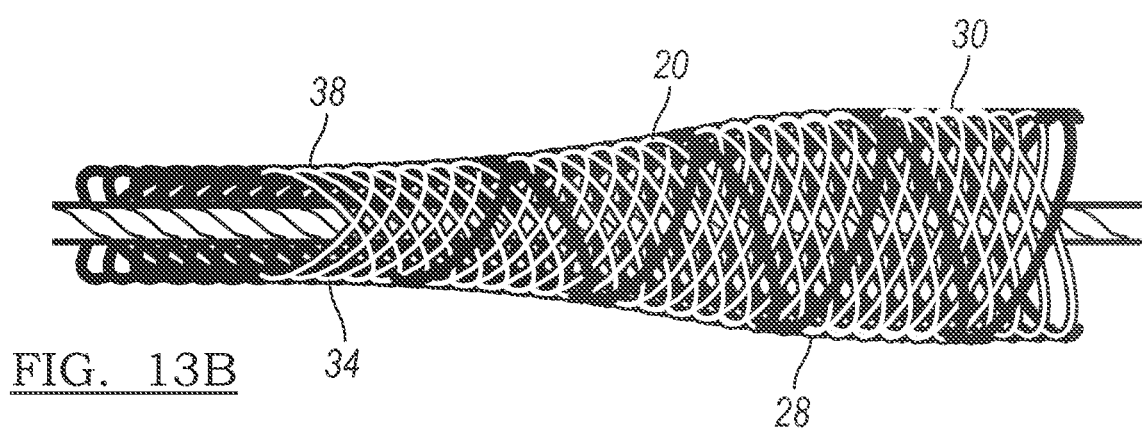
Figure 13C:
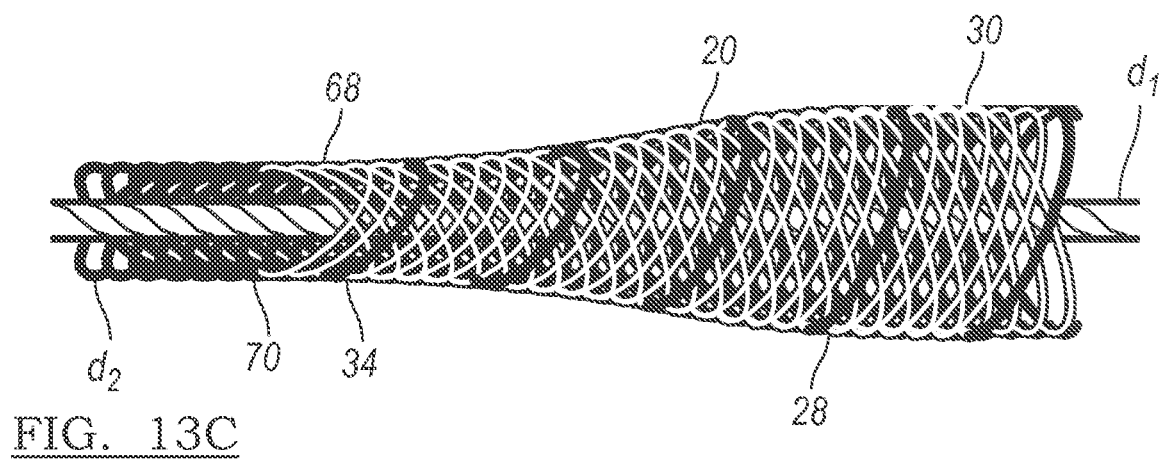
Figure 13D:
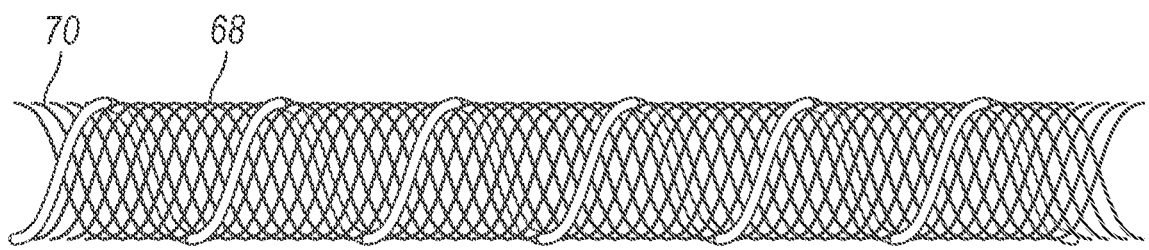

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

Figure 14:
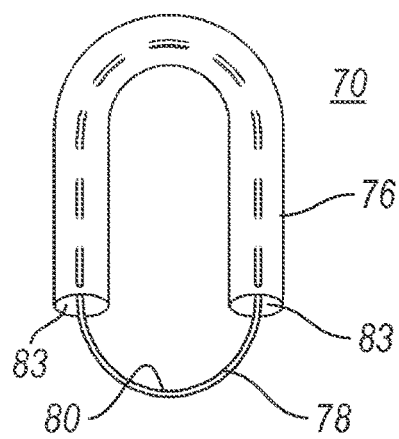
FIGS. 14-16 represent fixed length textile anchors.
Figure 15:
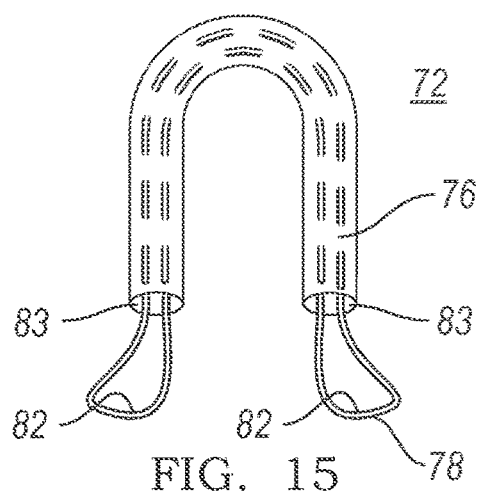
Figure 16:
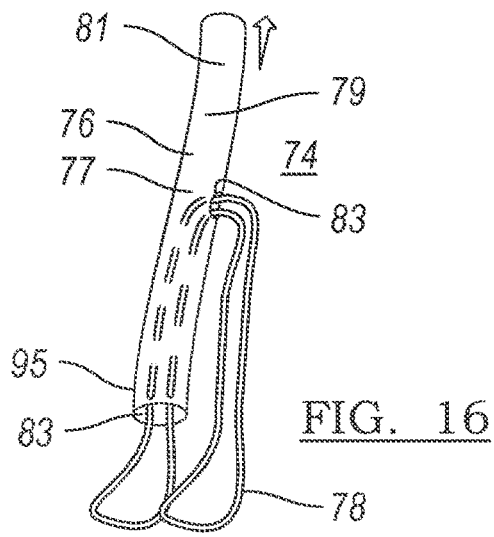

FIGS. 14-16 represent collapsible anchors 70, 72, 74 according to the present teachings. The anchors are deformable from a first cross section to a second engaging cross section. The anchors 70, 72, 74 are biocompatible materials for example polymer or a knit or woven textile such as braided nylon material. Disposed within a collapsible tube 76 is a closed loop of suture material 78 which may form a portion of the collapsible tube 76. Optionally, this collapsible tube 76 can be slidable with respect to the closed loop of suture material 78. The collapsible tube 76 is further collapsible to form a fabric mass 110 (see for example FIG. 29B).

The suture material 78 can be passed through a pair of openings 83 in the collapsible tube 76 a single time to form a single soft tissue bearing surface 80. Additionally, (see FIG. 15), the closed loop of the suture material 78 can be looped over itself and passed through the collapsible flexible tube 76 to form a pair of soft tissue bearing surface portions 82. In each of the embodiments shown, the collapsible tube 76 defines at least one tube bearing surface.

FIG. 16 represents a closed loop of suture 78 passed through an aperture 77 defined in a body 79 of the collapsible tube 76. In this regard, the suture 78 is passed through a first open end 95 of the tube 78 and through the aperture 77 leaving a portion 81 of the collapsible tube 76 which can be used to assist in the insertion of a graft to a patient (see FIG. 32A).

Figure 17:
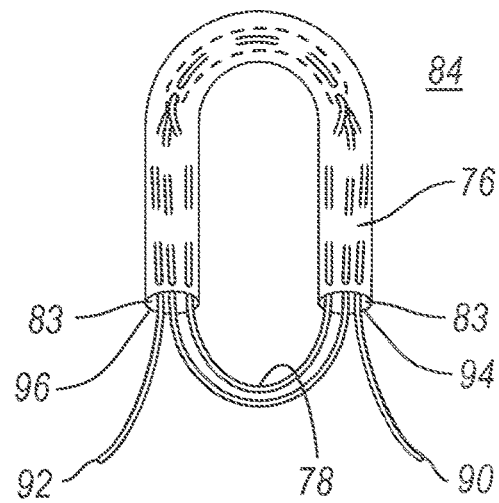
Figure 18:
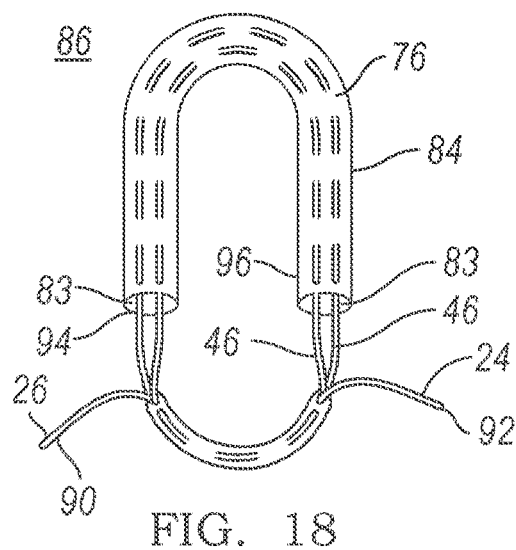
Figure 19:
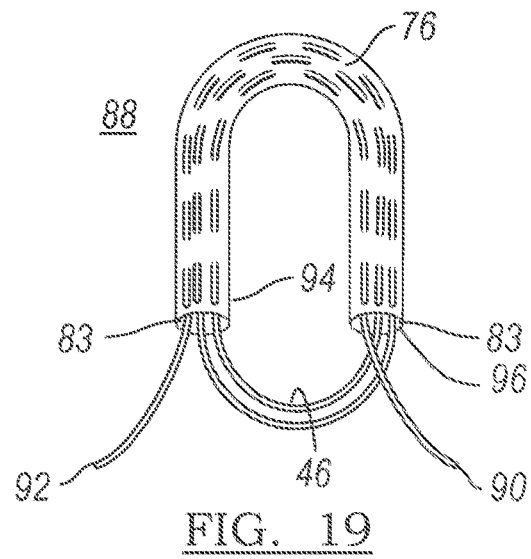

FIGS. 17-19 represent adjustable sized loops of suture material 78 disposed within the collapsible tube 76 so as to form a suture anchor assembly 84, 86, 88. FIG. 17 shows the suture material 78 passed several times through the collapsible tube 76. By applying tension to the ends 90 and 92 of the suture material 78, the loops of the suture material constrict. If placed adjacent to a bearing surface (not shown), the end 94 and 96 of the collapsible tube 76 are brought together, thus collapsing the tube to form a collapsed material or fabric mass 110. It is envisioned a portion of the suture material 78 can be passed through the collapsible tube 76 to help maintain the position of the suture with respect to the collapsible tube 76.

FIGS. 18 and 19 show the loops of the suture construction of FIG. 4a within a collapsible tube 76. The tubular portion of the construction of FIG. 4a can be disposed either within or outside of the collapsible tube 76. As with the embodiment shown in FIGS. 14-16, translation of the tube 76 with respect to the suture material 78 can cause the ends 94 of the tube 76 to be brought together to compress the loops into a fabric mass 110.

FIGS. 20 and 21 show the loops of FIG. 2B, 4A or 5 disposed within the collapsible tube 76. Shown are the ends and loops disposed at least partially through a portion 100 of the tube 76. Tensioning of the ends 24, 26 causes the portions 100 of the tube 76 to collapse to form a mass 110, while leaving other portions 85 uncollapsed. The outer uncollapsed portion 85 can function as a bearing surface to assist in the collapse of portion 100 when portion 100 is subjected to compressive loads.

FIG. 21 shows an embodiment where suture loops are passed through the sidewalls of the collapsible tube 76. Optionally, the loops 46 and 47 as well as the ends 24 and 26 can be passed through together. This construction can be used in situations where a large collapsed mass 110 is needed FIG. 22 shows the loop of FIG. 2B having a pair of collapsible tubes 76. The collapsible tubes 76 are disposed about the loops 46 and 46' and will collapse upon application of tension to the ends of the suture construction in a manner which places compressive loads onto the ends of the tube 76. It is envisioned that these collapsible tubes 76 can be collapsed simultaneously or staggered in time as needed by a treating physician. It is also envisioned that the loop construction can be used to pull adjacent portions of a patient's anatomy together.

Figure 23:
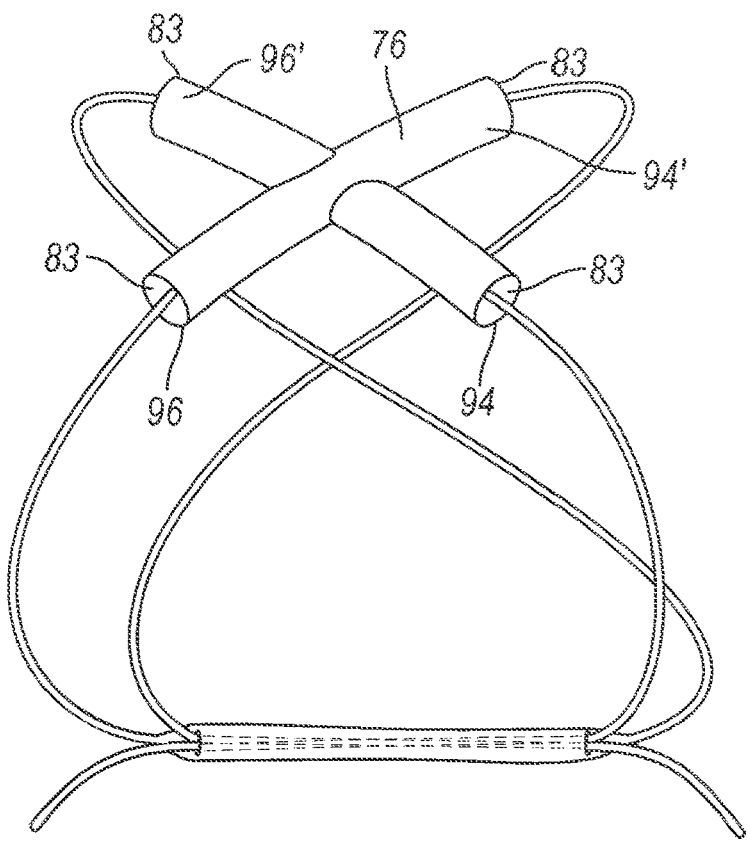

FIG. 23 depicts the loop construction shown in FIG. 2A having its loops disposed through a pair of co-joined crossed collapsible tubes 76. If placed adjacent to a bearing surface, the ends of the co-joined tubes come together, thus increasing in cross-section. This forms the fabric mass 110. This construction can be used in situations where a large collapsed mass is needed.

Figure 24:
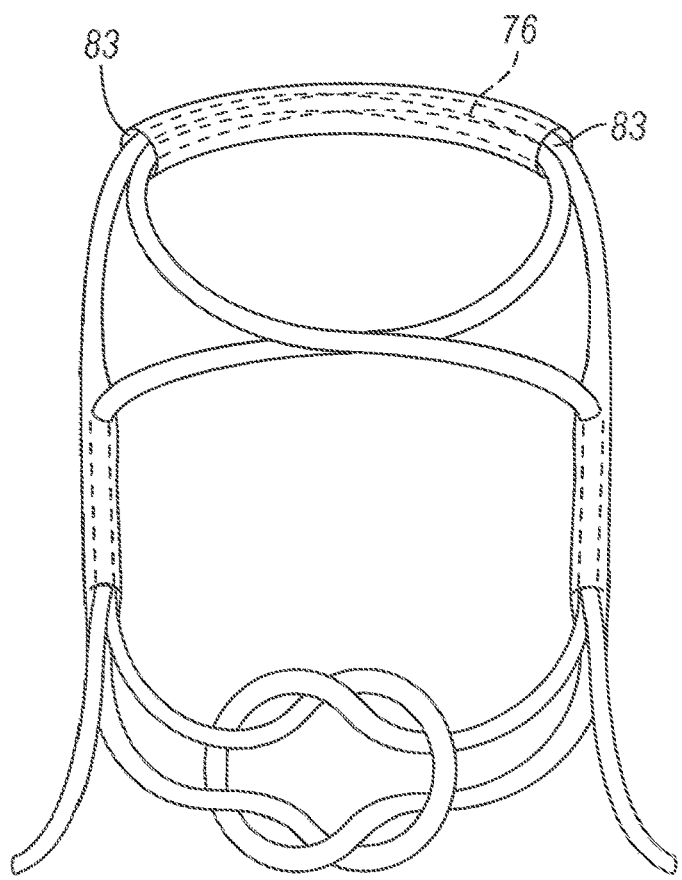

FIG. 24 shows the complex suture construction which embodies a pair of suture constructions of FIG. 2A coupled together using a collapsible tube 76. The ends of the suture 22 can be passed though a pair of passages 30 and 30' formed in the suture material 22. Portions of the suture 22 are looped through each other to form a pair of locked loops 112. This construction can be used to provide a static seat for a graft bearing surface.

Figure 25:
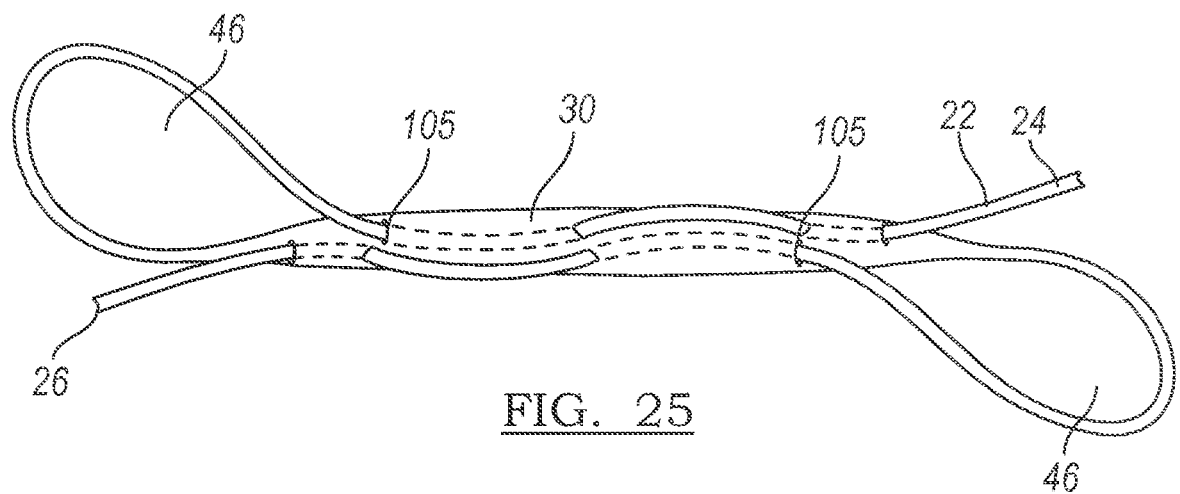
FIGS. 25-27 represent alternate suture configurations.
Figure 26:
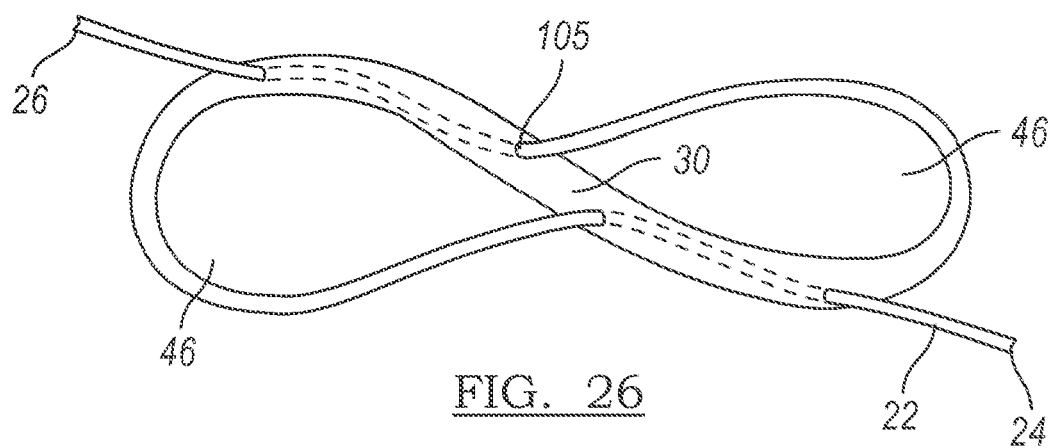
Figure 27:
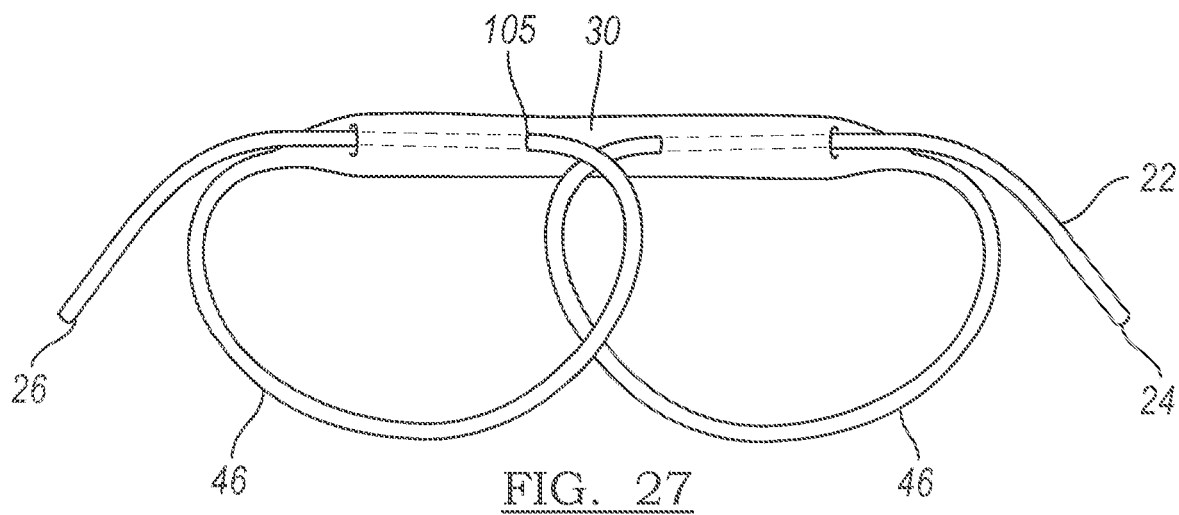

FIGS. 25-27 represent alternate suture constructions where the ends of the sutures 22 are fed multiple times through holes 105 defined within longitudinal passage 30 of the suture to form adjustable loops 46. In situations where relaxation of a tightened construction is to be minimized, the ends can be passed in and out of the passage 30 several times. In this regard, the first and second ends are positioned so as to be parallel and adjacent to each other in the passage 30.

FIGS. 26 and 27 represent constructions where the first and second ends 24 and 26 a passed through the same passage 30, but do not overlap and are not adjacent. This construction may be useful for joining pairs of members. This construction would be useful to bind pairs of appendages such as fingers.

Figure 28:
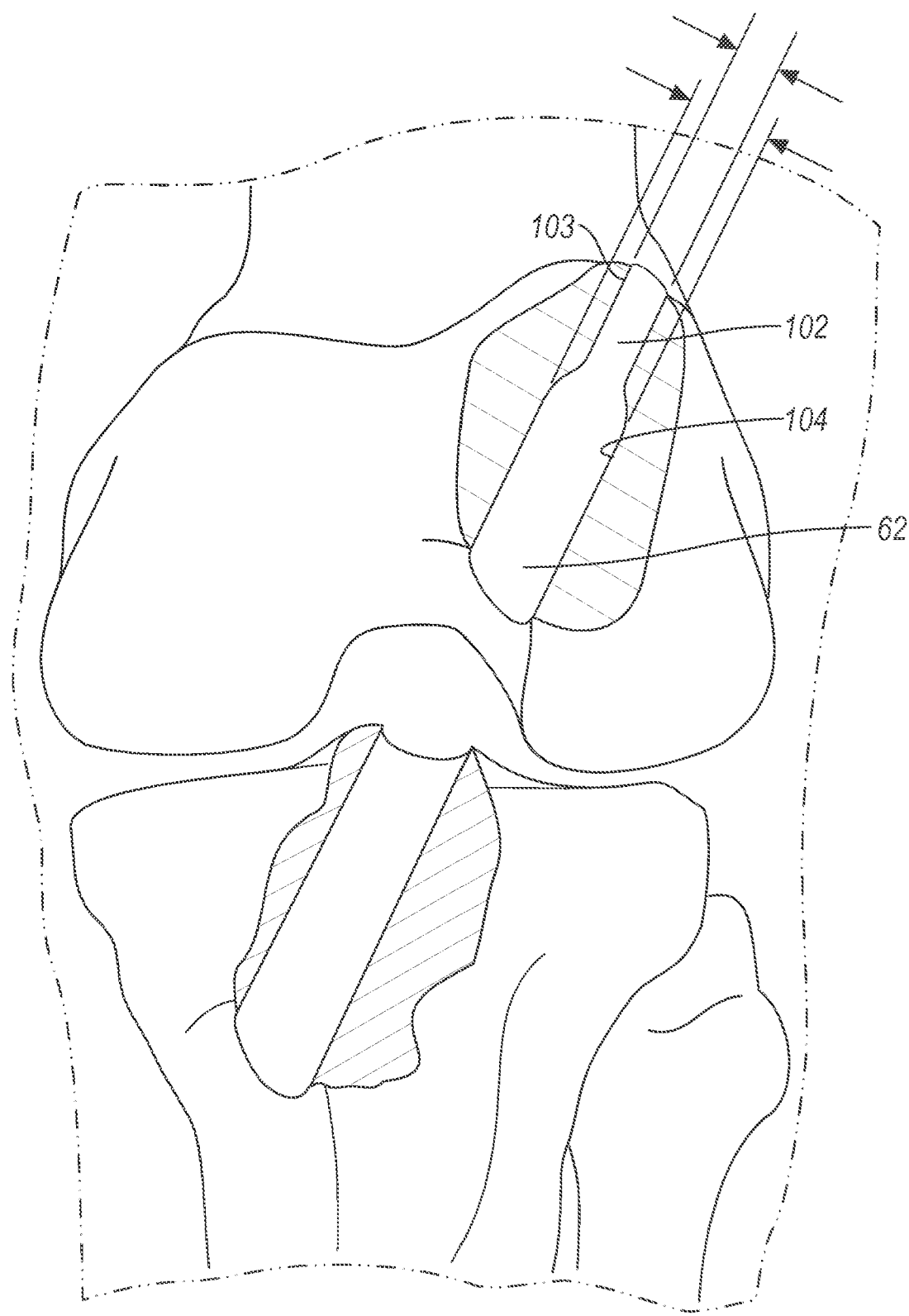
FIG. 28 represents the preparation of the tibia and femur to accept the anchors disclosed in FIGS. 14-24.

FIG. 28 represents the formation of a femoral tunnel shown as a tunnel 62 having a varying diameter. Disposed within either the femoral or tibial tunnel 62 are a first portion 102 having a first diameter and a second portion 104 having a second diameter larger than the first diameter. Defined on an exterior surface of either the tibia or femur is a bearing surface 103, which is configured to interface with the fabric mass 110 of compressed textile material to prevent the relative motion of the fabric mass 110, and thus the suture construction with respect to the bone. This bearing surface can be machined or natural.

Figure 29A:
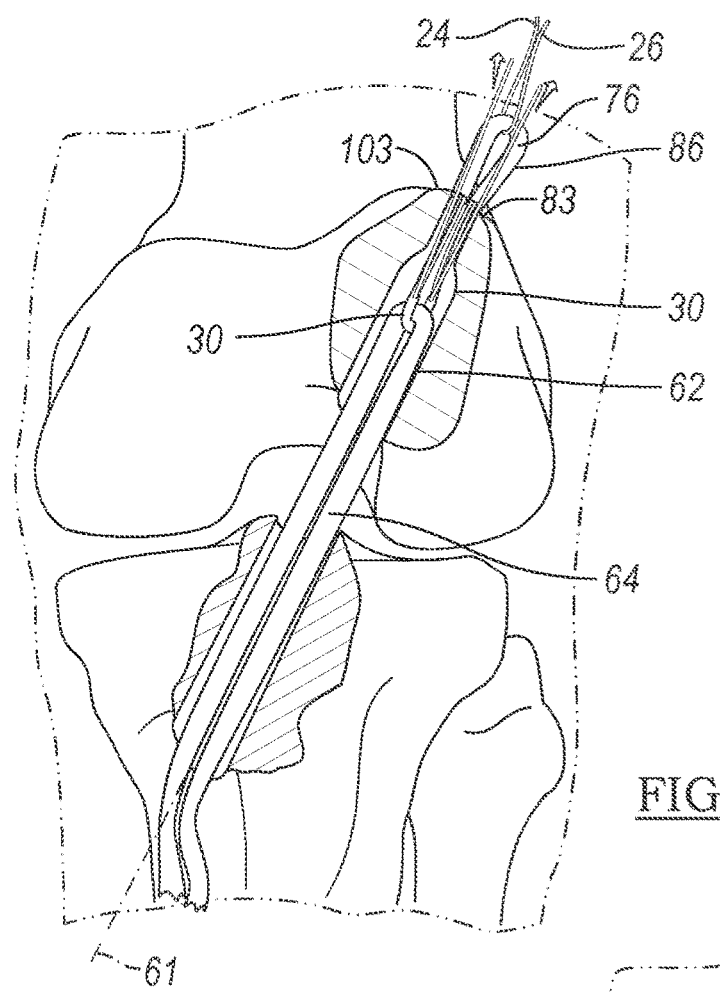
FIGS. 29A and 29B represent the coupling of an ACL replacement in a femoral/tibial reconstruction using the textile anchor of FIG. 18.
Figure 29B:
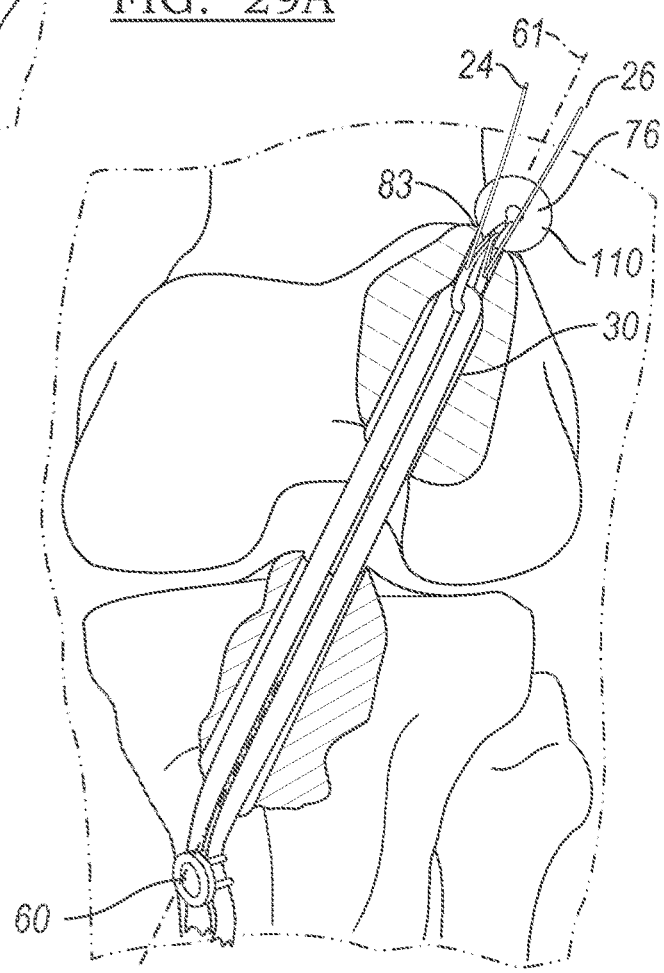

FIGS. 29A and 29B represent potential uses of the suture construction 86 in FIG. 18 in an ACL repair. As can be seen in FIG. 29A, the longitudinal passage portion 30 of suture construction 86 can be first coupled to a collapsible tube 76. The tube 76 can have a first profile which allows insertion of the tube 76 through the tunnel 62 and a second cross-sectional profile which allows engagement with a positive locking surface 103 upon collapse of the collapsible tube 76 into the fabric mass 110. The longitudinal passage portion 30 of the suture construction 84, tube 76, loops 46 and ends 24, 26 can then be pulled through a femoral and tibial tunnel 62. The tube 76 is positioned or coupled to the femur. At this point, a natural or artificial ACL 64 can be passed through a loop or loops 46 formed in the suture construction 20 or can be supported by the passage portion 30. Tensioning of the first and second ends 24 and 26 applies tension to the loops 46 and 47, thus pulling the ACL 64 into the tunnel. In this regard, the first and second ends are pulled through the femoral and tibial tunnel 62, thus constricting the loops 46 about the ACL 64.

After feeding the ACL 64 through the loops 46, tensioning of the ends allows engagement of the ACL with bearing surfaces defined on the loops. The tensioning pulls the ACL 64 through a femoral and tibial tunnel and collapses the tube 76 to form a locking fabric mass 110 outside the bone or tunnel 62. The ACL 64 could be further coupled to the femur or tibia using a transverse pin or plug. As shown in FIG. 29B, once the ACL is fastened to the tibia, further tensioning can be applied to the first and second ends 24, 26 placing a desired predetermined load on the ACL. As described above, this tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62. The longitudinal passage 30 resists relaxation or reverse movement of the suture.

As best seen in FIG. 29B, the body portion 28 and parallel portions 38, 40 of the suture construction 86 remain disposed within the femoral tunnel 62. Further tension of the first ends draws the ACL 64 up through the tibial component into the femoral component. In this way, suture ends can be used to apply appropriate tension onto the ACL 64 component. The ACL 64 would be fixed to the tibial component using a plug or screw either before or after the application of the tension to the suture 22. Additionally, tension can be set on the ACL 64 after the collapsible tube 76 has been compressed.

FIGS. 30A and 30B represent potential uses of the suture constructions 84 in FIG. 17 in an ACL repair. As can be seen in FIG. 30A, the longitudinal passage portion 30 of suture construction 86 can be first disposed within the tube 76. The tube 76 has a first profile which allows insertion of the tube 76 through the tunnel and a second collapsed profile which allows engagement with a positive locking surface 103. The collapsible tube 76 of the suture construction 84, member 60, and loops 46, 47 can then be passed through a femoral and tibial tunnel 62 using a suture 108. The tube 76 is positioned or coupled to the femur. At this point, a natural or artificial ACL 64 can be passed through a loop or loops 46, 47 formed in the suture construction 84. Tensioning of the first and second ends 24 and 26 applies tension to the loops 46, 47 thus pulling the ACL 64 into the tunnel. In this regard, the first and second ends 26 and 24 are pulled through the femoral and tibial tunnel, thus constricting the loops 46 about the ACL 64 (see FIG. 30B) and collapsing the tube 76 to form the anchoring mass 110. Force applied to graft 64 along axis 61 in the distal direction will seat tube 76 and form anchoring mass 110.

As shown, by holding the suture construction in place 108, the suture construction 84 allows for the application of force along an axis 61 defining the femoral tunnel 62. Specifically, the orientation of the suture construction 84 and, more specifically, the orientation of the longitudinal passage portion 30, the loops 46, and ends 24, 26 allow for tension to be applied to the construction 86 without applying non-seating forces to the tube 76. As an example, should the loops 24, 26 be positioned at the tube 76, application of forces to the ends 24, 26 may reduce the seating force applied by the tube 76 onto the bone.

As best seen in FIG. 30B, the loop portions 46, 47 of the suture construction 84 remain disposed within to the tunnel 62. Further tension of the first ends draws the ACL 64 up through the tibial component into the femoral component. In this way, suture ends can be used to apply appropriate tension onto the ACL 64 component. The ACL 64 would be fixed to the tibial component using a plug or screw 60 adjacent the suture construction 84, as is known.

Alternatively, as shown in FIG. 30B, once the ACL is fastened to the tibia, further tensioning can be applied to the first and second ends 24, 26 placing a desired predetermined load on the ACL. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

Figure 31A:
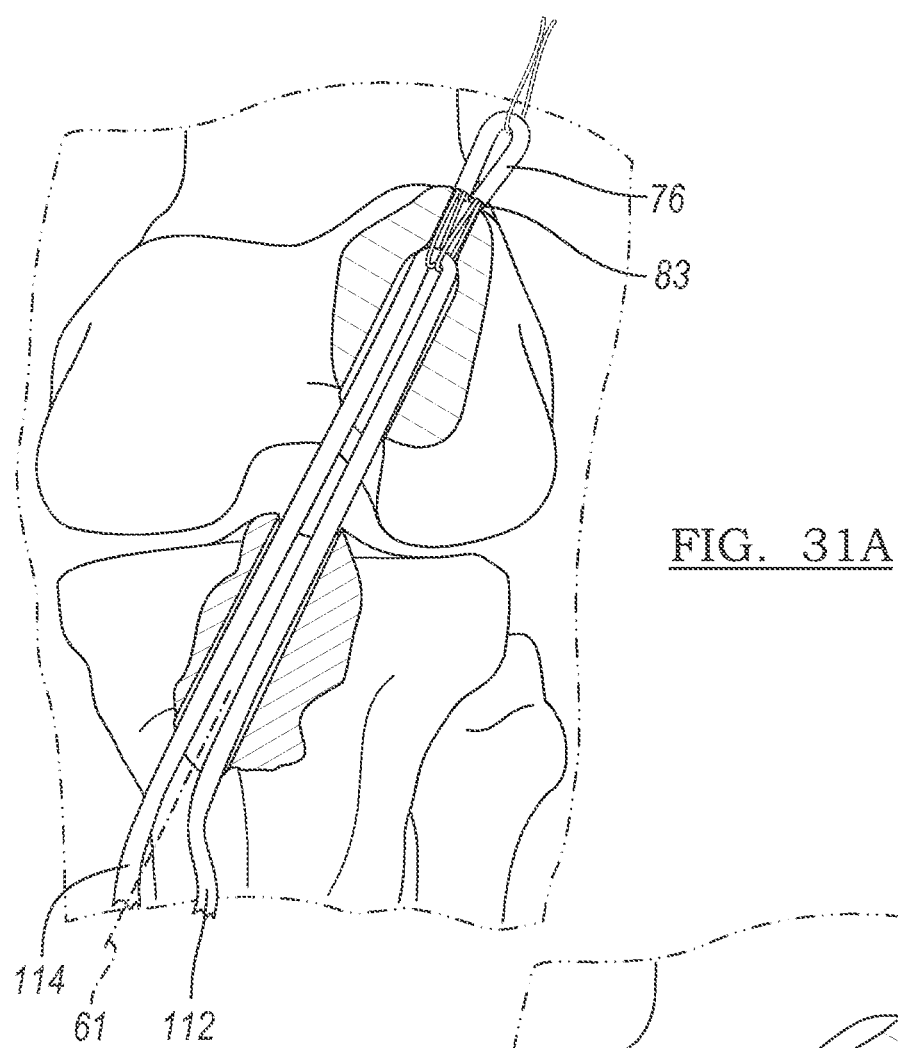
FIGS. 31A and 31B represent the coupling of an ACL replacement in the femoral/tibial reconstruction using the textile anchor of FIG. 15.
Figure 31B:
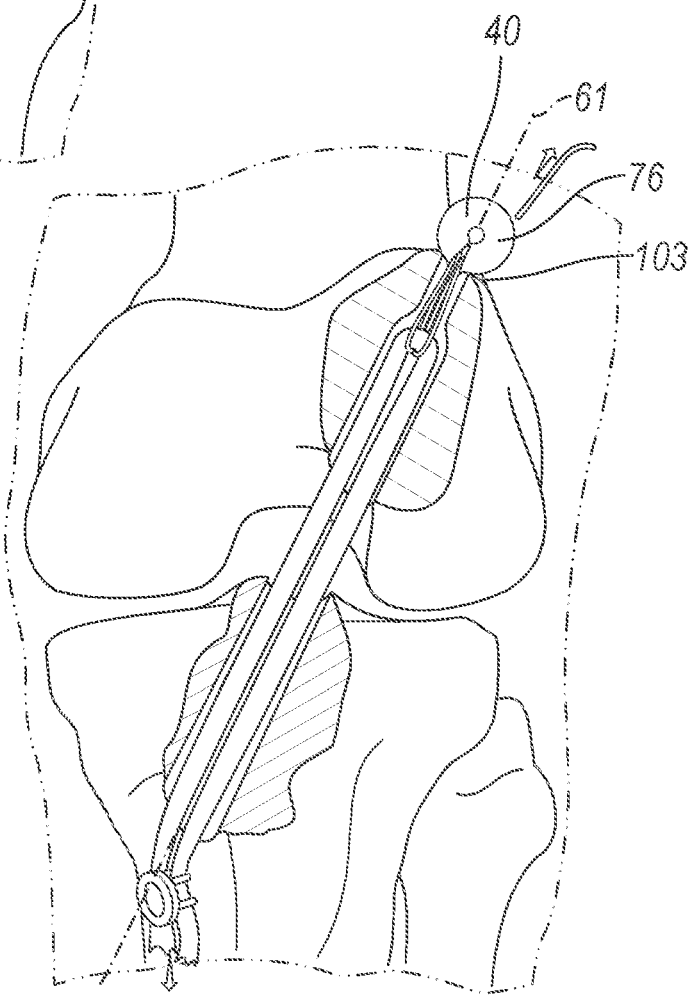

FIGS. 31A and 31B represent potential uses of the suture construction 70 in FIG. 14 in an ACL repair. The suture material 78 of suture construction 70 can be first coupled to a collapsible tube 76. The collapsible tube 76 can have a first profile which allows insertion of the construction 70 through the tunnel and a second profile which allows engagement with a positive locking surface 103 upon its compression. Prior to attachment to the femur, a natural or artificial ACL 64 can be passed through a loop or loops 46 formed in the suture material 78. Suture construction 70 can then be passed through a femoral and tibial tunnel 62. The tube 76 is positioned or coupled to the femur. Tensioning of the first and second ends 112 and 114 of the soft tissue applies tension to the loop 76, thus collapsing the tube 76 to form the fabric mass 110. Tension can be applied to the soft tissue which can then be fastened to the tibia using a fastener 60.

Figure 32A:
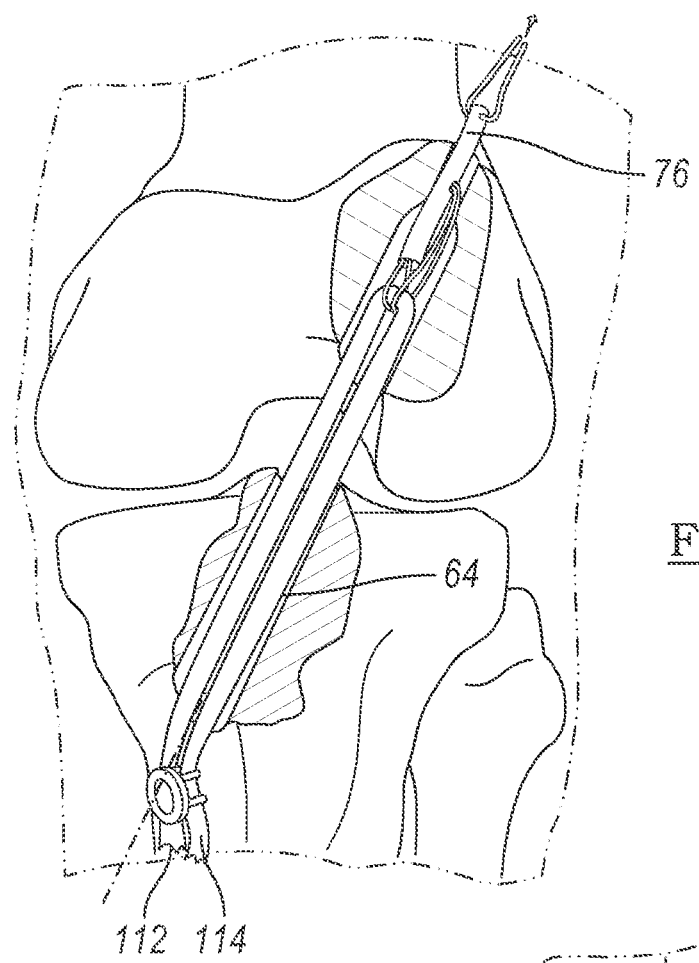
FIGS. 32A and 32B represent the coupling of an ACL replacement in a femoral/humeral reconstruction using the textile anchor of FIG. 16.
Figure 32B:
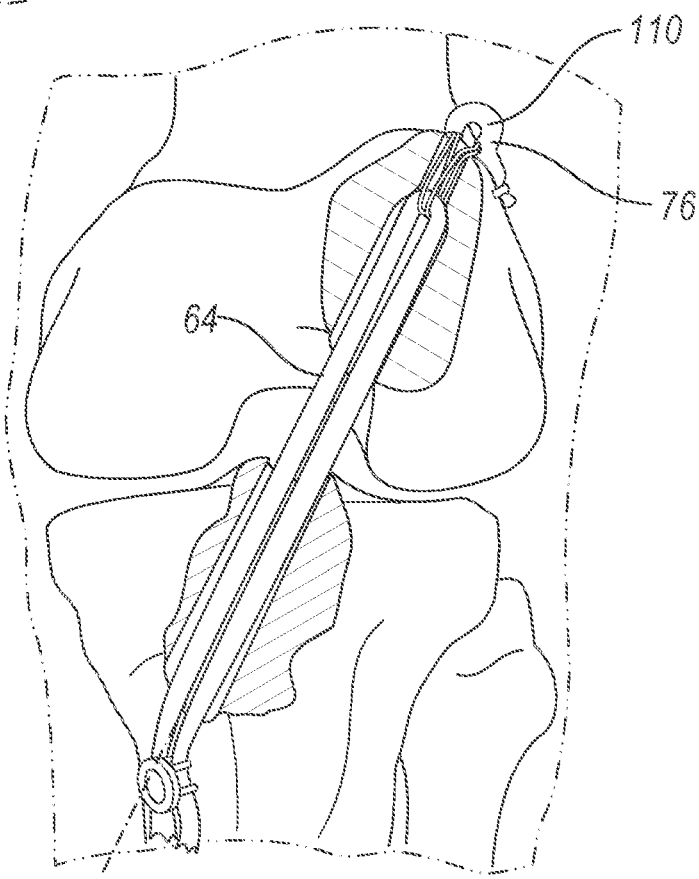

FIGS. 32A and 32B represent potential uses of the suture constructions 74 in FIG. 16 in an ACL repair. The loop of suture 78 is coupled to a collapsible tube 76. The construction 74 can have a first profile which allows insertion of the tube 76 through the tunnel and a second profile which allows engagement with a positive locking surface upon compression. The suture portion 78 of the suture construction 74, tube 76, and soft tissue 64 can then be passed through a femoral and tibial tunnel 62. The tube 76 is positioned or coupled to the femur 103 and collapsed by the application of tension to the soft tissue 64.

As best seen in FIG. 32B, the anchoring mass 110 of the suture construction 72 remains disposed outside the femoral tunnel. Tension is applied to the ends of the ACL 64 up through the tibial component into the femoral component. In this way, ends of the ACL 112, 114 can be used to apply appropriate tension onto the ACL 64 component. The ACL 64 would be fixed to the tibial component using a plug or screw as is known.

Figure 33:
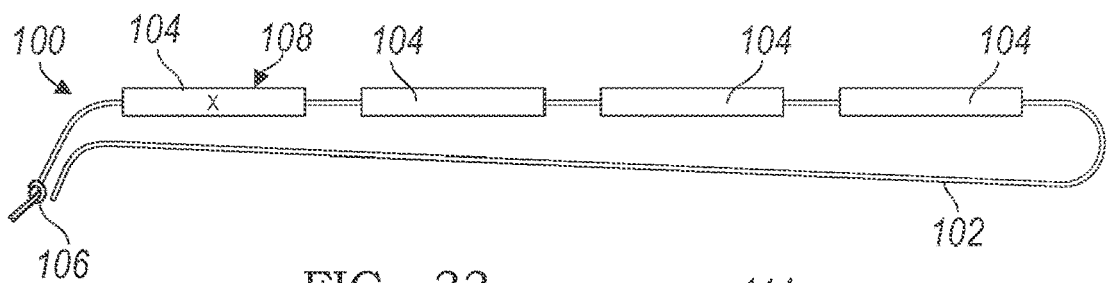
FIG. 33 represents a suture construction having a plurality of collapsible tubes.

FIG. 33 represents a suture construction 100 according to the present teachings. The suture construction 100 is formed of a suture 102 having a plurality of collapsible tubes 104 disposed thereon. The collapsible tubes 104 can be knit suture material or a polymer tube. Formed on one or both ends of the suture 102 can be a knot 106. Optionally, the collapsible tube 104 can be coupled to the suture 102 using a stitch 108, to prevent translation of the collapsible tube 104 with respect to the suture 102.

Figure 34A:
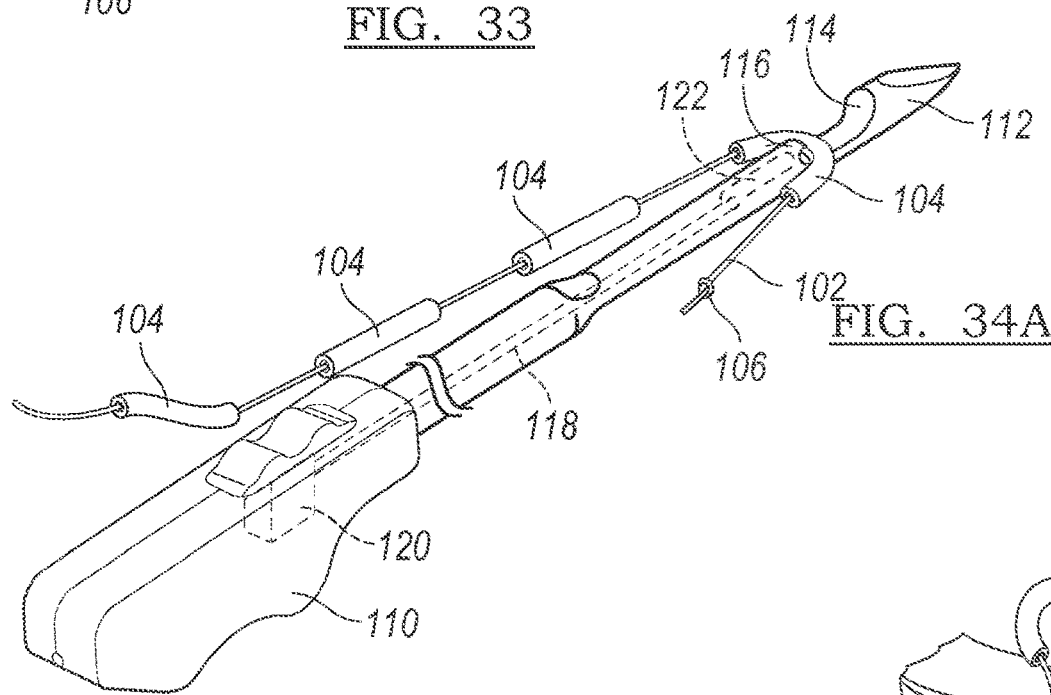
FIGS. 34A-34C represent a tool used to surgically implant the suture construction shown in FIG. 33.
Figure 34C:
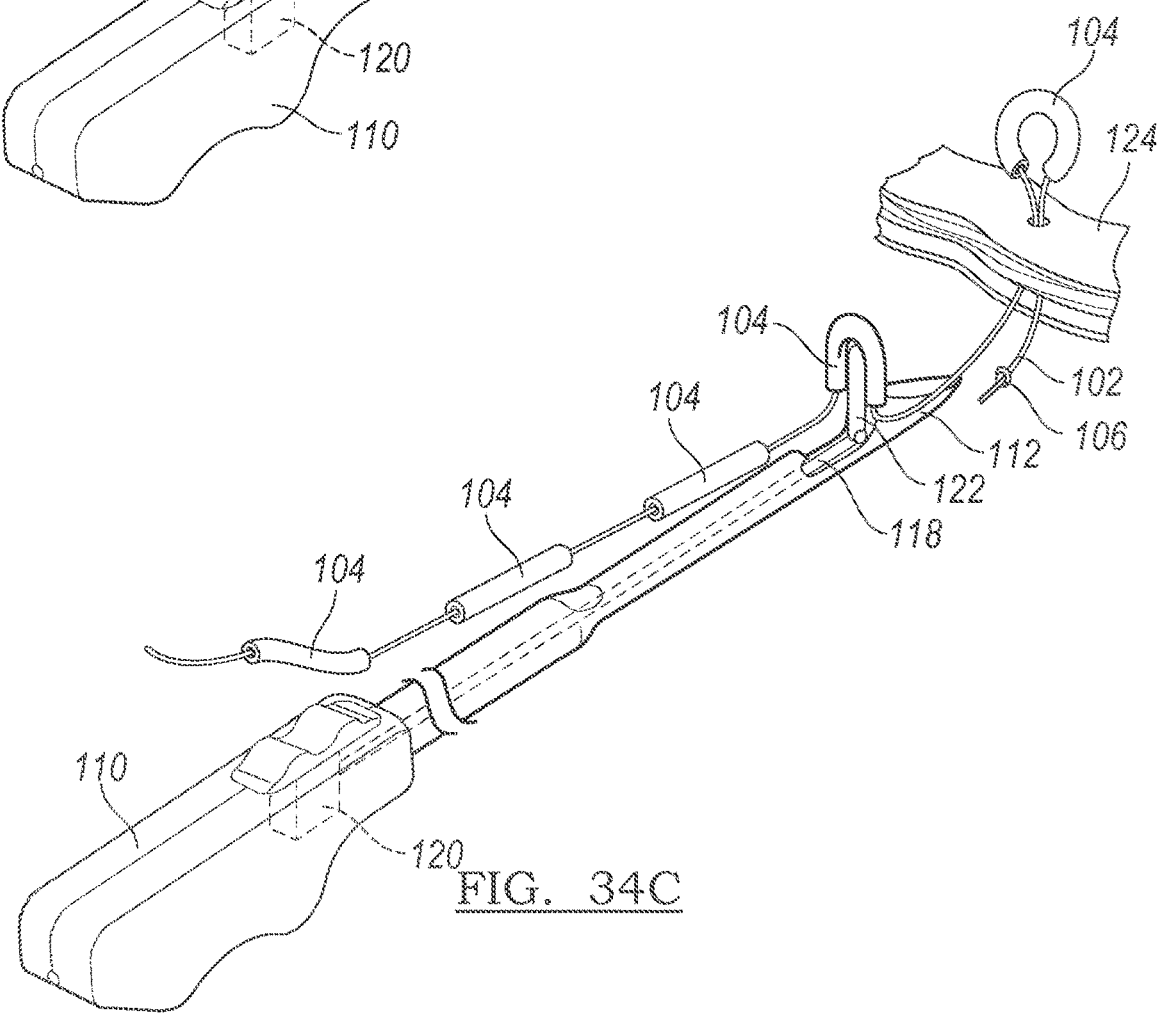
Figure 34B:
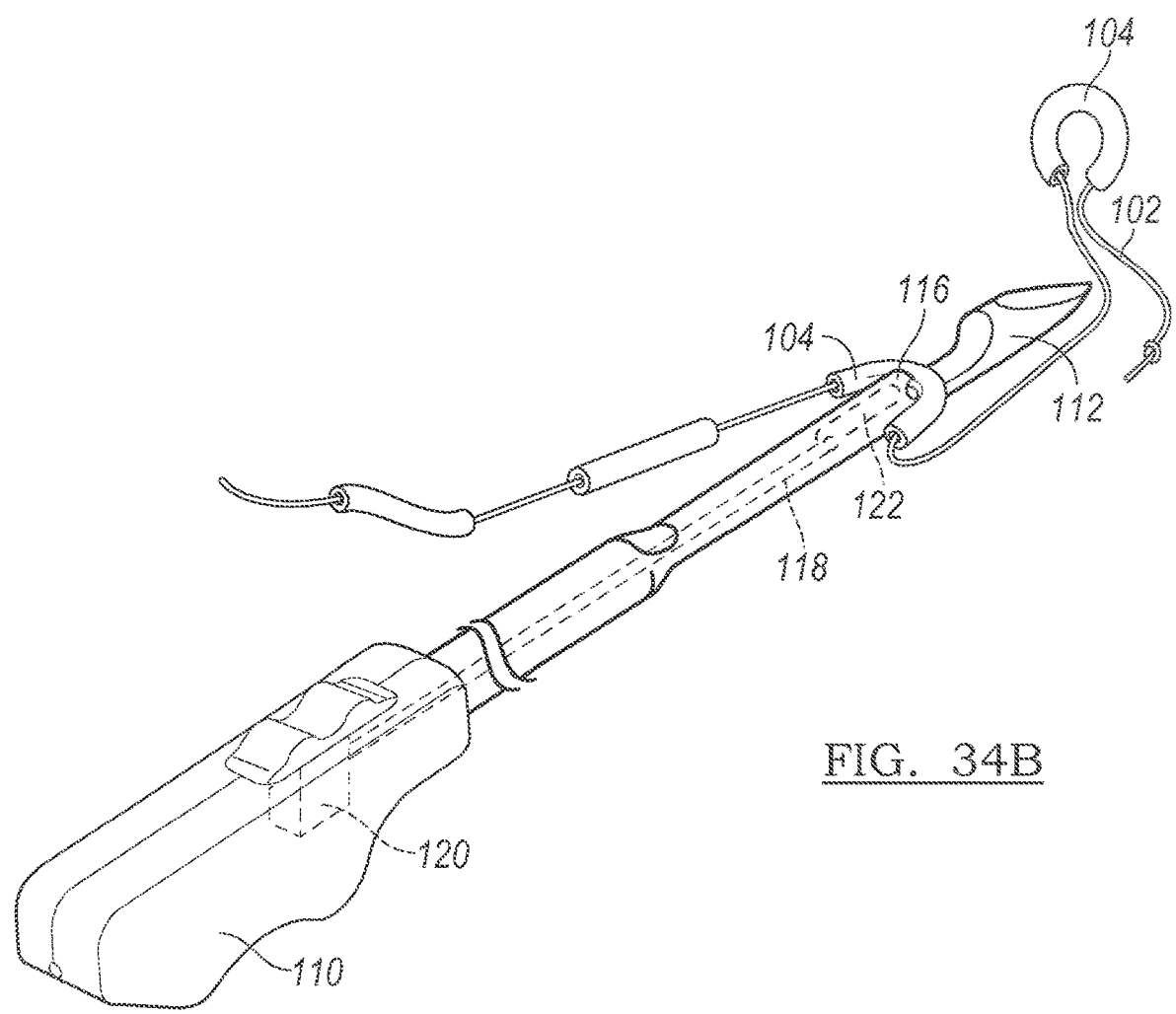

FIGS. 34A-34C represent a tool 110 used to couple the suture construction 100 with soft tissue. In this regard, the tool 110 has a sharpened end 112 configured to pierce soft tissue 124. Disposed adjacent the sharpened end 112 is a recess 114 configured to support a collapsible tube 104. Disposed within the recess 114 is a collapsible tube holding member 116. This member 116 can be a flange or a retractable member which selectively engages the collapsible tube 104 to hold the collapsible tube within the recess 114. Disposed within the tool 100 is an actuatable member 118. The actuatable member 118 functions to deploy or deliver the collapsible tube 104 from the holding member 116 of the recess 114. This generally occurs after the collapsible tube 104 has been pressed through the soft tissue 124.

As shown in FIG. 34D, the sharpened end 112 can be pressed through soft tissue 124, thus positioning the collapsible tube 104 on an obverse side of the soft tissue 124. Application of force by the drive member 120 onto the actuatable member 118 causes an engagable member 122 to deliver the collapsible tube 104 from the recessed portion 114 of the tool 110. the engagable member 122 can be formed of Nitonol or can be pivotably coupled to the actuatable member 118. At this point, the sharpened end can be removed from the soft tissue 124, leaving the compressible tube and its associated suture 102 therethrough.

Figure 35A:
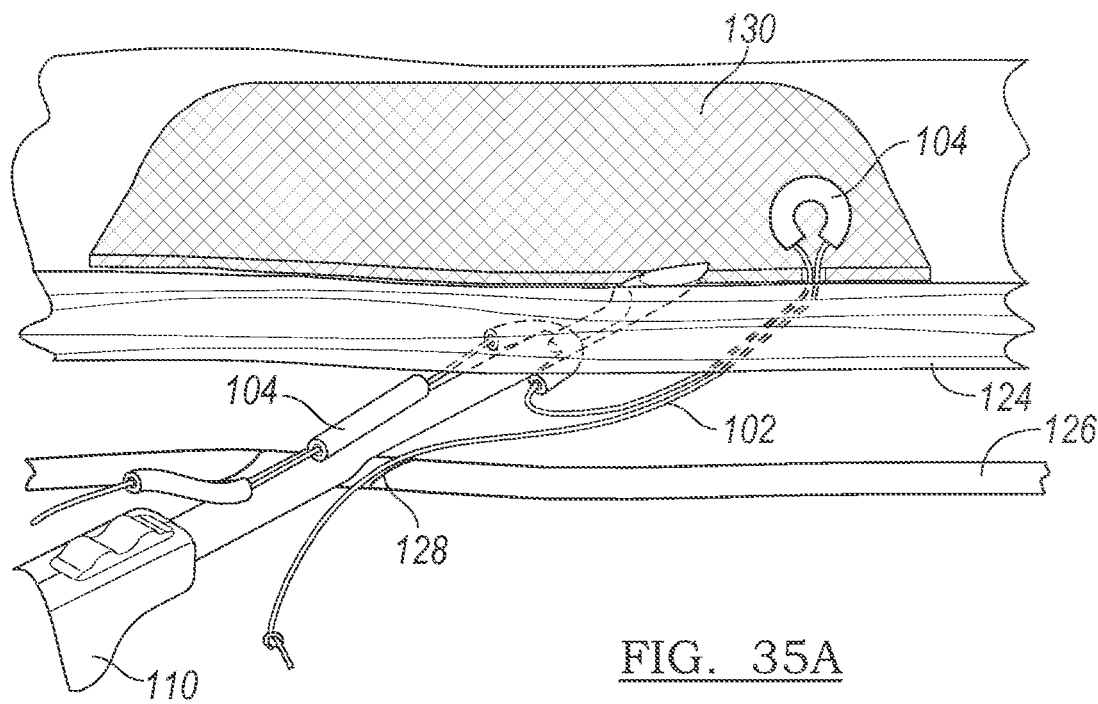
FIGS. 35A-35C show the suture construction of FIG. 33 coupled to an orthopedic mesh.
Figure 35B:
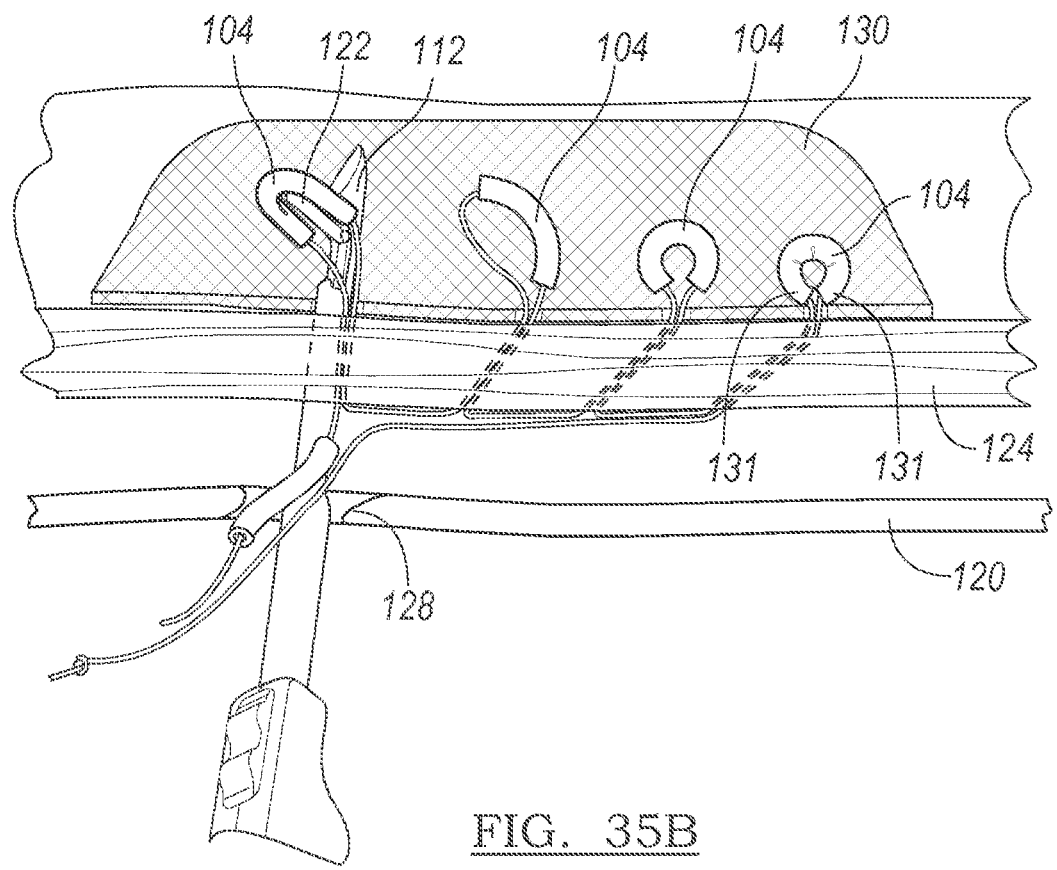
Figure 35C:
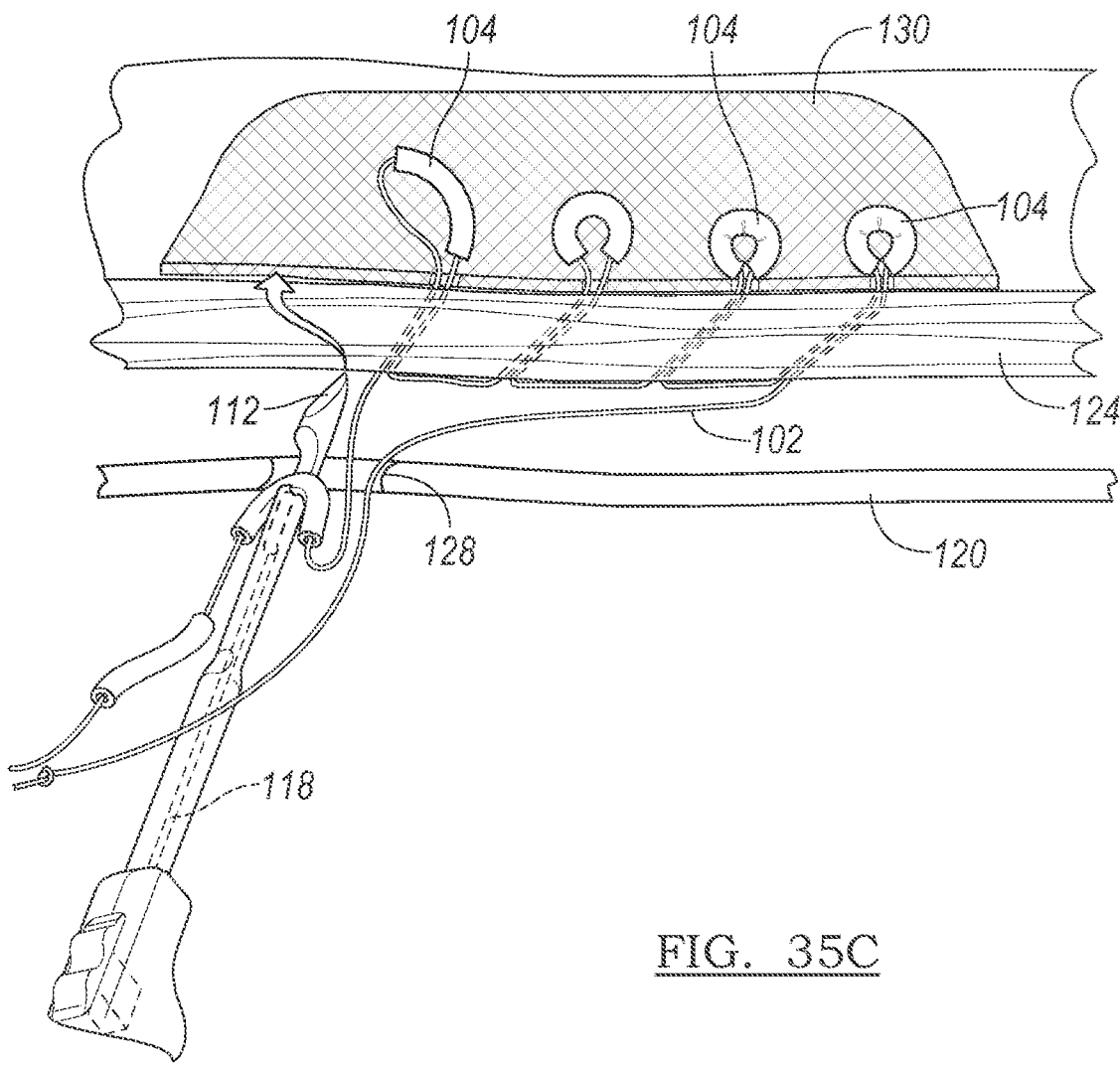

As shown in FIGS. 35A-35C, multiple collapsible tubes 104 on the suture 102 can be inserted through multiple apertures formed within the soft tissue 124. Additionally shown is an implantable orthopedic mesh 130. As best seen in FIG. 35B, the sharp end 112 of the tool 110 can be fed through a single aperture 128 formed in a layer of soft tissue 120 such as skin. The sharp end 112 is pressed through several apertures within the soft tissue 124 and through apertures within the implantable orthopedic mesh 130. The application of tensional force onto the suture 102 allows the ends 131 of the collapsible tubes 104 to engage the orthopedic mesh 130. This allows the collapsible tube 104 to form a loop structure locking the suture to the mesh 130. Further, the mesh is coupled to the soft tissue 124, bone, skin, tendon, xenograft, allograft and autograft.

As best seen in FIG. 35C, once the collapsible tube 104 has been positioned through the orthopedic mesh 130, the needle is withdrawn to allow the engagement of the next collapsible tube 104 within the recess 114 of the tool 110. The tool 110 is moved to position the sharp end 112 in a desired location on the soft tissue 124. Pressure is then applied to the tool 110 forming a hole within the soft tissue 124.

As described above, once the recess portion 114 is passed through the soft tissue 124 or the orthopedic sports mesh 130, the actuator 118 can be used to decouple the collapsible tube 104 from the recessed portion 114. The sports mesh can be one sold by Biomet Sports Medicine as Sport Mesh™. This allows the removal of the tool 110 while leaving collapsible tube 104 and associated suture 102 on the obverse side of the soft tissue 124 and the orthopedic mesh 130. The orthopedic h can be formed of resorbable materials.

Figure 36A:
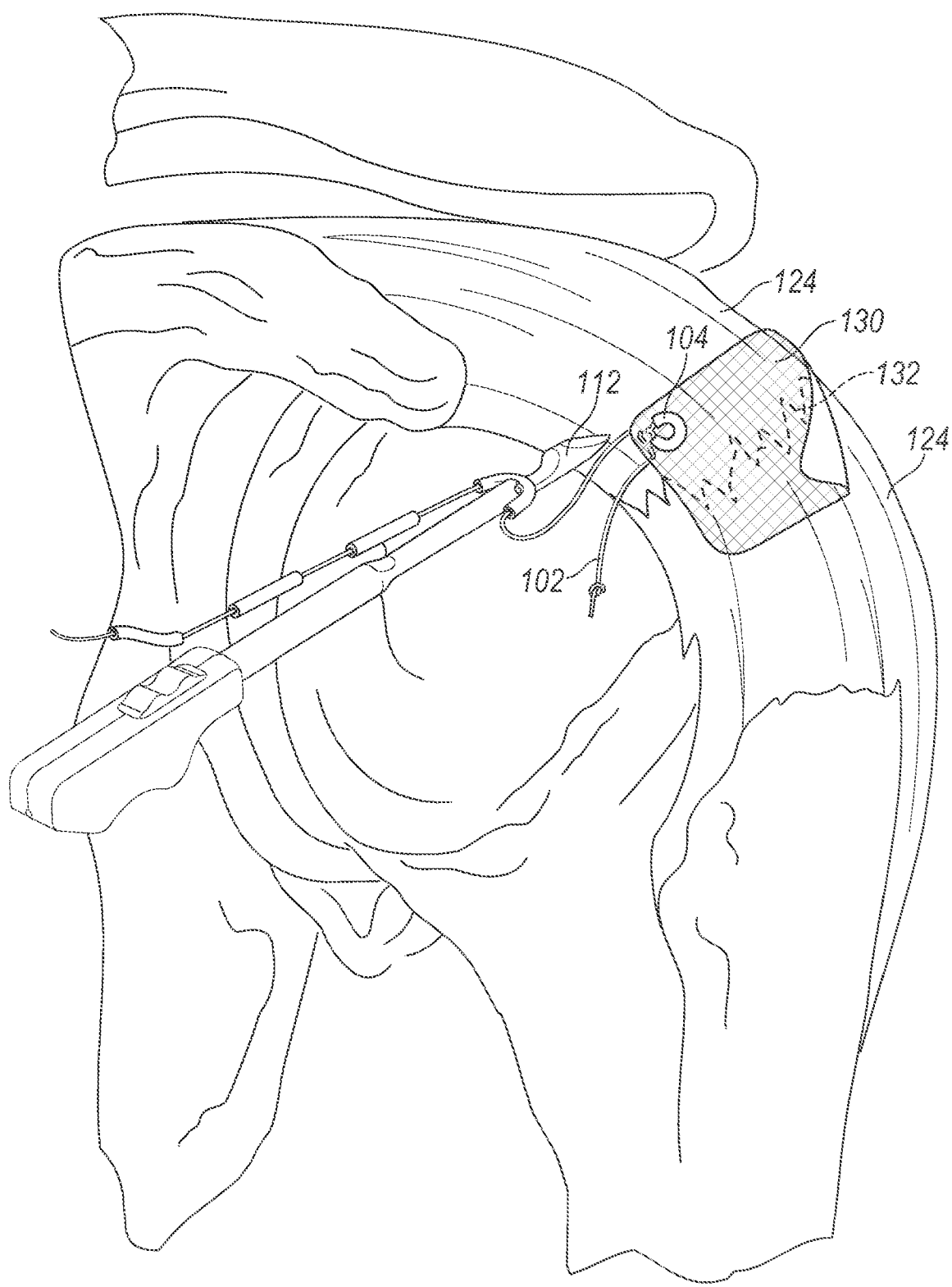
FIGS. 36A-36C represent the use of an orthopedic mesh to repair a soft tissue tear.
Figure 36B:
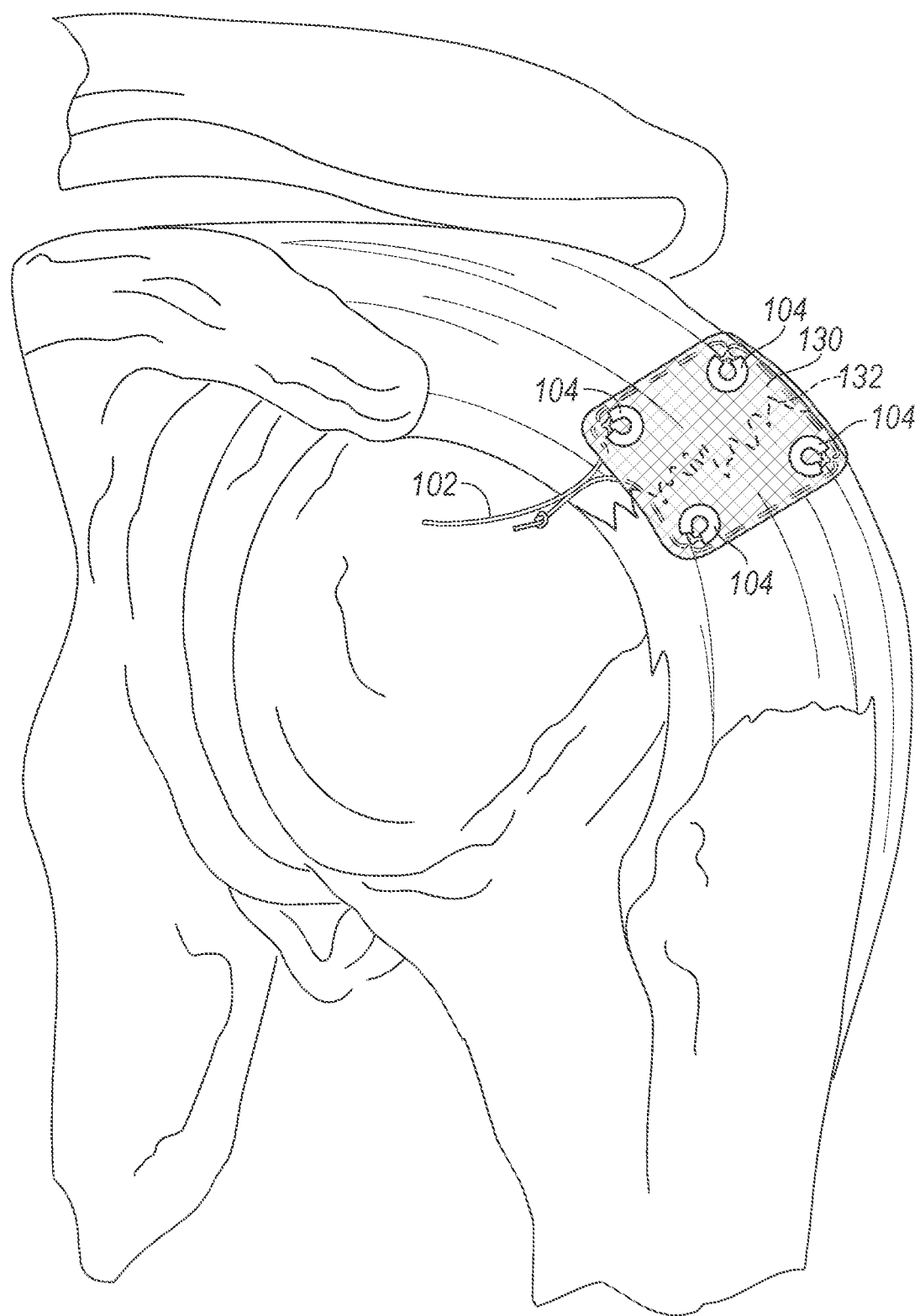
Figure 36C:
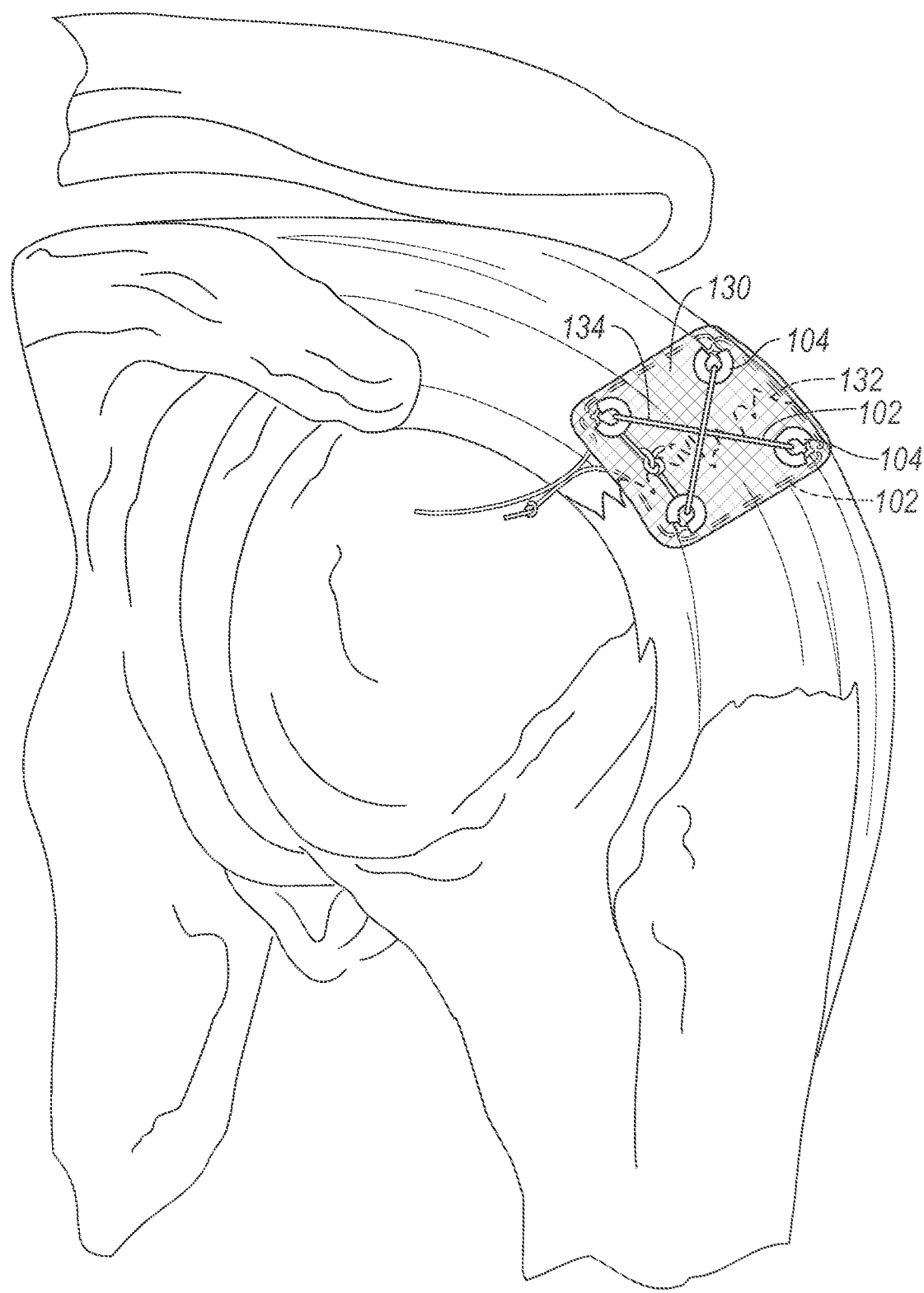

As shown in FIGS. 36A-36C, the construction in FIGS. 35A-35C and, particularly, the orthopedic mesh 130 can be used to repair torn soft tissue 124. In this regard, it is envisioned the mesh 130 can be placed over a muscle tear 132. A series of collapsible tubes 104 are disposed over a suture 102 and can be coupled to the soft tissue by pushing the collapsible tubes 104 through the soft tissue 124 and the mesh 130. Tension can be applied to the suture 102 to collapse the collapsible tube 104, thus coupling the sports mesh 130 to the two portions of soft tissue 124 which are being repaired.

As best seen in FIGS. 36B and 36C, several different stitching techniques can be used to couple multiple collapsible tubes 104 along the periphery of the orthopedic mesh 130 on either side of a tear 132. The orthopedic mesh 130 functions to distribute loads along the muscle 124, thus allowing the torn muscle 132 to heal properly.

As seen in FIG. 36C, sutures 134 can be added between the loops of collapsible tubes 104. It is envisioned that this functions to transfer loads from one portion of the muscle to a second, thus allowing the muscle tear 132 to heal more rapidly and compress the tear 132.

Figure 37A:
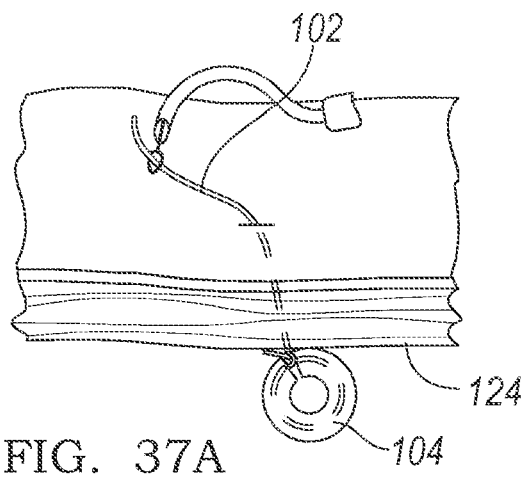
FIGS. 37A-39D represent various methodologies of coupling the suture constructions of FIG. 33 to soft tissue.
Figure 37B:
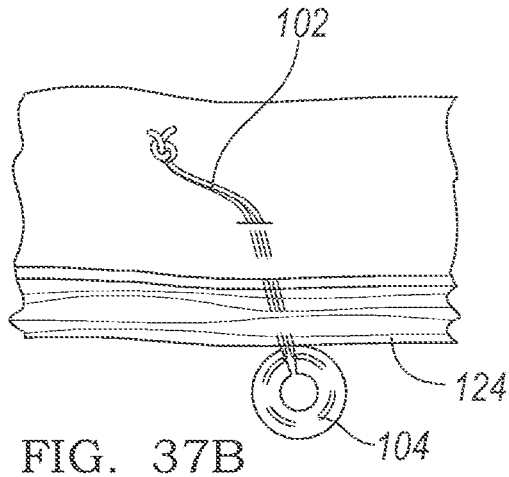

FIGS. 37A-39D represent various methods of inserting the suture constructions shown above into soft tissue. FIGS. 37A and 37B represent a collapsible tube having a single and double suture and constructions. These constructions are being threaded through a soft tissue 124, using a speed pass suture retriever from Biomet Sports Medicine. A passage is formed within a soft tissue 124 using the speed pass suture retriever has a deployable portion which can grab a suture and pull it through the passage. At this point, the suture construction having a suture 102 and collapsible tube Is positioned within the speed pass and pulled through the aperture formed within the soft tissue 124. Tension is applied to the suture 102, thus collapsing the collapsible tube 104.

Figure 38A:
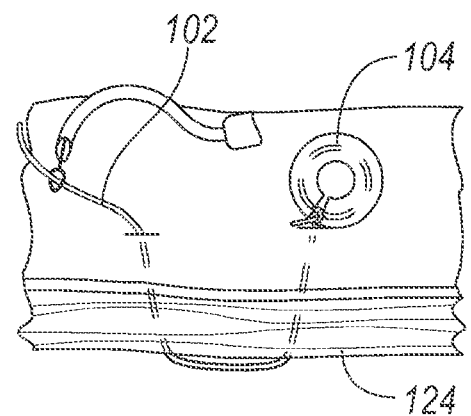
Figure 38B:
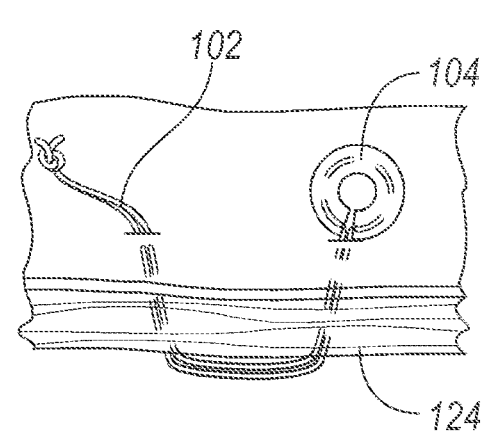
Figure 39A:
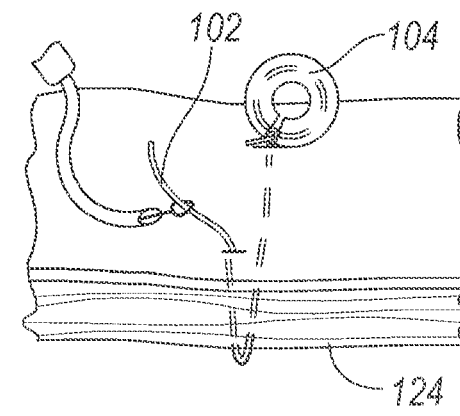
Figure 39B:
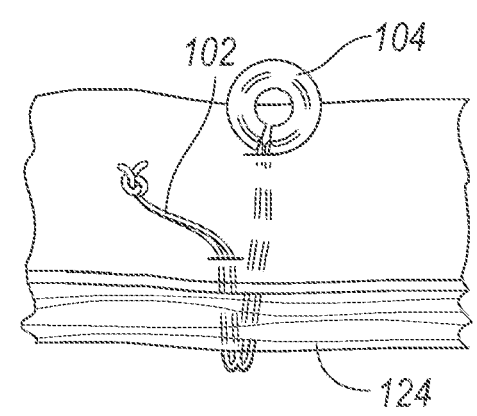
Figure 37C:
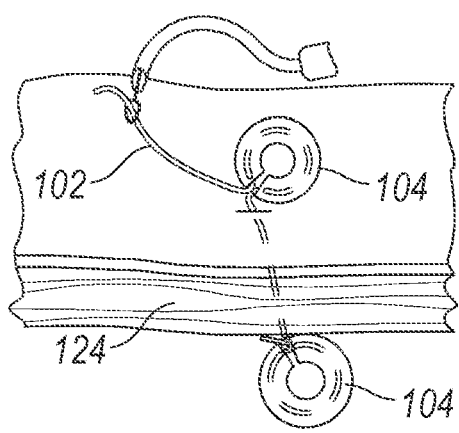
Figure 37D:
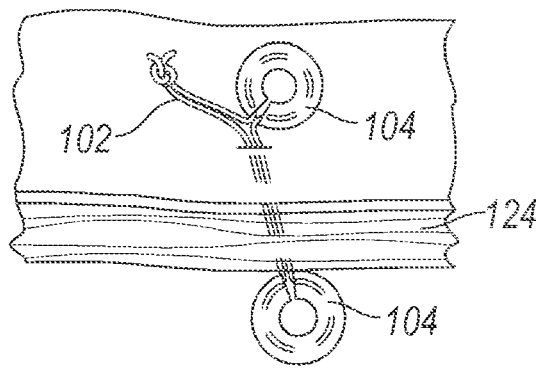
Figure 38C:
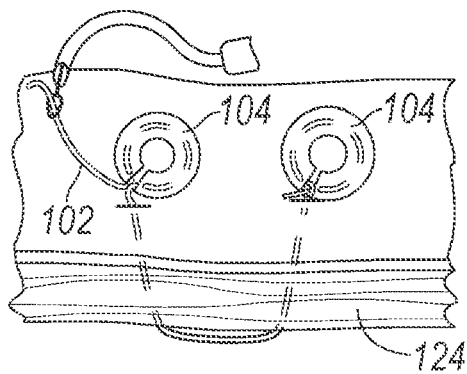
Figure 38D:
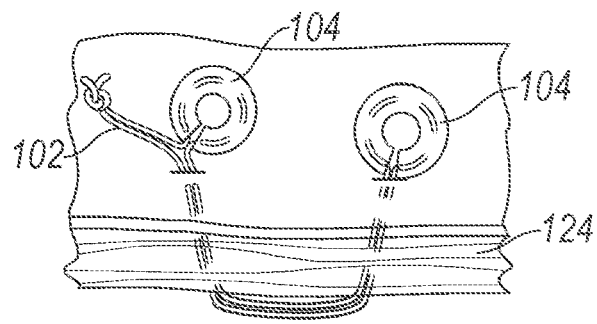
Figure 39C:
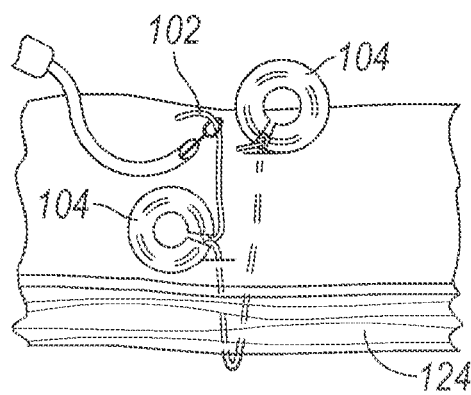
Figure 39D:
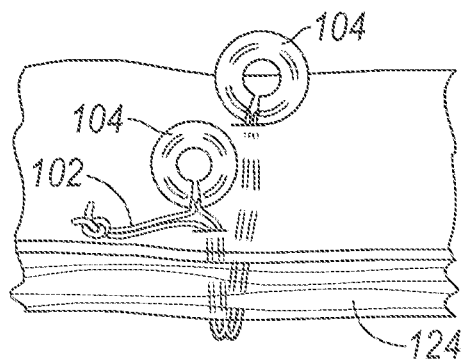
Figure 40:
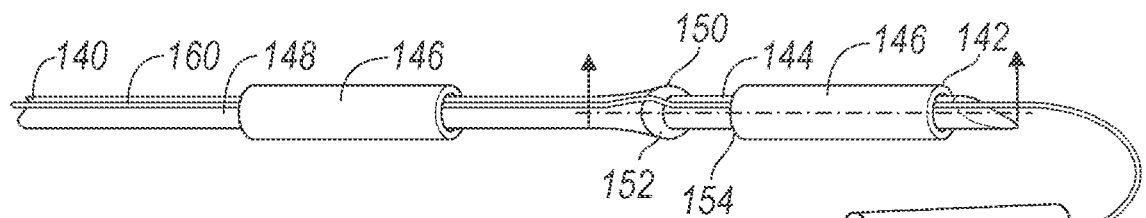
FIGS. 40-45 represent an alternate suture construction.

As seen in FIGS. 38A and 38B, by using a curved speed pass instrument, a pair of apertures can be formed within the soft tissue. The speed pass instrument is then used to pull the suture construction through the two apertures formed in the soft tissue 124. Alternatively, the suture construction may be pressed within the speed pass 125 and released (pushed out) after the speed pass 125 has pierced the soft tissue.

As seen in FIGS. 38A and 38B, the speed pass having a corkscrew shape can be used to form a pair of apertures in soft tissues which are generally perpendicular to the tool threading direction. In each of these conditions, tension is applied to the sutures 102 to compress the tubes 104. It is envisioned the speed pass can be used to feed the suture constructions through the orthopedic mesh as described above.

Figure 41:
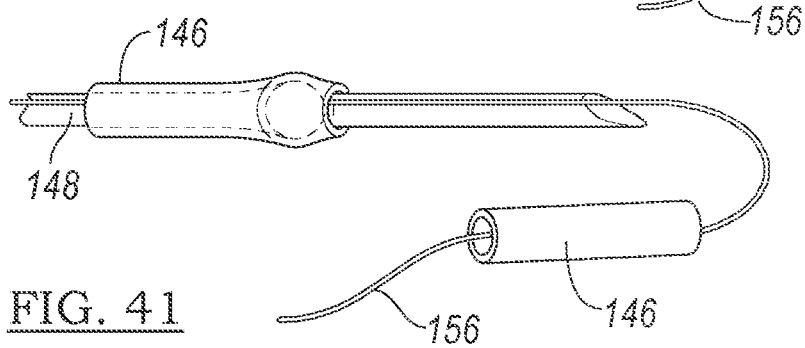
Figure 42:
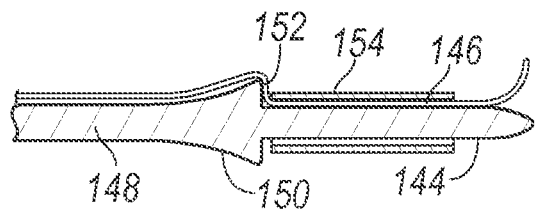

FIGS. 40-45 represent a tool 140 used to couple the suture construction 100 with soft tissue. In this regard, the tool 140 has a sharpened end 142 configured to pierce soft tissue 124. Disposed adacent to the sharpened end 142 is a first portion 144 configured to support a collapsible tube anchor 146. Adjacent to the first portion 144 is a second portion 148 which can support a plurality of collapsible tube anchors 146. Disposed between the first 144 and second portions 148 is a generally conical portion 150. As shown in FIG. 41, the conical portion 150 facilitates movement of the collapsible tubes 146 from the second portion 148 to the first portion 144. Defined between the conical portion 150 and the first portion 144 is a generally flat or planar support surface 152. The flat surface 152 is configured to support and apply axial forces to an end 154 of the collapsible tube anchor 146.

Figure 43:
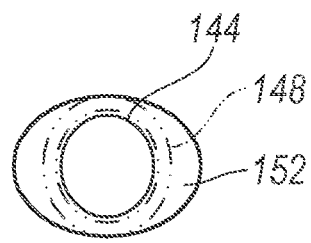
Figure 44:
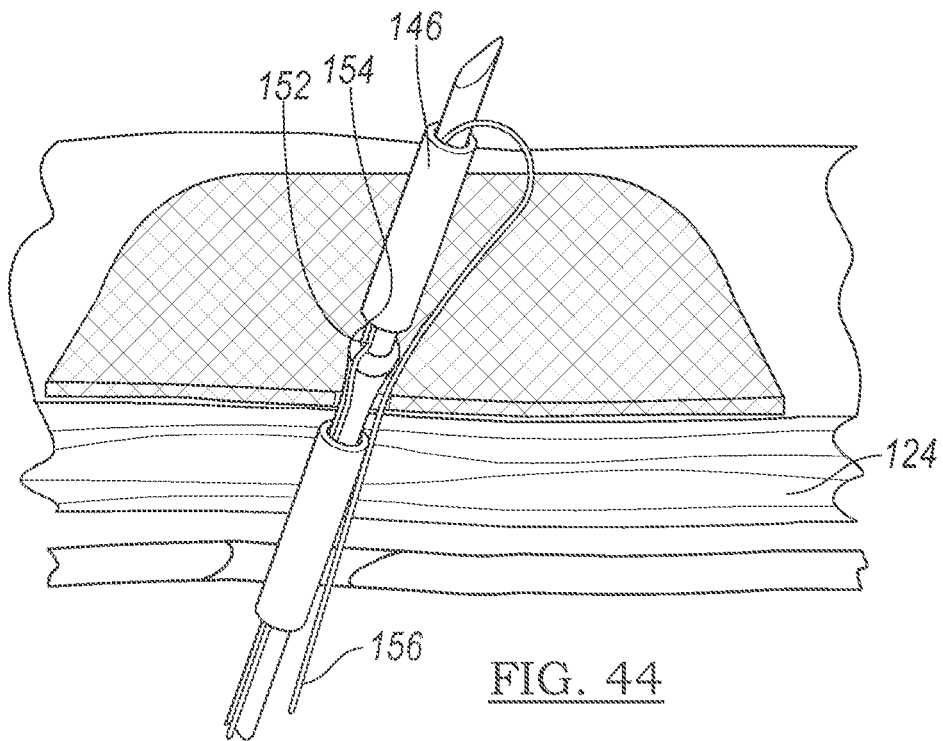

As best seen in FIG. 43, the conical portion 150 can have an oblong cross-section. This cross-section can help facilitate the passing of the suture through the soft tissue. The sharpened end 142 can be passed through soft tissue 124, thus placing the collapsible tube 146 on an obverse side of the soft tissue 124. At this point, the sharpened end 142 can be passed through another soft tissue layer, a shorts mesh, or skin.

Figure 45:
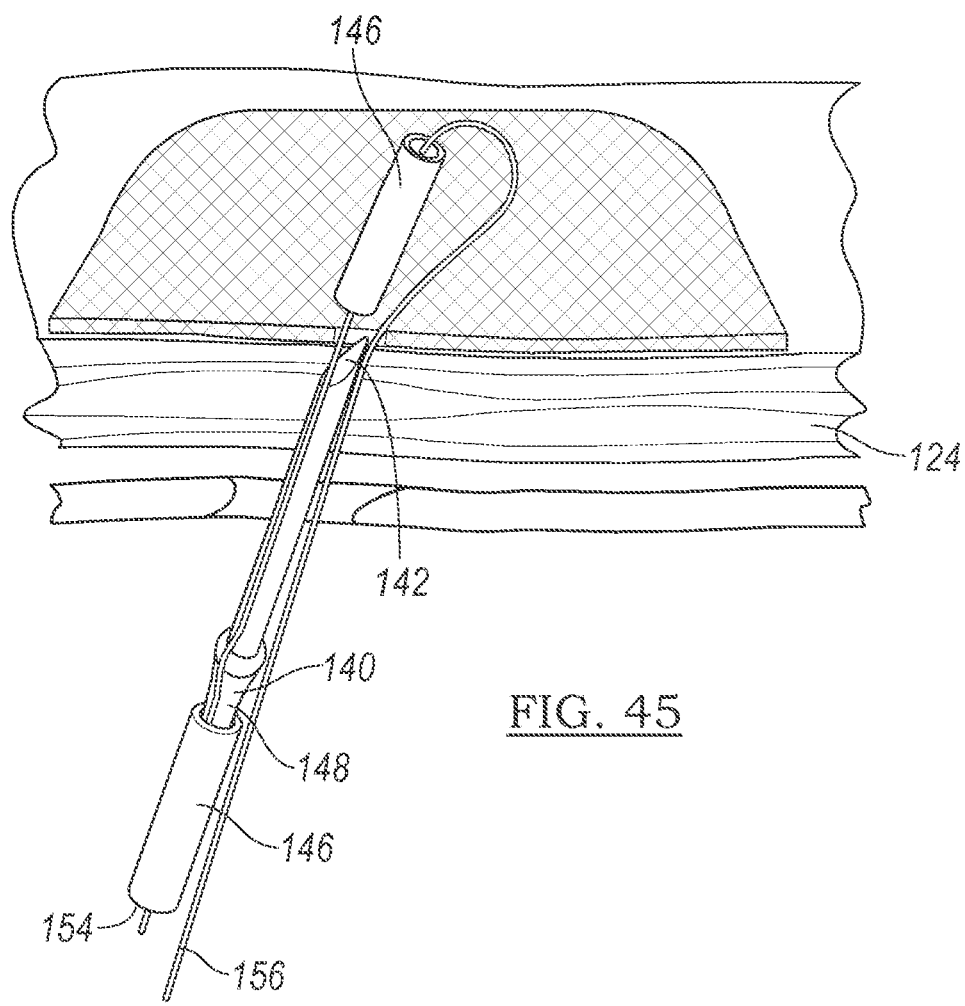

As shown in FIG. 45, the tool 140 can be withdrawn leaving the collapsible tube 146 on the obverse side of the soft tissue. Force can then be applied to the suture 156, as described above, to collapse the collapsible tube 146.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Such variations are not to be regarded as a departure from the spirit and scope of the invention.

What is claimed is:

1. A suture anchor assembly for anchoring suture to bone, the suture anchor assembly comprising:
a suture; and
a collapsible tubular anchor coupled to the suture, the collapsible tubular anchor having an elongated shape and being collapsible from a first condition to a second condition while coupled to the suture, the first condition of the collapsible tubular anchor permitting advancement of the collapsible tubular anchor in a first direction through a tunnel formed in bone from a first end of the tunnel toward a second end of the tunnel, the second condition of the collapsible tubular anchor forming an anchoring mass for contacting bone in the tunnel for inhibiting movement of the collapsible tubular anchor back through the tunnel in a second direction opposite the first direction, wherein, in the second condition, the collapsible tubular anchor includes alternating curved sections extending along a length of the collapsible tubular anchor, the alternating curved sections including first curved sections curving in a first direction alternating with second curved sections curving in a second direction opposite the first direction,
wherein, in the second condition, the collapsible tubular anchor being coupled to the suture includes multiple separate in-and-out occurrences along the length of the collapsible tubular anchor where the suture goes into the collapsible tubular anchor and then out of the collapsible tubular anchor, said multiple separate in-and-out occurrences including an individual in-and-out occurrence between each of the first curved sections such that: (i) each of the first curved sections that curve in the first direction is unoccupied by the suture; and (ii) each of the second curved sections that curve in the second direction is occupied by the suture, wherein each of the second curved sections being occupied by the suture includes the suture extending longitudinally through a respective longitudinal bore of each of the second curved sections.

2. The suture anchor assembly of claim 1 in combination with an inserter carrying the collapsible tubular anchor.

3. The suture anchor assembly of claim 2, wherein the collapsible tubular anchor is folded in half on the inserter.

4. The suture anchor assembly of claim 1, wherein the collapsible tubular anchor is formed with a suture material.

5. The suture anchor assembly of claim 1, wherein the collapsible tubular anchor is formed with a knit, woven, or braided material.

6. The suture anchor assembly of claim 1, wherein a first free end of the suture extends longitudinally through a longitudinal bore in the suture to form an adjustable loop.

7. The suture anchor assembly of claim 6, wherein at least part of the adjustable loop extends away from the collapsible tubular anchor.

8. A suture anchor assembly for anchoring suture to bone, the suture anchor assembly comprising:
a suture; and
a collapsible tubular anchor coupled to the suture, the collapsible tubular anchor formed with a knit, woven, or braided material and having an elongated shape, the collapsible tubular anchor collapsible from a first condition to a second condition while coupled to the suture, the first condition of the collapsible tubular anchor permitting advancement of the collapsible tubular anchor in a first direction through a tunnel formed in bone from a first end of the tunnel toward a second end of the tunnel, the second condition of the collapsible tubular anchor forming an anchoring mass for contacting bone in the tunnel for inhibiting movement of the collapsible tubular anchor back through the tunnel in a second direction opposite the first direction, wherein, in the second condition, the collapsible tubular anchor includes a plurality of curved sections along a length of the collapsible tubular anchor, the plurality of curved sections including at least a first curved section, a second curved section, a third curved section, a fourth curved section, and a fifth curved section that occur in succession and have alternating directions of curvature along the length of the collapsible tubular anchor,
wherein, in the second condition, the collapsible tubular anchor being coupled to the suture includes multiple separate in-and-out occurrences along the length of the collapsible tubular anchor where the suture goes into the collapsible tubular anchor and then out of the collapsible tubular anchor, said multiple separate in-and-out occurrences including a first in-and-out occurrence between the first curved section and the third curved section and a second in-and-out occurrences between the third curved section and the fifth curved section such that: (i) each of the first curved section, the third curved section, and the fifth curved section is unoccupied by the suture; and (ii) each of the second curved section and the fourth curved section is occupied by the suture, wherein each of the second curved section and the fourth curved section being occupied by the suture includes the suture extending longitudinally through a respective longitudinal bore of the second curved section and the fourth curved section.

9. The suture anchor assembly of claim 8 in combination with an inserter carrying the collapsible tubular anchor.

10. The suture anchor assembly of claim 9, wherein the collapsible tubular anchor is folded in half on the inserter such that a middle section of the collapsible tubular anchor engages a portion of the inserter with a first end and a second end of the collapsible tubular anchor extending away from the middle section in the same direction.

11. The suture anchor assembly of claim 8, wherein the collapsible tubular anchor is formed with a suture material.

12. The suture anchor assembly of claim 8, wherein a first free end of the suture extends longitudinally through a longitudinal bore in the suture to form an adjustable loop, at least part of the adjustable loop extending away from the collapsible tubular anchor.

13. A suture anchor assembly for anchoring suture to bone system, the suture anchor assembly comprising:
a suture; and
a collapsible tubular anchor coupled to the suture, the collapsible tubular anchor having an elongated shape and being collapsible from a first condition to a second condition while coupled to the suture, the first condition of the collapsible tubular anchor permitting advancement of the collapsible tubular anchor in a first direction through a tunnel formed in bone from a first end of the tunnel toward a second end of the tunnel, the second condition of the collapsible tubular anchor forming an anchoring mass for contacting bone in the tunnel for inhibiting movement of the collapsible tubular anchor back through the tunnel in a second direction opposite the first direction, wherein, in the second condition, the collapsible tubular anchor is folded in half along a middle section of the collapsible tubular anchor and includes alternating curved sections extending along a length of the collapsible anchor, the alternating curved sections including first curved sections curving in a first direction alternating with second curved sections curving in a second direction opposite the first direction,
wherein, in the second condition, the collapsible tubular anchor being coupled to the suture includes multiple separate in-and-out occurrences along the length of the collapsible tubular anchor where the suture goes into the collapsible tubular anchor and then out of the collapsible tubular anchor, said multiple separate in-and-out occurrences including an individual in-and-out occurrence between each of the first curved sections such that: (i) each of the first curved sections that curve in the first direction is unoccupied by the suture; and (ii) each of the second curved sections that curve in the second direction is occupied by the suture, wherein each of the second curved sections being occupied by the suture includes the suture extending longitudinally through a respective longitudinal bore of each of the second curved sections.

14. The suture anchor assembly of claim 13, wherein a first free end of the suture extends longitudinally through a first longitudinal bore in the suture to form a first adjustable loop.

15. The suture anchor assembly of claim 14, wherein at least part of the first adjustable loop extends away from the collapsible tubular anchor.

16. The suture anchor assembly of claim 13, wherein the collapsible tubular anchor is formed with a suture material.

17. The suture anchor assembly of claim 13, wherein the collapsible tubular anchor is formed with a knit, woven, or braided material.

18. The suture anchor assembly of claim 17, wherein the collapsible tubular anchor is formed with a suture material.

19. The suture anchor assembly of claim 13, wherein the collapsible tubular anchor is formed with a braided nylon.

20. The suture anchor assembly of claim 13 in combination with an inserter carrying the collapsible tubular anchor, the collapsible tubular anchor folded in half on the inserter.

* * * * *